United States Patent
Ouk et al.

(10) Patent No.: US 10,226,464 B2
(45) Date of Patent: Mar. 12, 2019

(54) SMALL MOLECULE NF-κB INHIBITORS

(71) Applicant: ImmuneTarget, Inc., San Diego, CA (US)

(72) Inventors: Samedy Ouk, San Diego, CA (US); Hsiou-Chi Liou, New York, NY (US)

(73) Assignee: ImmuneTarget, Inc., San Diego, CA (US)

( * ) Notice: Subject to any disclaimer, the term of this patent is extended or adjusted under 35 U.S.C. 154(b) by 0 days.

(21) Appl. No.: 15/393,507

(22) Filed: Dec. 29, 2016

(65) Prior Publication Data

US 2017/0182051 A1  Jun. 29, 2017

Related U.S. Application Data

(60) Provisional application No. 62/272,408, filed on Dec. 29, 2015.

(51) Int. Cl.
| | |
|---|---|
| *A61K 31/519* | (2006.01) |
| *C07D 491/113* | (2006.01) |
| *C07D 491/14* | (2006.01) |
| *C07D 491/052* | (2006.01) |
| *C07D 495/04* | (2006.01) |

(52) U.S. Cl.
CPC ........ *A61K 31/519* (2013.01); *C07D 491/052* (2013.01); *C07D 491/14* (2013.01); *C07D 495/04* (2013.01); *A61K 2121/00* (2013.01)

(58) Field of Classification Search
None
See application file for complete search history.

(56) References Cited

U.S. PATENT DOCUMENTS 4,272,535 A    6/1981  Blythin et al.
7,498,336 B2 *  3/2009  Weissman ............ C07D 471/04
                                                    514/267

FOREIGN PATENT DOCUMENTS

WO    2008014266 A2    1/2008
WO    2008014266 A3    1/2008
WO    2008014266 A9    1/2008

OTHER PUBLICATIONS

Byrn, Stephen. Solid-State Chemistry of Drugs, 2nd Ed. (1999), Ch. 11 Hydrates and Solvates, 233-247.*
Rouhi, A.M. Chem. & Eng. News, (2003), 81(8), 32-35.*
Morissette, Sherry. Adv. Drug Delivery Rev. 2004, 56, 275-300.*
Chen, Zhijian. Nat Cell Biol. Aug. 2005; 7(8): 758-765.*
Aly, Hala. European Journal of Medicinal Chemistry 47(2012) 18-23.*
Rotili, Dante. J. Med. Chem. (2012) 55, 18, 8193-8197.*
Hala M. Aly et al: "Efficient one-pot preparation of novel fused chromeno[2,3-d]pyrimidine and pyrano[2,3-d] pyrimidine derivatives", European Journal of Medicinal Chemistry, vol. 47, 2012, pp. 18-23.
David J. Blythin et al: "Simple synthetic route to "oxa-deazaflavins" (2H-[1]-benzopyrano[2,3-d]pyrimidine-2,4 (3H)-diones)", Heterocycles, vol. 16, No. 2, 1981, p. 203.
Rebecca L. Chan et al: "The chemistry of an electron-deficient 5-deazaflavin. 8-Cyano-10-methyl-5-Deazaisoalloxazine", Journal of the American Chemical Society, vol. 99, No. 20, 1977, pp. 6721-6730.
Xiaoxue Dou et al: "Synthesis and biological evaluation of novel pyrimido[4,5-b]quinoline-2,4-dione derivatives as MDM2 ubiquitin ligase inhibitors", Medicinal Chemistry, vol. 9, No. 4, 2013, pp. 581-587.
Tetsuji Kawamoto et al: "Synthesis and evaluation of nitro 5-deazaflavins as novel bioreductive antitumor agents", Bioorganic & Medicinal Chemistry Letters, vol. 5, No. 18, 1995, pp. 2109-2114.
Kenya Mori et al: "Novel synthesis of pyrimido[4,5-b]quinoline-2(3H),4(10H)-dion es (5-deazaflavins)", Journal of the Chemical Society, Chemical Communications., No. 17, 1978, p. 764.
V. Pande et al: "NF-[kappa] B in human disease: current inhibitors and prospects for de nova structure based design of inhibitors", Current Medicinal Chemistry, vol. 12, No. 3, 2005, pp. 357-374.
Fumio Yoneda et al: "Synthesis and properties of 1-benzothiopyrano[2,3-d]pyrimidine-2,4(3H)-dione (5-deaza-10-thiaflavin)", Tetrahedron Letters, vol. 19, No. 31, 1978, pp. 2803-2806.
Fumio Yoneda et al: "Syntheses of 5-deazaflavines", Journal of the Chemical Society, Perkin Transactions 1, No. 16, 1976, pp. 1805-1808.
International Search Report and Written Opinion of the International Searching Authority, PCT/US2016/069124, dated Feb. 28, 2017.
Stephen Berge: "Pharmaceutical Salts", Journal of Pharmaceutical Sciences, vol. 66, No. 1, 1977, pp. 1-20.

* cited by examiner

*Primary Examiner* — Deepak R Rao
*Assistant Examiner* — Laura M Daniel
(74) *Attorney, Agent, or Firm* — Proskauer Rose LLP

(57) ABSTRACT

The present invention provides, inter alia, compounds capable of inhibiting NF-κB. Pharmaceutical compositions containing and methods of using the compounds are also provided herein.

20 Claims, 14 Drawing Sheets

Fig. 3A

| IV administration | | 5 mg/kg | | | | | | | | | | | |
|---|---|---|---|---|---|---|---|---|---|---|---|---|---|
| Animal | No. of pts used for t½ | t½ (hr) | C₀ (ng/mL) | AUC_last (hr*ng/mL) | AUC_inf (hr*ng/mL) | AUC Ext (%) | V_z (L/kg) | V_ss (L/kg) | CL (mL/min/kg) | MRT (hr) | Last time point for AUClast (hr) | Time points for T1/2 (hr) | Rsq |
| Mouse 1 | 3 | 0.566 | 1211 | 893 | 899 | 0.336 | 4.59 | 2.96 | 92.7 | 0.491 | 4 | 0.5, 3, 4 | 0.973 |
| Mouse 2 | 3 | 1.47 | 3632 | 989 | 992 | 0.238 | 12.1 | 2.60 | 91.6 | 0.391 | 4 | 2, 4, 8 | 0.954 |
| Mouse 3 | 3 | 0.665 | 1738 | 825 | 826 | 0.332 | 5.19 | 2.36 | 93.1 | 0.369 | 4 | 0.5, 3, 4 | 0.933 |
| N | 3 | 3 | 3 | 3 | 3 | 3 | 3 | 3 | 3 | 3 | | | |
| Mean | | 0.888 | 2128 | 903 | 905 | 0.285 | 6.82 | 2.48 | 92.5 | 0.452 | | | |
| SD | | 0.088 | 1529 | 79 | 79 | 0.047 | 4.64 | 0.38 | 7.9 | 0.051 | | | |
| CV% | | 56.6 | 82.4 | 8.78 | 8.76 | 16.6 | 68.0 | 15.8 | 8.54 | 11.9 | | | |

SMALL MOLECULE NF-κB INHIBITORS

CROSS-REFERENCE TO RELATED APPLICATIONS

The present application claims priority to U.S. provisional application Ser. No. 62/272,408, filed Dec. 29, 2015, the entire contents of which are incorporated by reference herein.

FIELD OF INVENTION

The present invention provides, inter alia, compounds and pharmaceutical compositions capable of inhibiting NF-κB, as well methods of using said compounds and compositions.

BACKGROUND OF THE INVENTION

NF-κB/Rel (nuclear factor kappa B) is a family of transcription factors that includes p50/p105 (NF-κB1), p52/p100 (NF-κB2), p65 (RelA), c-Rel, and RelB. These molecules can homo- or heterodimerize, and are generally sequestered in the cytoplasm by their inhibitors, IκBs. Upon activation, IκBs are degraded by the 26s proteasome and NF-κB dimers migrate into the nucleus to perform transcriptional activity.

NF-κB (p50/p65) and c-Rel are regulated by the canonical IKKα/β/γ kinase complex pathway, whereas RelB and p52 (NF-κB2) are regulated by an alternative pathway via the IKKα/NIK complex. Despite this similarity, each NF-κB family member is distinct with regard to tissue expression pattern, response to receptor signals, and target gene specificity. These differences are evident from the non-redundant phenotypes exhibited by individual NF-κB/Rel knockout mice. Therefore, therapeutics targeted to different NF-κB/Rel members are likely to have different biological effects and toxicity profiles.

Many receptors and stimuli can activate NF-κB/Rel, including TCR/BCR, TNF receptor superfamily (e.g. CD40, TNFR1, TNFR2, BAFF, APRIL, RANK), IL-1/TLR receptors, and Nod-like receptors, as well as activating oncogenes (e.g. Src, Ras, LMP-1, Tax, v-FLIP), reactive oxygen radicals, radiation, and chemotherapeutic agents. In response to these stimuli, NF-κB/Rel regulates the expression of cytokines, chemokines, and molecules that play a role in adhesion, the cell cycle, apoptosis, and angiogenesis. As such, NF-κB/Rel transcription factors are important therapeutic targets for many human disorders, including inflammation, autoimmune diseases, and cancer, and small molecule inhibitors of NF-κB/Rel may be useful as therapeutics for these disorders.

SUMMARY OF THE INVENTION

The present invention relates to compounds capable of inhibiting NF-kB/Rel.

One embodiment of the present invention is a compound. The compound has a structure of formula (I)

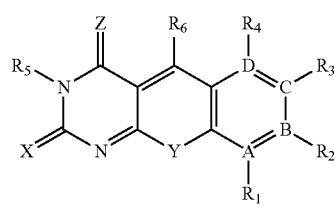

(I)

wherein:

A, B, C, and D are independently selected from the group consisting of carbon and nitrogen;

X, Y, and Z are independently selected from the group consisting of oxygen, sulfur, and $NR^a$;

$R_1$, $R_2$, $R_3$, and $R_4$ are independently selected from the group consisting of no atom, hydrogen, halogen, $C_{1-9}$ alkyl, $C_{1-9}$ alkenyl, $C_{1-9}$ alkynyl, aryl, $C_{1-9}$ heterocyclic, —OH, —$OR^a$, —$OR^aOR^b$, —$OR^aOR^bOR^c$, —$OR^a(C=O)R^b$, —$O(C=O)R^a$, —$O(C=O)OR^a$, —$O(C=O)NR^aR^b$, cyano, nitro, —$CF_3$, —$CHF_2$, —$CH_2F$, —CHO, —COOH, —$COR^a$, —$COOR^a$, —$CONR^aR^b$, —$CONHCONR^aR^b$, —$NR^aR^b$, —$NHCOR^a$, —$NR^bCOR^a$, —CSOH, —$CSR^a$, —$CSOR^a$, —$CSNR^aR^b$, —$CSNHCSNR^aR^b$, —SH, —$SR^a$, —$S(C=O)R^a$, —$S(C=O)OR^a$, —$S(C=O)NR^aR^b$;

$R_5$ is selected from the group consisting of hydrogen, $C_{1-9}$ alkyl, $C_{1-9}$ alkenyl, $C_{1-9}$ alkynyl, aryl, $C_{1-9}$ heterocyclic, —$R^aCO$, —$R^aNHCO$, and —$R^aOCO$; and $R_6$, $R^a$, $R^b$, and $R^c$ are independently selected from the group consisting of hydrogen, hydroxyl, amine, $C_{1-9}$ alkyl, $C_{1-9}$ alkenyl, $C_{1-9}$ alkynyl, aryl, and $C_{1-9}$ heterocyclic, or is a crystalline form, hydrate, or pharmaceutically acceptable salt thereof.

Another embodiment of the present invention is a compound. The compound is selected from the group consisting of:

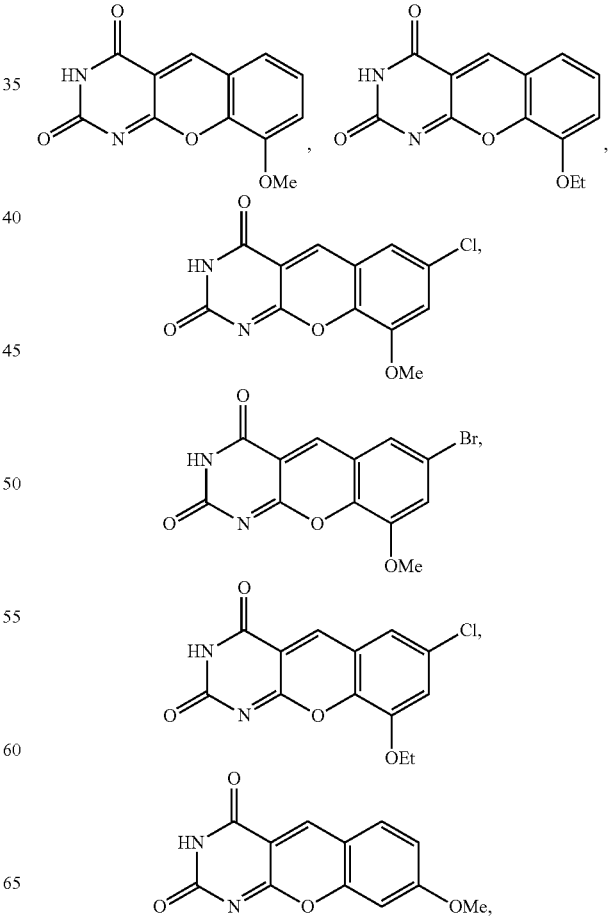

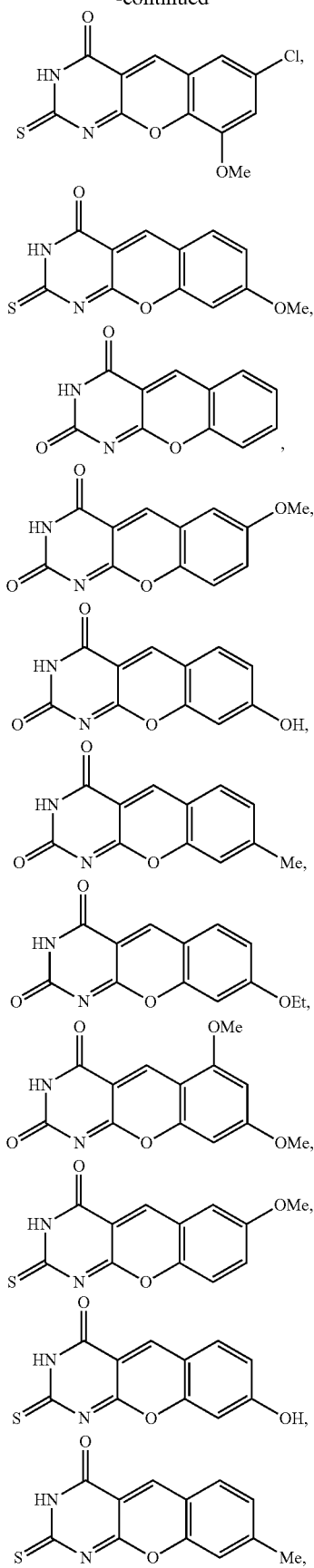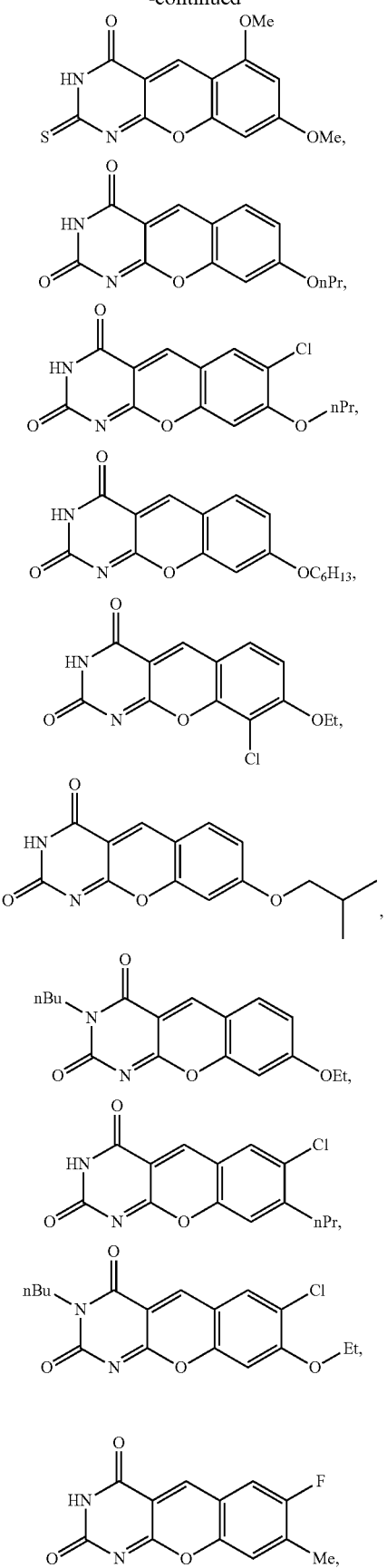

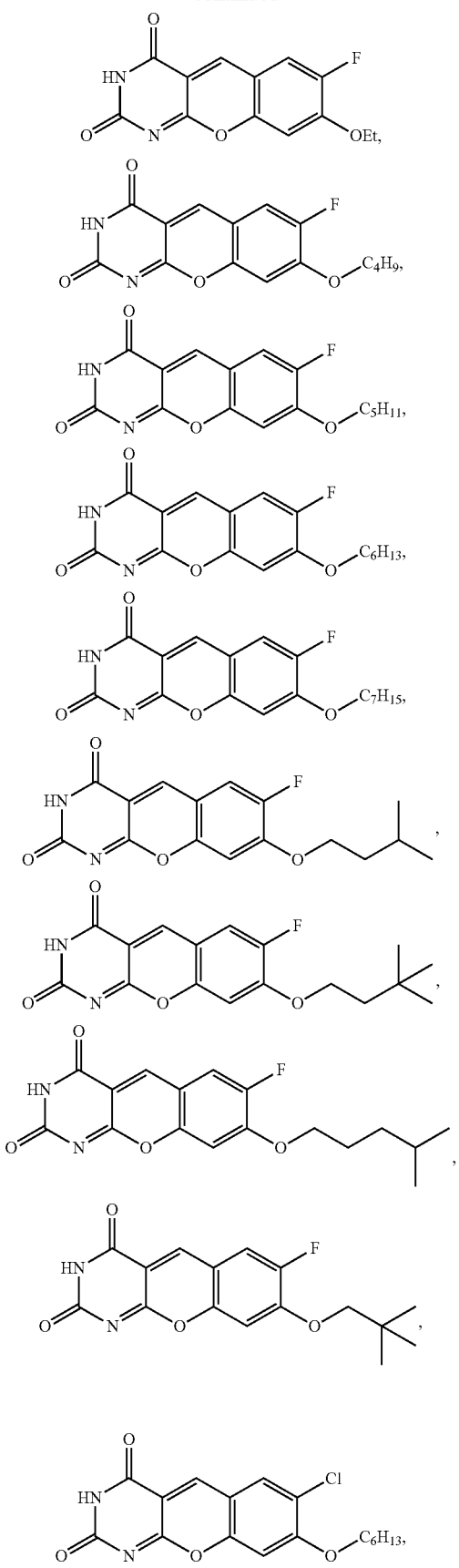
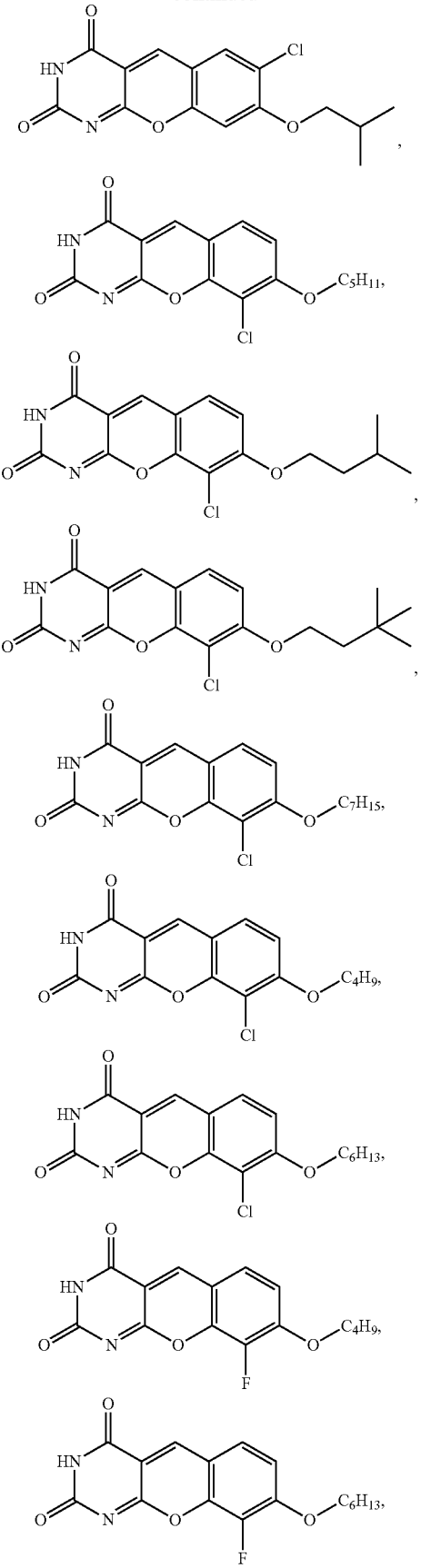

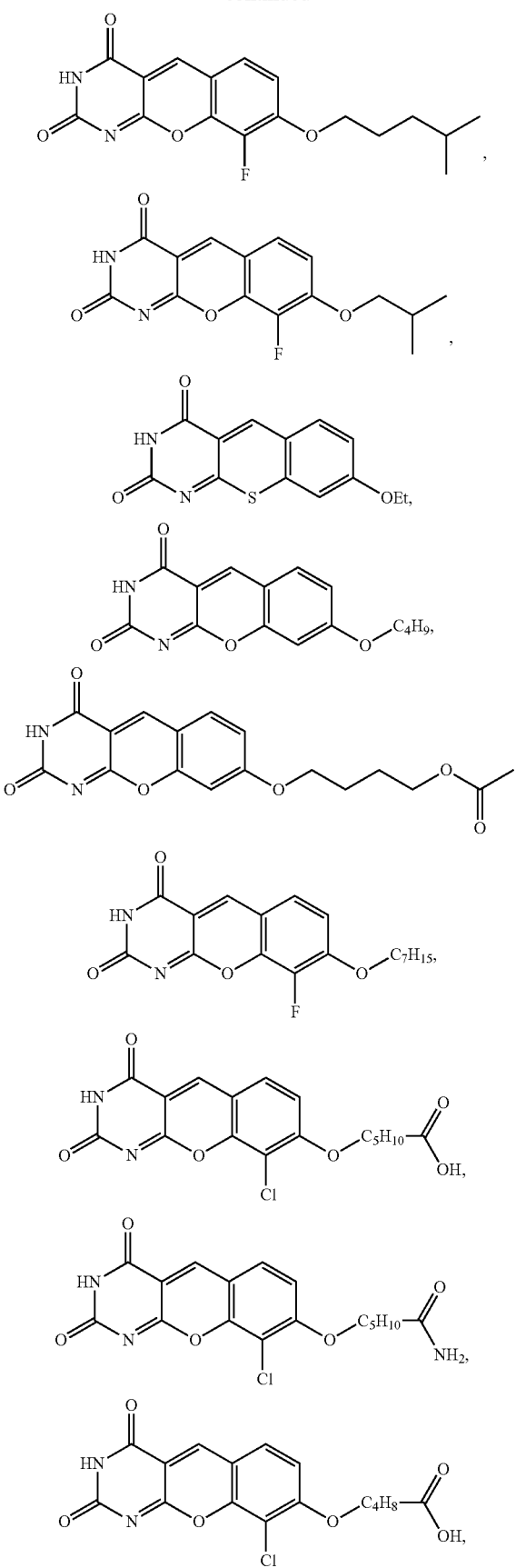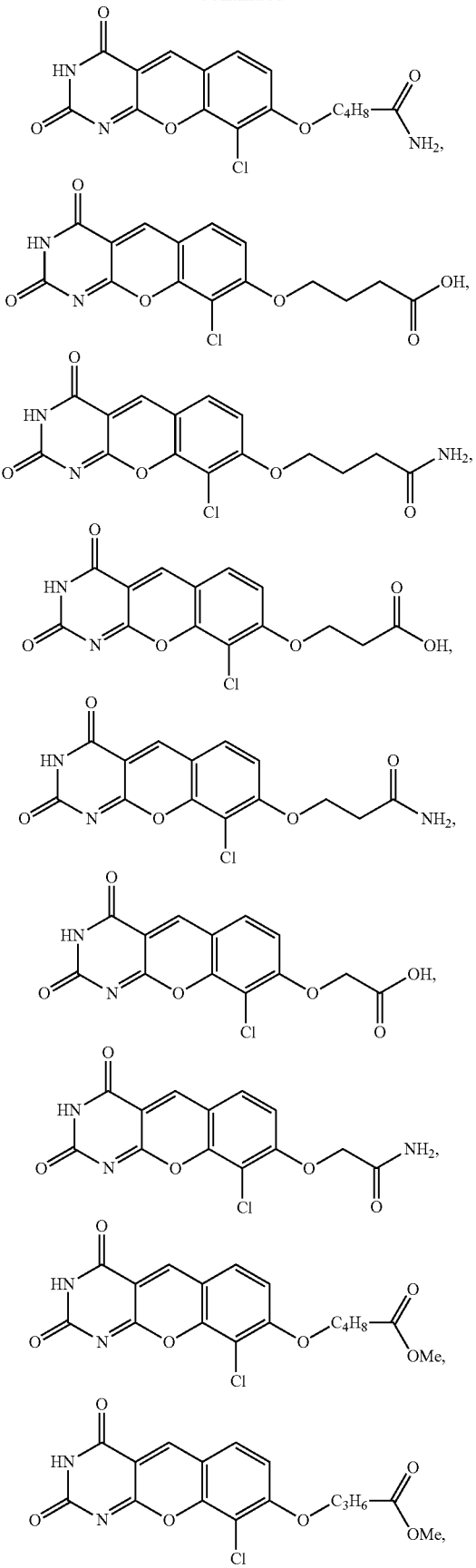

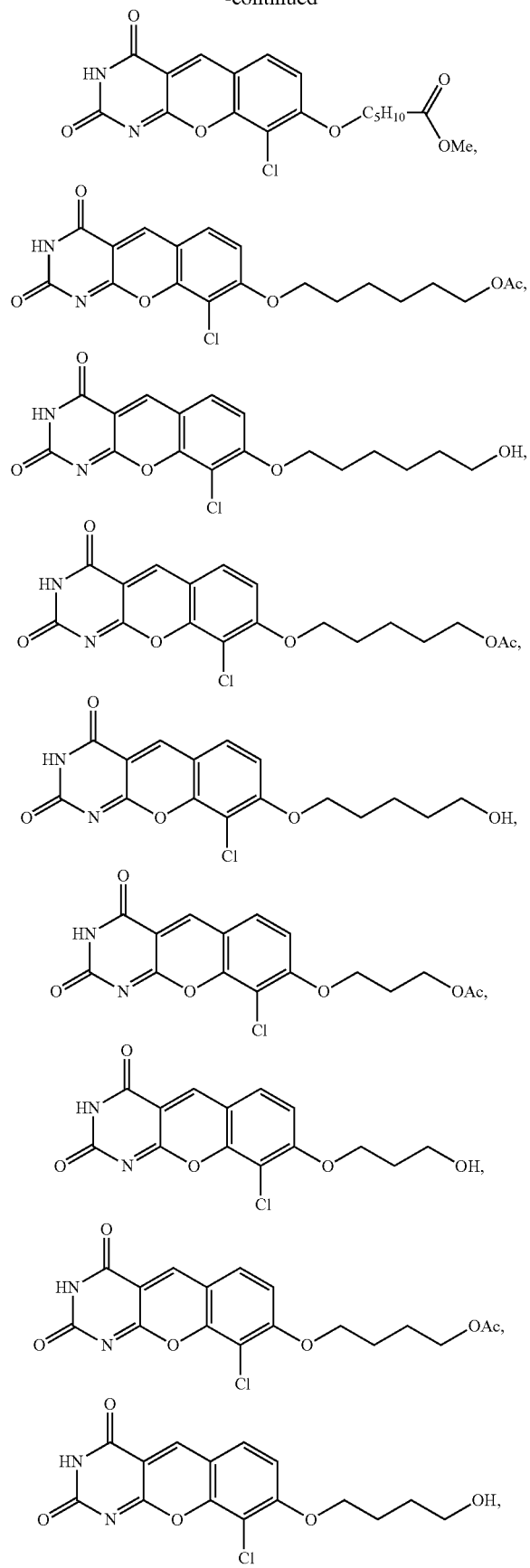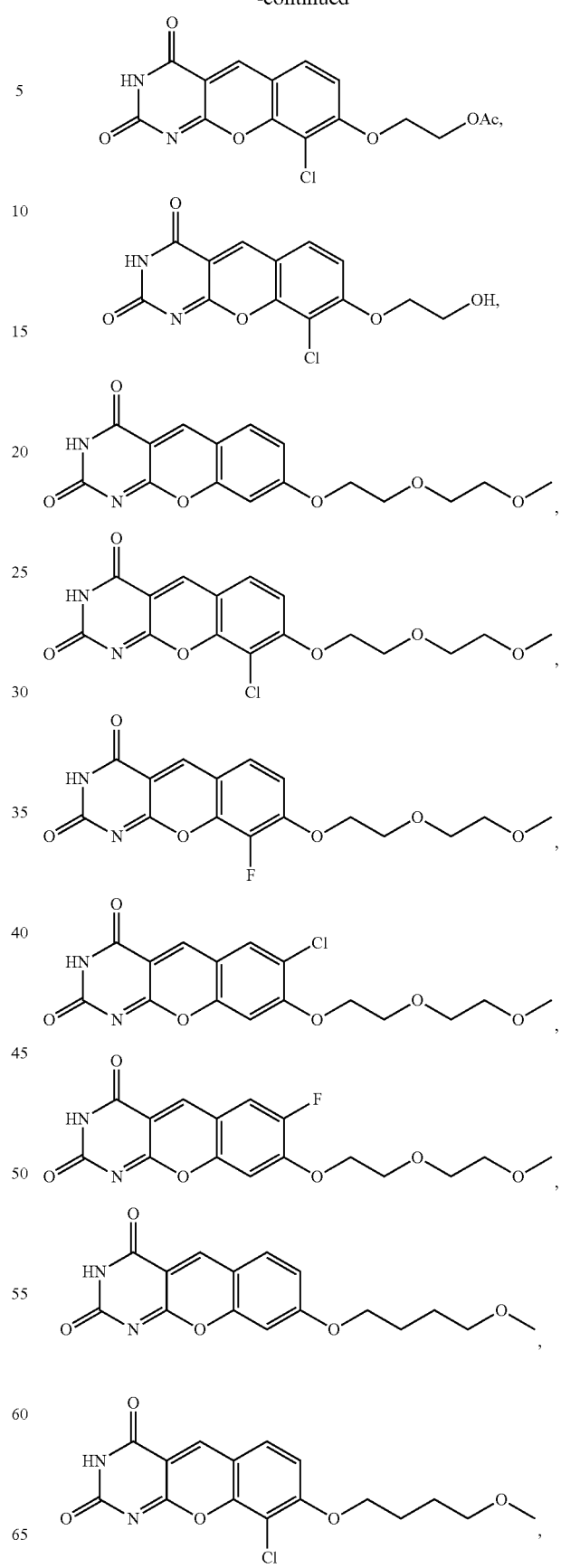

-continued

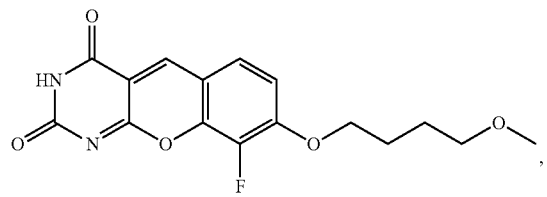

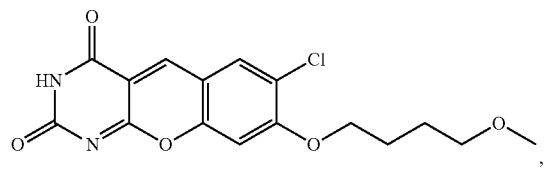

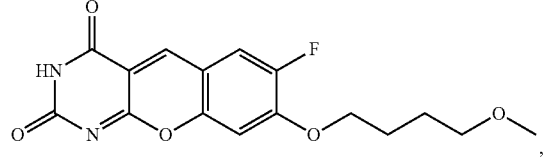

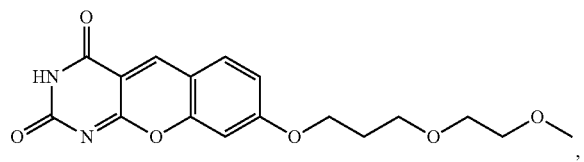

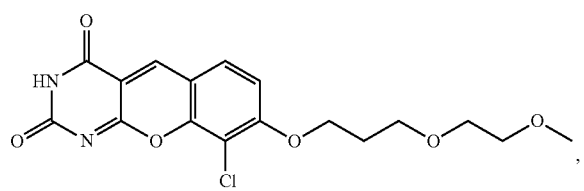

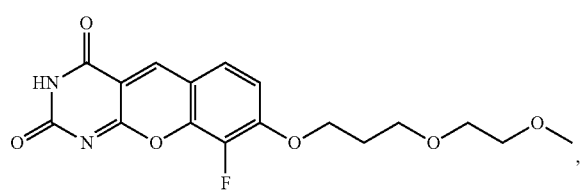

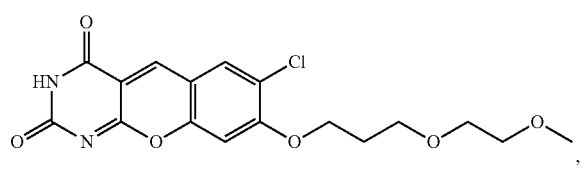

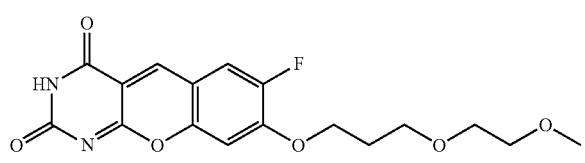

and crystalline forms, hydrates, or pharmaceutically acceptable salts thereof.

A further embodiment of the present invention is a compound. The compound is selected from the group consisting of:

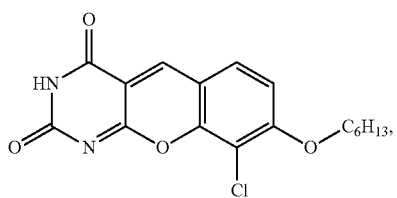

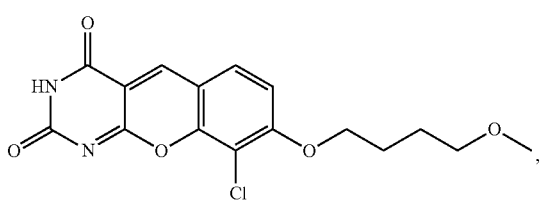

and crystalline forms, hydrates, or pharmaceutically acceptable salts thereof.

An additional embodiment of the present invention is a compound capable of inhibiting NF-κB. The compound has the structure of formula (I):

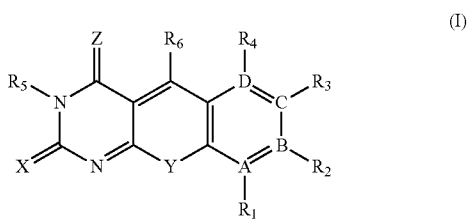

(I)

wherein:

A, B, C, and D are independently selected from the group consisting of carbon and nitrogen;

X, Y, and Z are independently selected from the group consisting of oxygen, sulfur, and $NR^a$;

$R_1$, $R_2$, $R_3$, and $R_4$ are independently selected from the group consisting of no atom, hydrogen, halogen, $C_{1-9}$ alkyl, $C_{1-9}$ alkenyl, $C_{1-9}$ alkynyl, aryl, $C_{1-9}$ heterocyclic, —OH, —$OR^a$, —$OR^aOR^b$, —$OR^aOR^bOR^c$, —O(C=O)$R^a$, —O(C=O)O$R^a$, —O(C=O)$NR^aR^b$, cyano, nitro, $CF_3$, $CHF_2$, $CH_2F$, —CHO, —COOH, —$COR^a$, —$COOR^a$, —$CONR^aR^b$, —CONHCON$R^aR^b$, —$NR^aR^b$, —$NHCOR^a$, —$NR^bCOR^a$, —CSOH, —$CSR^a$, —$CSOR^a$, —$CSNR^aR^b$, —$CSNHCSNR^aR^b$, —SH, —$SR^a$, —S(C=O)$R^a$, —S(C=O)O$R^a$, —S(C=O)$NR^aR^b$;

$R_5$ is selected from the group consisting of hydrogen, $C_{1-9}$ alkyl, $C_{1-9}$ alkenyl, $C_{1-9}$ alkynyl, aryl, $C_{1-9}$ heterocyclic, —$R^aCO$, —$R^aNHCO$, and —$R^aOCO$; and $R_6$, $R^a$, $R^b$, and $R^c$ are independently selected from the group consisting of hydrogen, hydroxyl, amine, $C_{1-9}$ alkyl, $C_{1-9}$ alkenyl, $C_{1-9}$ alkynyl, aryl, and $C_{1-9}$ heterocyclic, or is a crystalline form, hydrate, or pharmaceutically acceptable salt thereof.

A further embodiment of the present invention is a compound capable of inhibiting NF-κB. The compound is selected from the group consisting of:

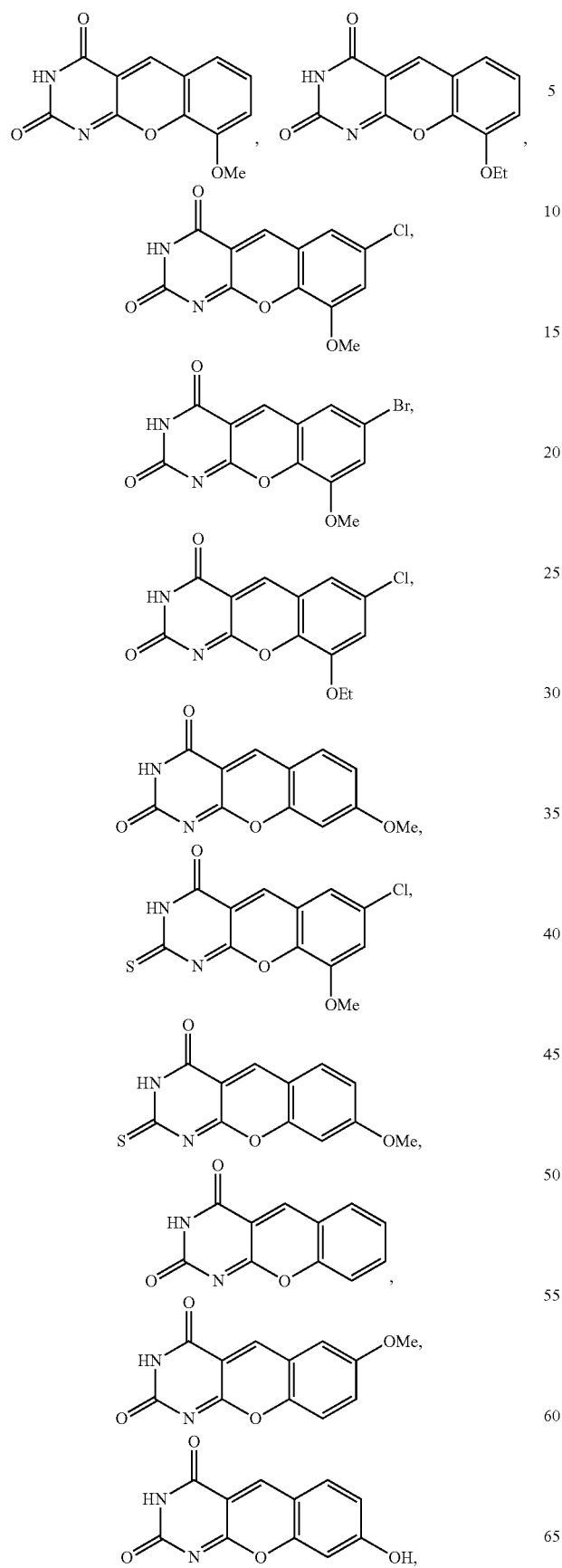
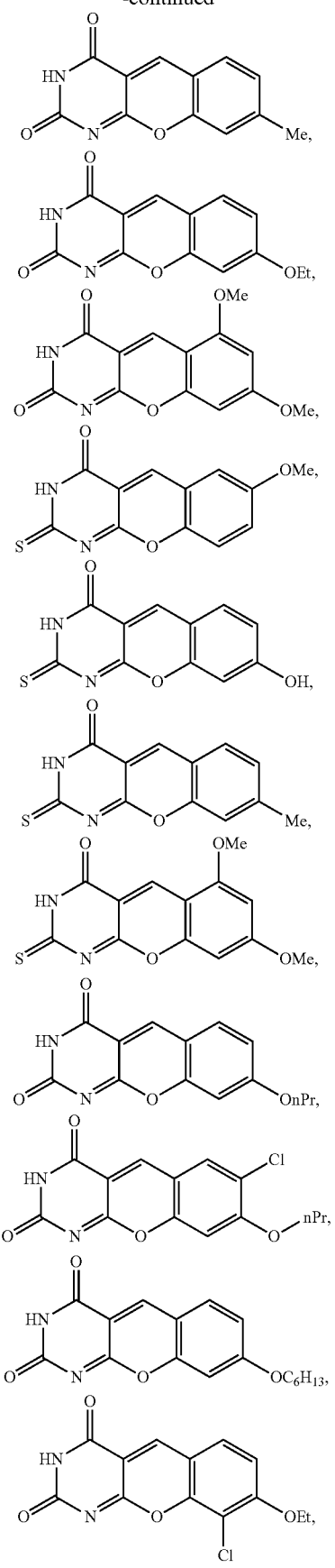

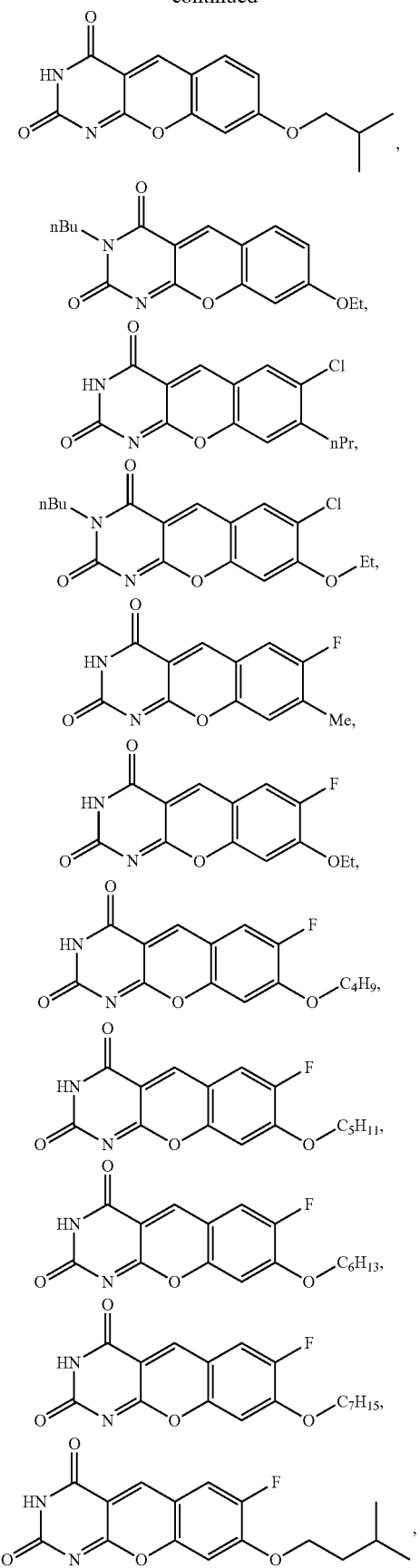
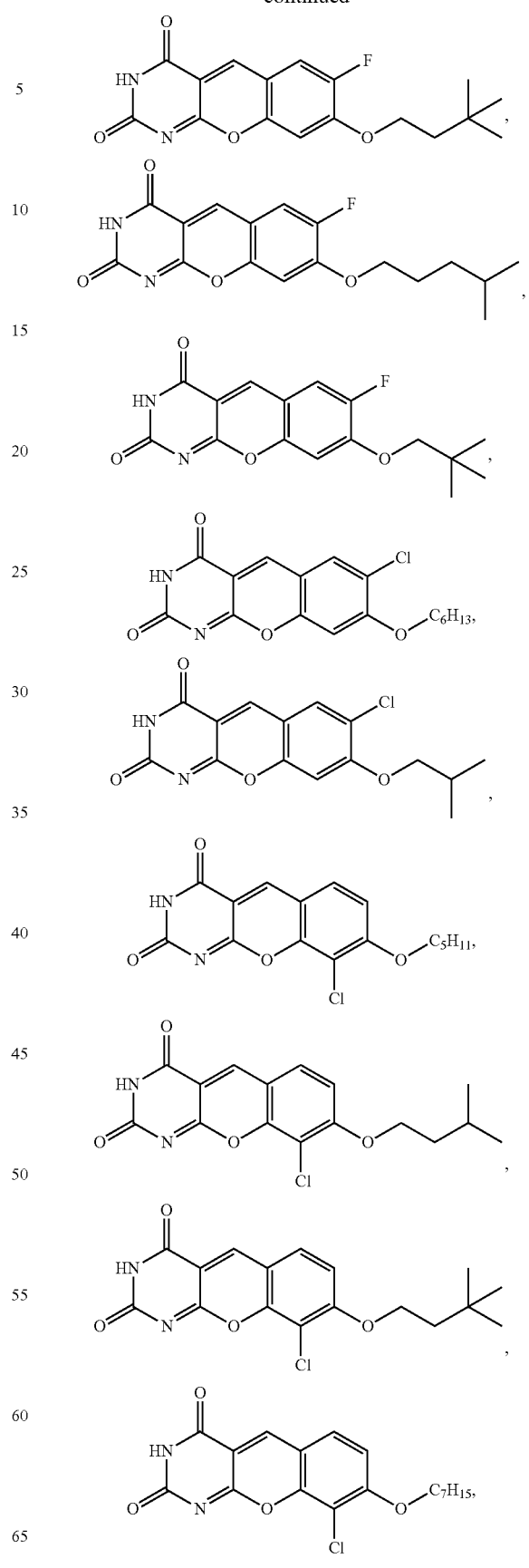

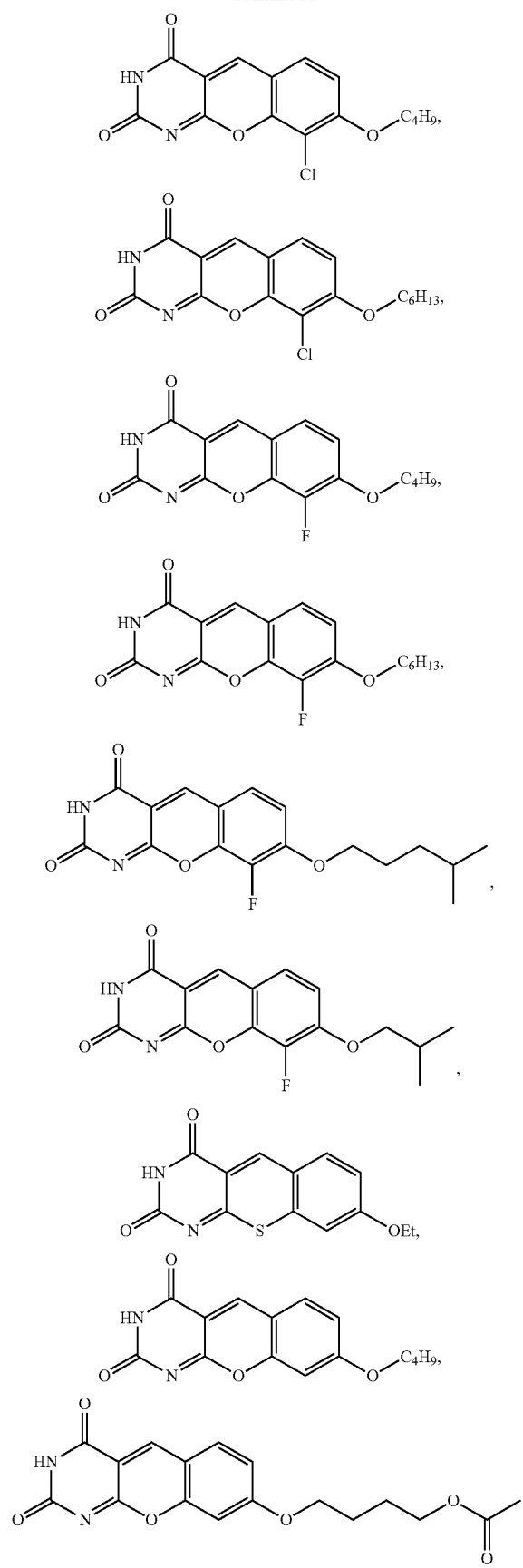

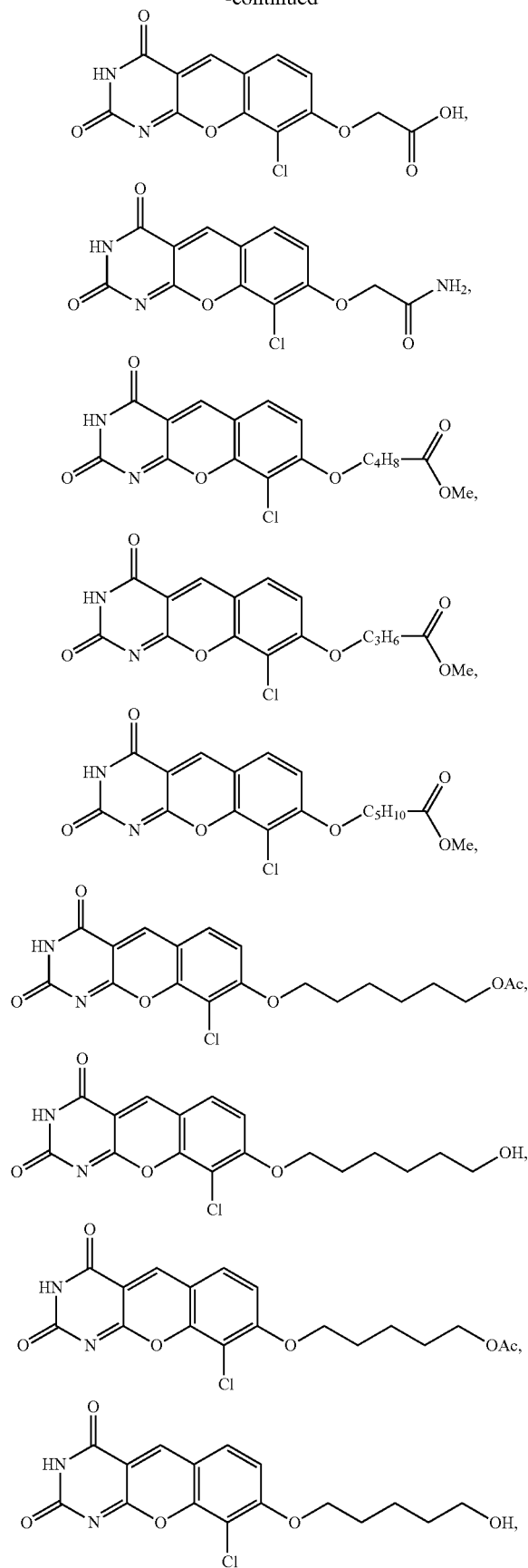
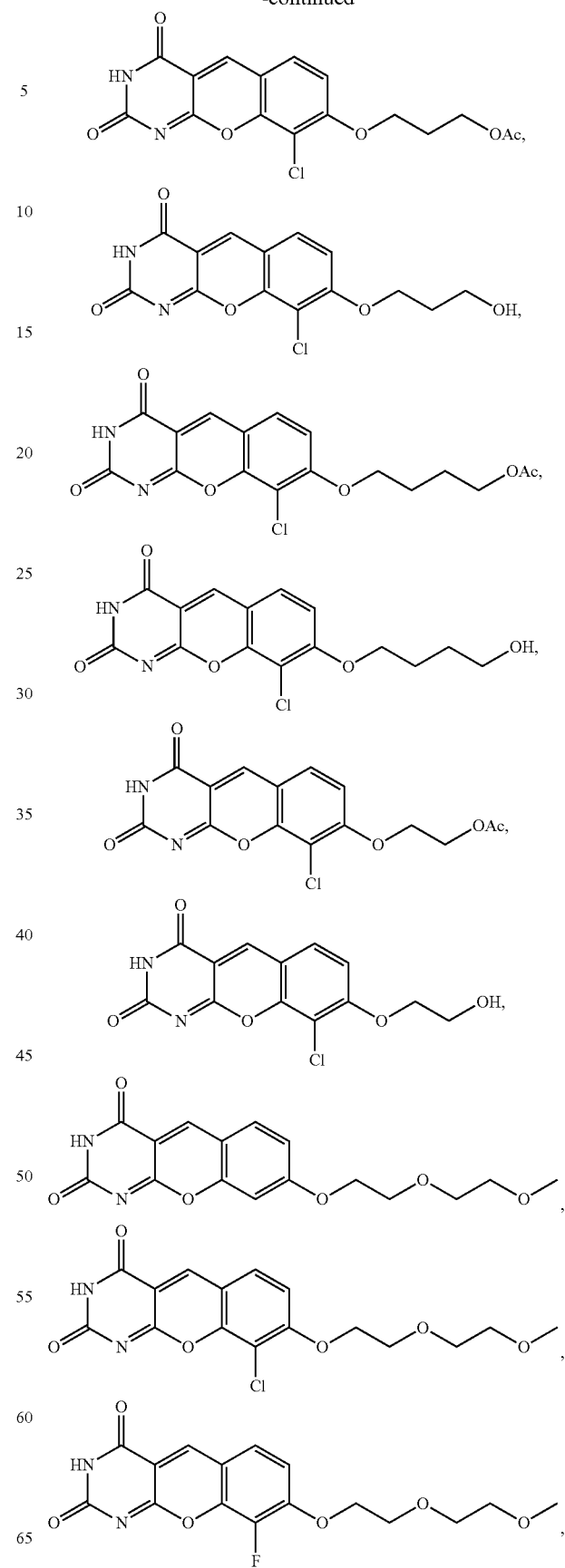

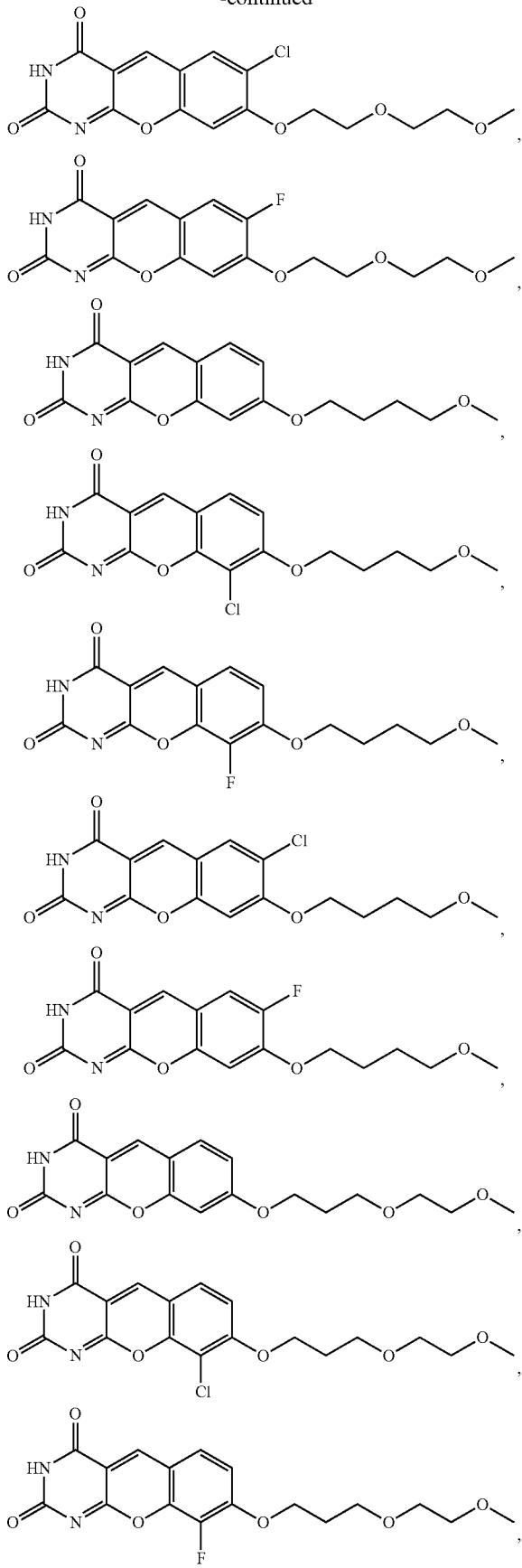

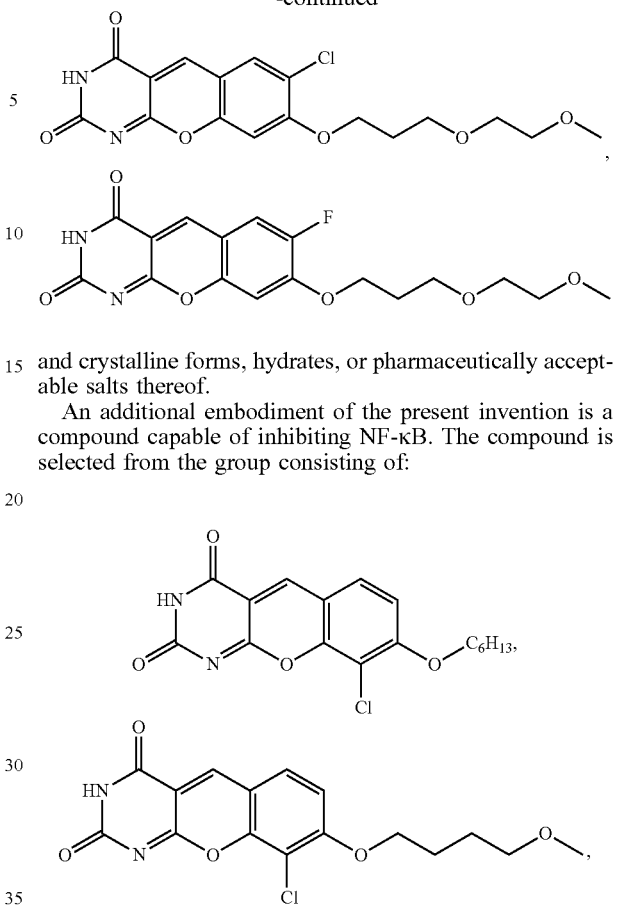

and crystalline forms, hydrates, or pharmaceutically acceptable salts thereof.

An additional embodiment of the present invention is a compound capable of inhibiting NF-κB. The compound is selected from the group consisting of:

and crystalline forms, hydrates, or pharmaceutically acceptable salts thereof.

Another embodiment of the present invention is a pharmaceutical composition. The pharmaceutical composition comprises a pharmaceutically acceptable carrier and any of the compounds disclosed herein.

A further embodiment of the present invention is a method of inhibiting NF-κB in a cell. The method comprises contacting the cell with any of the compounds disclosed herein.

BRIEF DESCRIPTION OF THE DRAWINGS

FIG. 3A is a table showing pharmacokinetic data for compound 13.

Figure 4A:
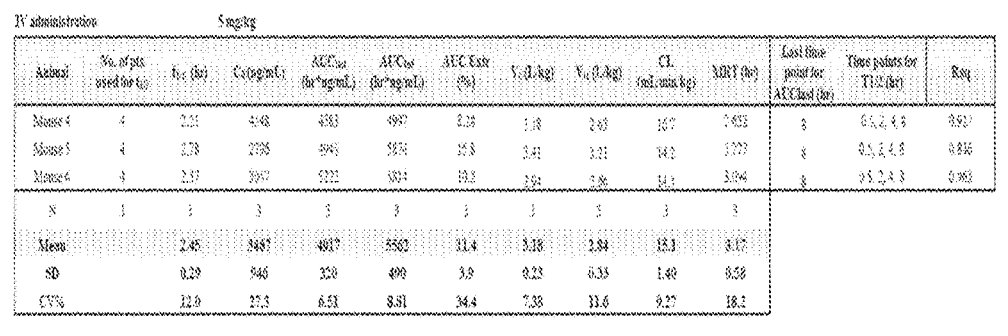

FIG. 4A is a table showing pharmacokinetic data for compound 20.

Figure 5A:
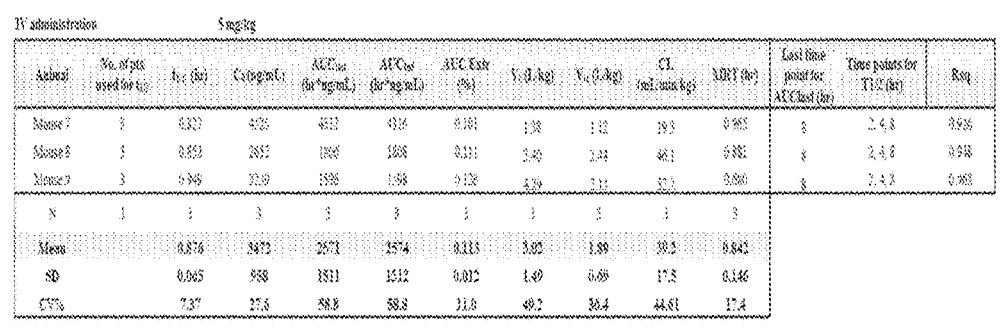

FIG. 5A is a table showing pharmacokinetic data for compound 26.

Figure 6A:
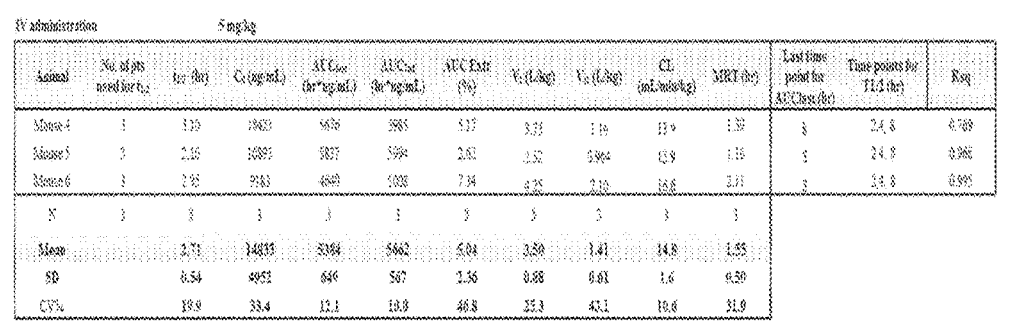

FIG. 6A is a table showing pharmacokinetic data for compound 42.

FIG. 7A is a table showing pharmacokinetic data for compound 44.

Figure 8A:
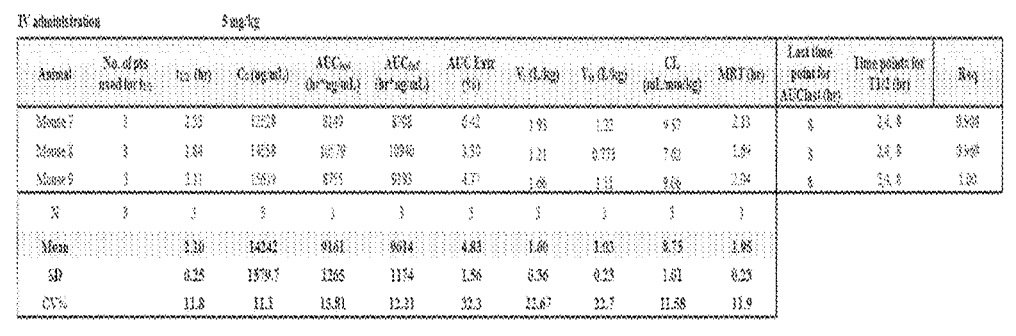

FIG. 8A is a table showing pharmacokinetic data for compound 46.

DETAILED DESCRIPTION OF THE INVENTION

Figures 1A, 1B, 1C, 1D:
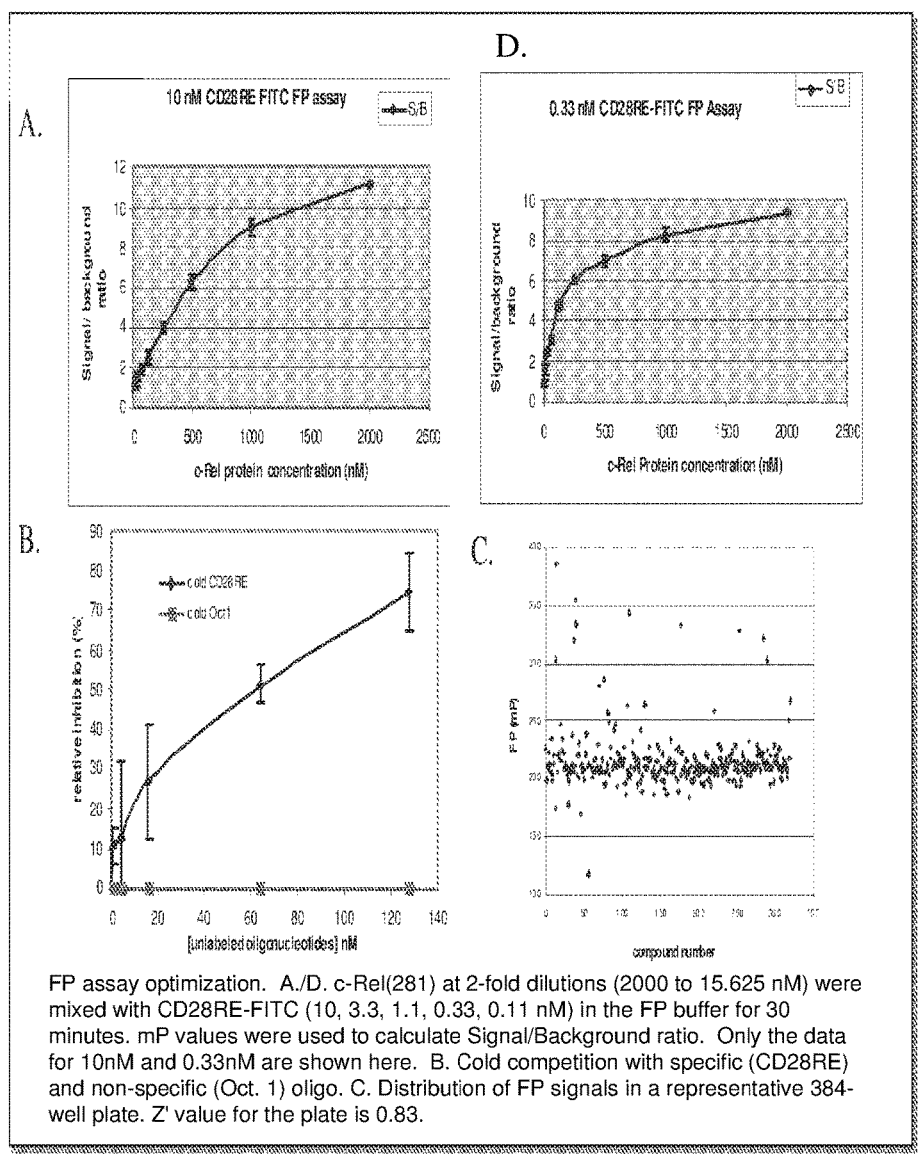
FIG. 1A shows a line graph of results from 10 nM CD28RE FITC fluorescence polarization assays.
FIG. 1B shows a line graph of cold competition with specific (CD28RE) and non-specific (Oct1) oligo.
FIG. 1C is a dot plot showing distribution of fluorescence polarization signals in a representative 384-well plate.
FIG. 1D shows a line graph of results from 0.33 nM CD28RE FITC fluorescence polarization assays.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The term "about" generally indicates within ±0.5%, 1%, 2%, 5%, or up to ±10% of the indicated value. For example, an amount of "about 10 wt %" generally indicates, in its broadest sense, 10 wt %±10%, which indicates 9.0-11.0 wt %. The term "about" may alternatively indicate a variation or average in a physical characteristic of a group.

One embodiment of the present invention is a compound. The compound has the structure of formula (I):

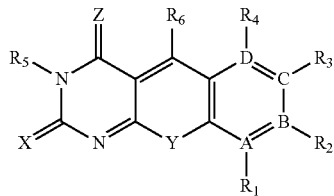

(I)

wherein:
A, B, C, and D are independently selected from the group consisting of carbon and nitrogen;
X, Y, and Z are independently selected from the group consisting of oxygen, sulfur, and $NR^a$;
$R_1$, $R_2$, $R_3$, and $R_4$ are independently selected from the group consisting of no atom, hydrogen, halogen, $C_{1-9}$ alkyl, $C_{1-9}$ alkenyl, $C_{1-9}$ alkynyl, aryl, $C_{1-9}$ heterocyclic, —OH, —$OR^a$, —$OR^aOR^b$, —$OR^aOR^bOR^c$, —$OR^a(C$=$O)R^b$, —$O(C$=$O)R^a$, —$O(C$=$O)OR^a$, —$O(C$=$O)NR^aR^b$, cyano, nitro, —$CF_3$, —$CHF_2$, —$CH_2F$, —CHO, —COOH, —$COR^a$, —$COOR^a$, —$CONR^aR^b$, —$CONHCONR^aR^b$, —$NR^aR^b$, —$NHCOR^a$, —$NR^bCOR^a$, —CSOH, —$CSR^a$, —$CSOR^a$, —$CSNR^aR^b$, —$CSNHCSNR^aR^b$, —SH, —$SR^a$, —$S(C$=$O)R^a$, —$S(C$=$O)OR^a$, —$S(C$=$O)NR^aR^b$;

$R_5$ is selected from the group consisting of hydrogen, $C_{1-9}$ alkyl, $C_{1-9}$ alkenyl, $C_{1-9}$ alkynyl, aryl, $C_{1-9}$ heterocyclic, —$R^aCO$, —$R^aNHCO$, and —$R^aOCO$; and
$R_6$, $R^a$, $R^b$, and $R^c$ are independently selected from the group consisting of hydrogen, hydroxyl, amine, $C_{1-9}$ alkyl, $C_{1-9}$ alkenyl, $C_{1-9}$ alkynyl, aryl, and $C_{1-9}$ heterocyclic,
or is a crystalline form, hydrate, or pharmaceutically acceptable salt thereof.

As used herein, the term "compound" refers to two or more atoms that are connected by one or more chemical bonds. In the present invention, "chemical bonds" and "bonds" are interchangeable and include, but are not limited to, covalent bonds, ionic bonds, hydrogen bonds, and van der Waals interactions. Covalent bonds of the present invention include single, double, and triple bonds. Compounds of the present invention include, but are not limited to, organic molecules. Atoms that comprise the compounds of the present invention are "linked" if they are connected by a chemical bond of the present invention.

Organic compounds of the present invention include linear, branched, and cyclic hydrocarbons with or without functional groups. The term "$C_{x-y}$" when used in conjunction with a chemical moiety, such as, alkyl, alkenyl, alkynyl or alkoxy is meant to include groups that contain from x to y carbons in the chain. For example, the term "$C_{x-y}$ alkyl" means substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_{x-y}$ alkenyl" and "$C_{x-y}$ alkynyl" refer to substituted or unsubstituted unsaturated aliphatic groups analogous in length and possible substitution to the alkyls described above, but containing at least one double or triple bond respectively.

The term "independently selected" and grammatical variations thereof mean that, in a chemical structure of the present invention, (e.g., formula I), if more than one atom in the structure can be selected from a list of elements, those atoms may or may not be of the same element. Similarly, if more than one chemical moiety in the structure can be selected from a list of chemical moieties, those moieties may or may not be the same.

In one aspect of this embodiment,
X, Y, and Z are independently selected from the group consisting of oxygen and sulfur;
$R_1$ is selected from the group consisting of —H, —F, —Cl, —OMe, and —OEt;
$R_2$ is selected from the group consisting of —H, —$CH_3$, —OH, —OMe, —OEt, -Me, -Et, -nPr, —O-nPr, —OEtnPr, —$OC_4H_9$, —$OC_5H_{11}$, —$OC_6H_{13}$, —$OC_7H_{15}$, —O-isobutyl, —O-isopentyl, —$OC_nH_{2n}OMe$, —$OC_nH_{2n}OC_mH_{2m}OMe$, —$OC_nH_{2n}OH$, —$OC_nH_{2n}OC_mH_{2m}OH$, $OC_nH_{2n}OEt$, —$OC_nH_{2n}OC_mH_{2m}OEt$, —O—$C_nH_{2n}COOH$, —O—$C_nH_{2n}CONH2$, —O—$C_nH_{2n}CONHMe$,

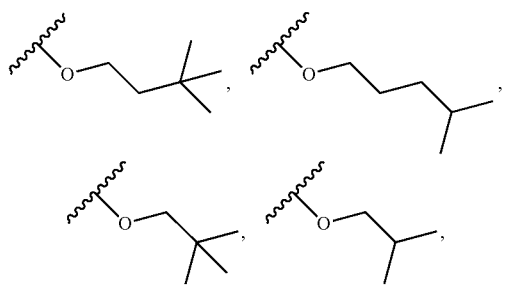

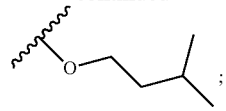

$R_3$ is selected from the group consisting of —H, —Cl, —Br, —F, and —OMe;
$R_4$ is selected from the group consisting of —H and —OMe;
$R_5$ is selected from the group consisting of —H, -Me, -Et, —Pr, -iPr, -Ph, iBu and -nBu;
$R_6$ is selected from the group consisting of —H and —CH$_3$;
m is 2, 3, 4 or 5; and, n is 2, 3, 4, or 5.

In another aspect of this embodiment,
X, Y, and Z are independently selected from the group consisting of oxygen and sulfur; and
$R_6$ is hydrogen.

Preferably,
Z is oxygen;
$R_1$ and $R_3$ are selected from the group consisting of hydrogen, halogen, —CN, and —CF$_3$;
$R_2$ is selected from the group consisting of C$_{1-9}$ alkoxy, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, OC$_n$H$_{2n}$OEt, —OC$_n$H$_{2n}$OC$_m$H$_{2m}$OEt, —O—C$_n$H$_{2n}$COOH, —O—C$_n$H$_{2n}$CONH2, —O—C$_n$H$_{2n}$CONHMe, and —OH;
$R_4$ is selected from the group consisting of hydrogen, C$_{1-9}$ alkoxy and —OH;
m is 2, 3, 4 or 5; and n is 2, 3, 4, or 5.

More preferably,
X and Y are oxygen; and
$R_4$ is hydrogen.

In an exemplary aspect of this embodiment, the compound is selected from the group consisting of:

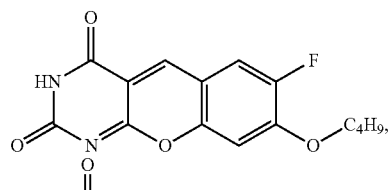

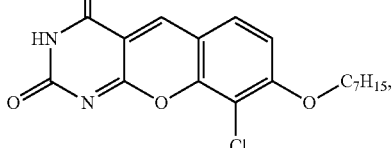

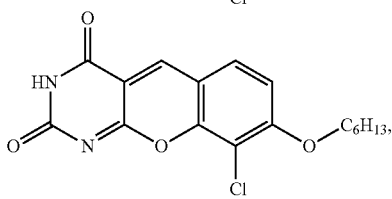

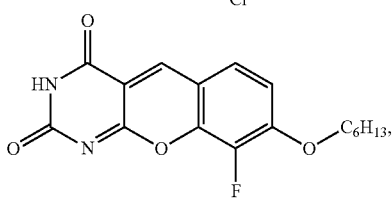

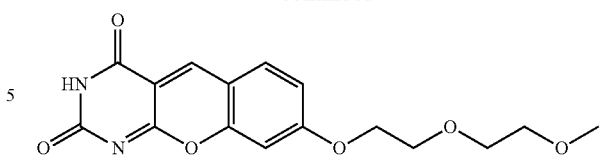

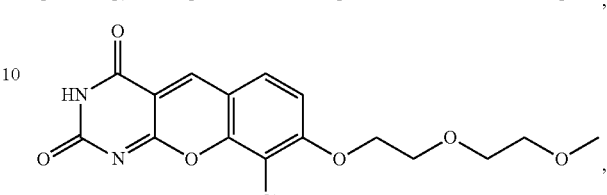

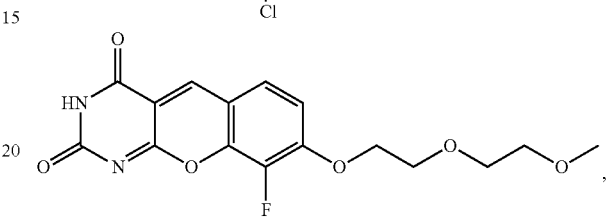

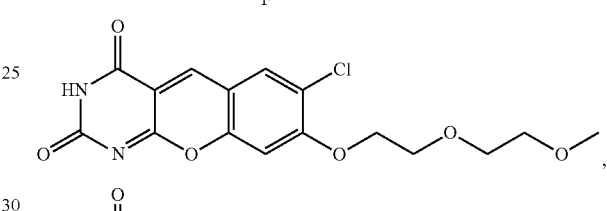

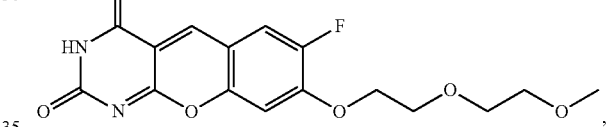

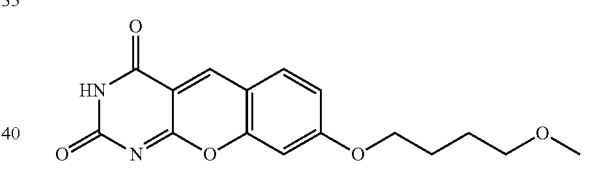

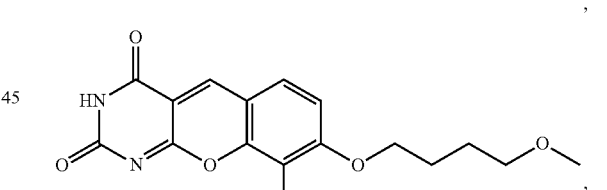

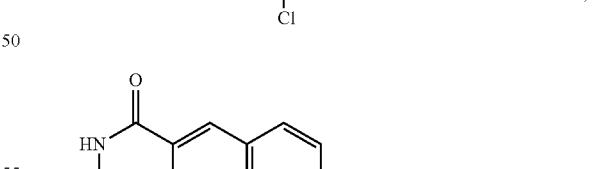

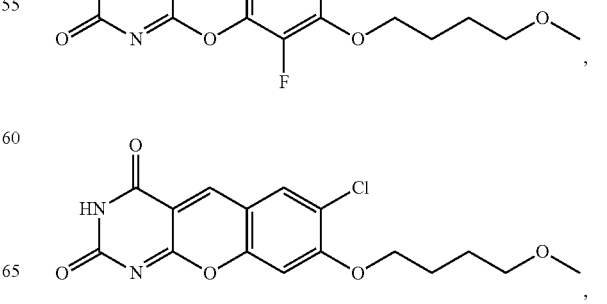

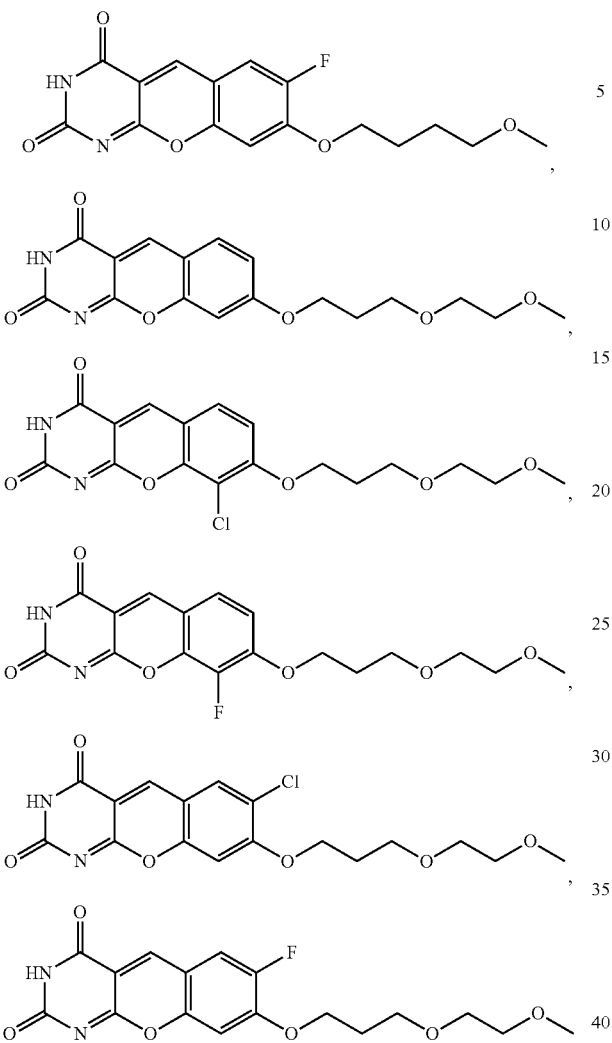

and crystalline forms, hydrates, or pharmaceutically acceptable salts thereof.

In an additional aspect of this embodiment, $R_1$ and $R_2$ are linked by at least one bond.

In a further aspect of this embodiment, $R_2$ and $R_3$ are linked by at least one bond.

The compound according to claim 1, wherein $R_3$ and $R_4$ are linked by at least one bond.

Another embodiment of the present invention is a compound. The compound is selected from the group consisting of:

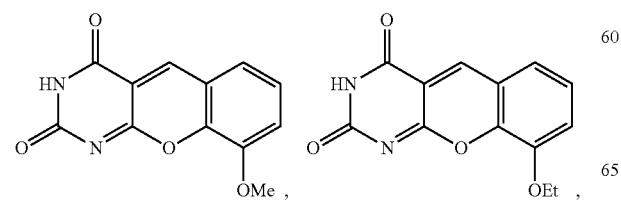

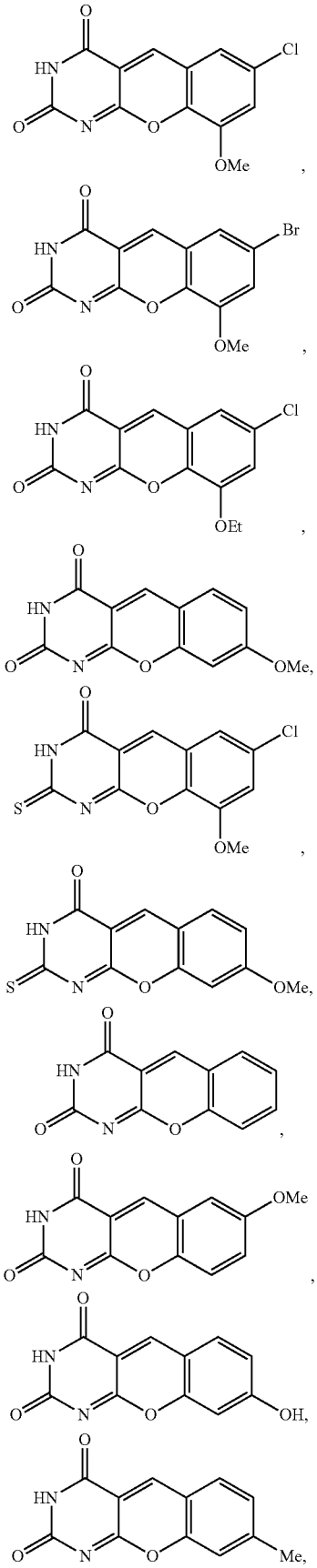

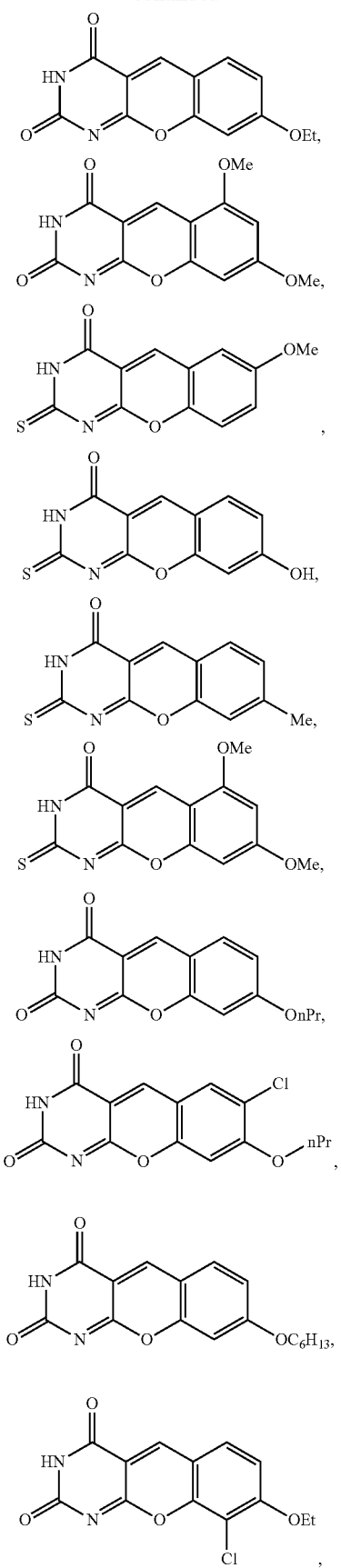
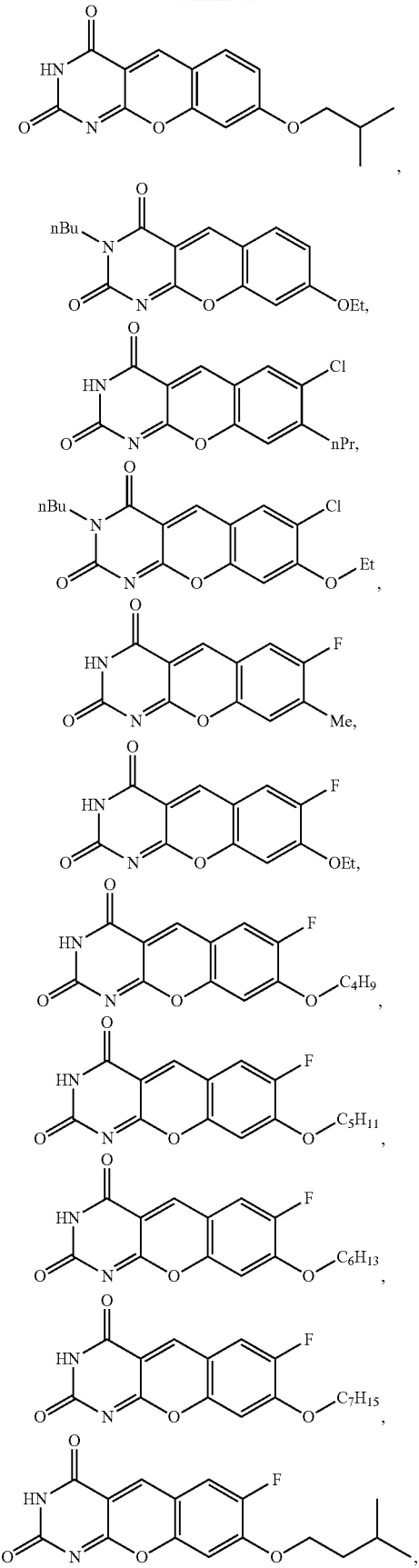

-continued
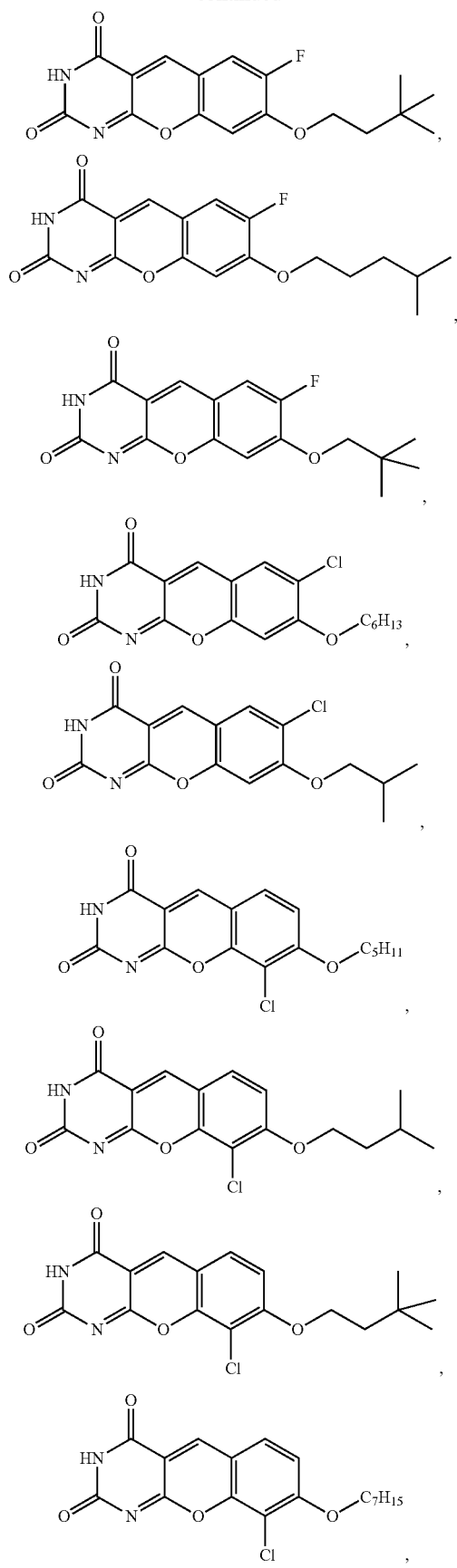
-continued
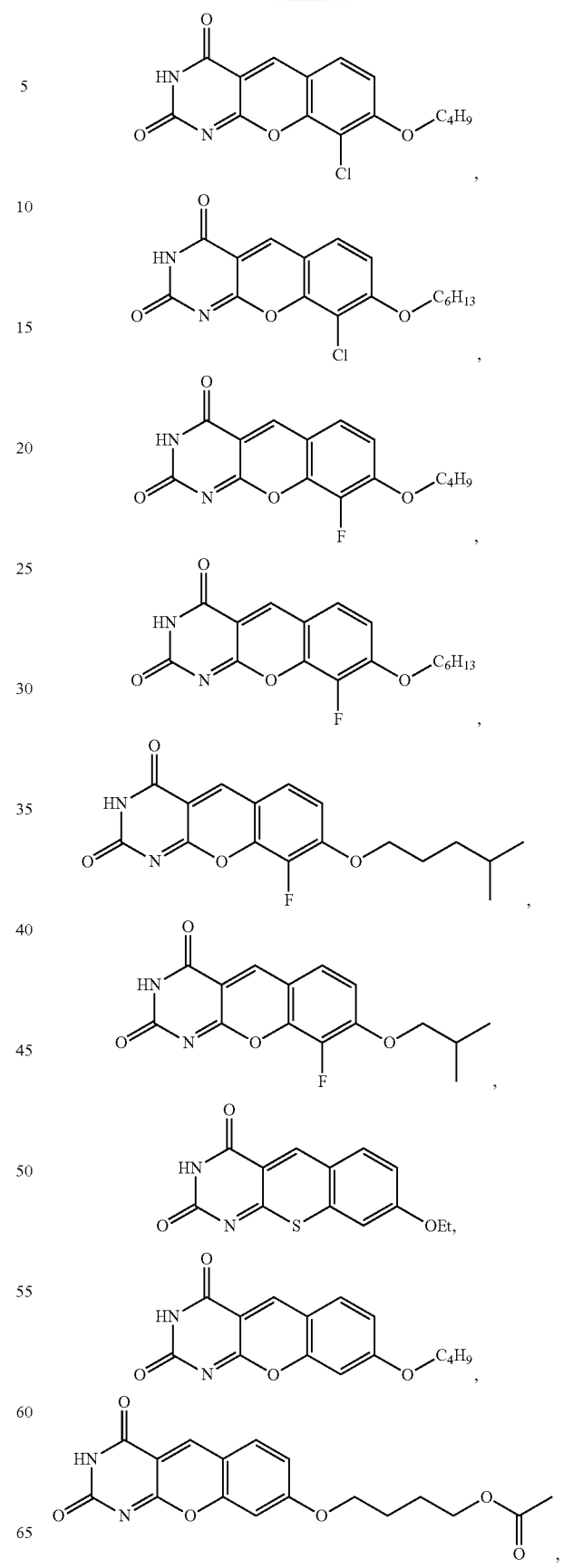

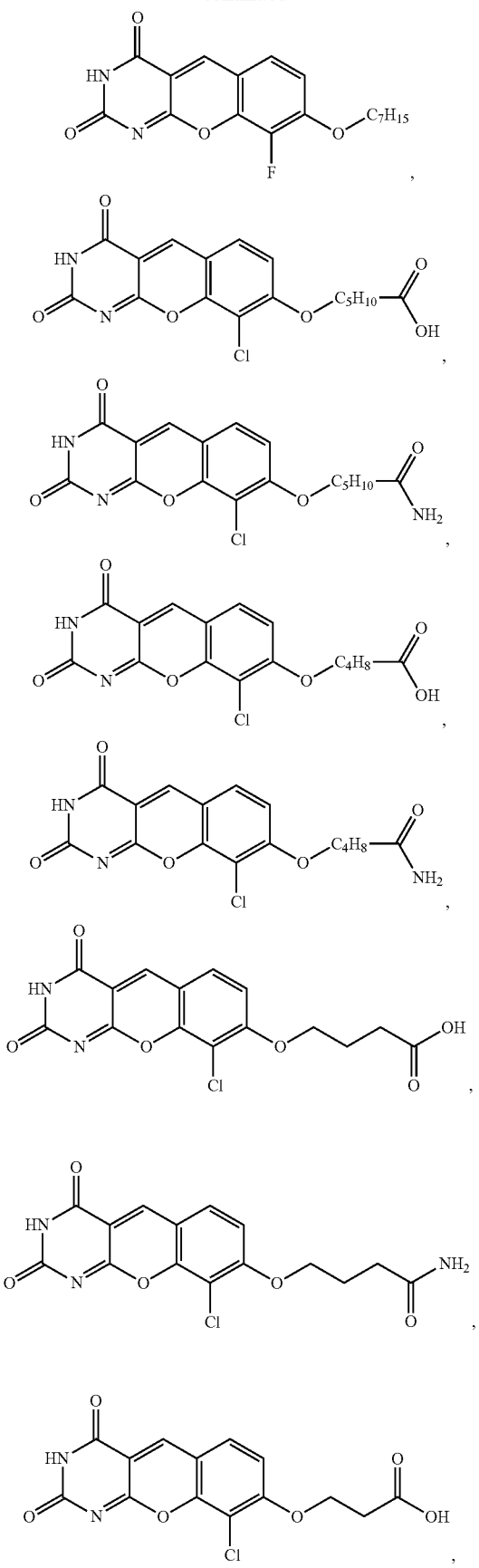
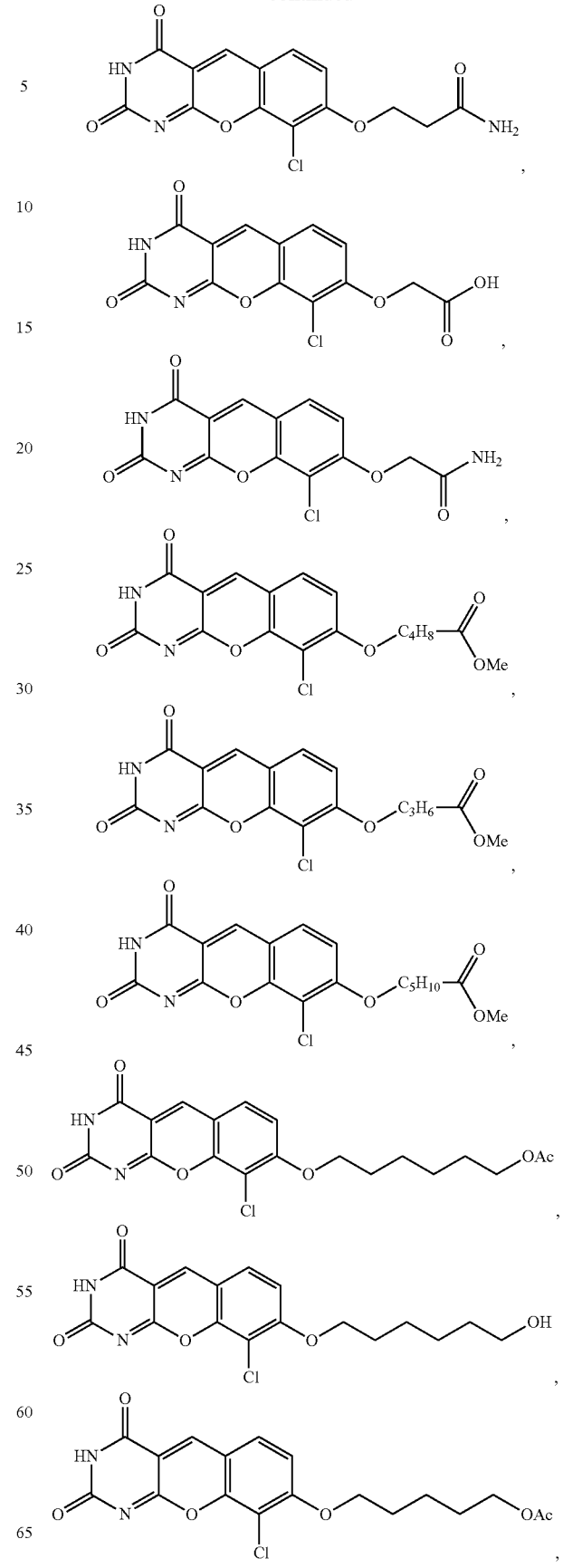

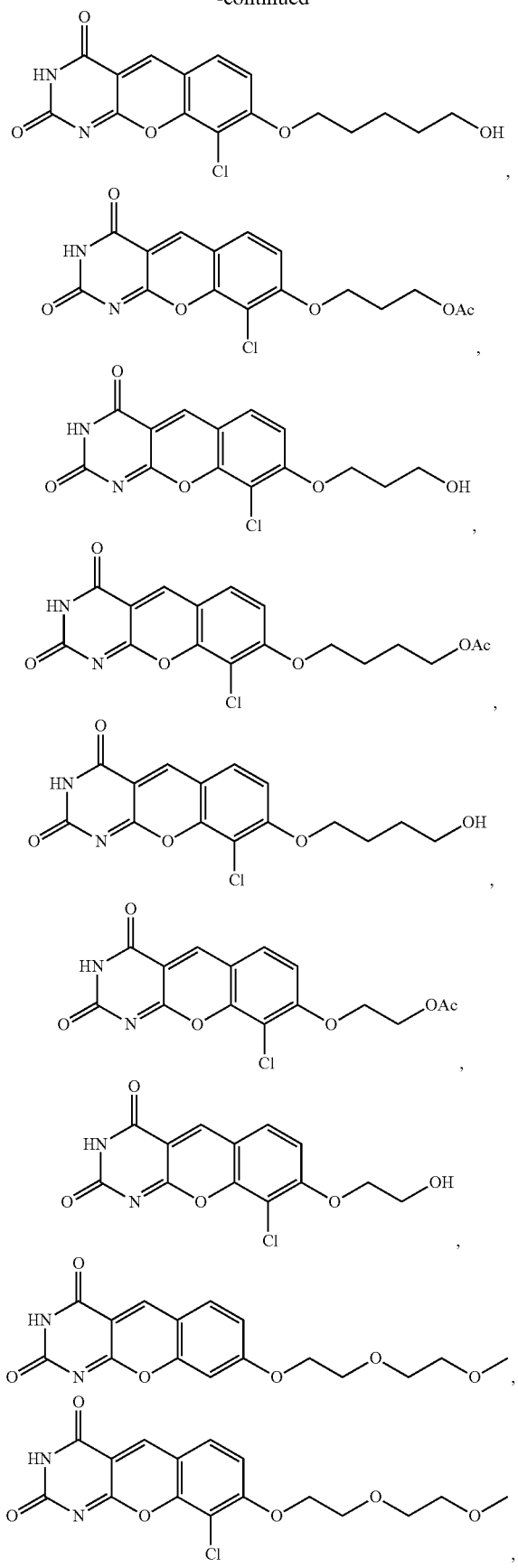
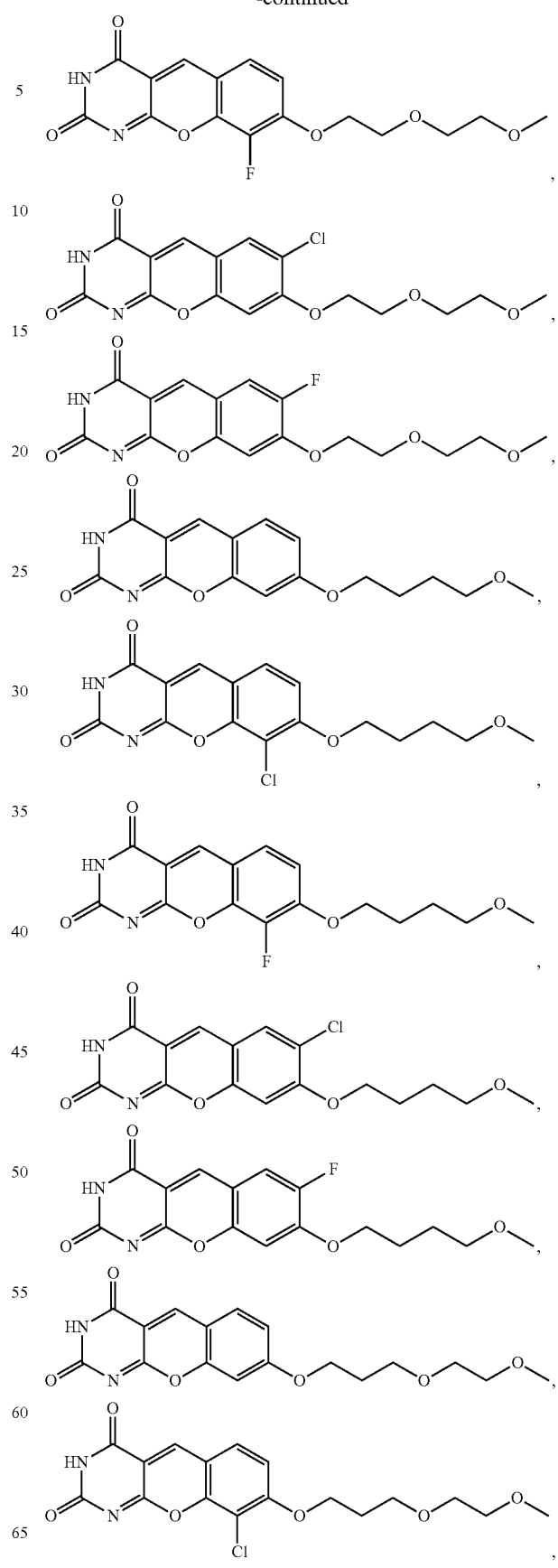

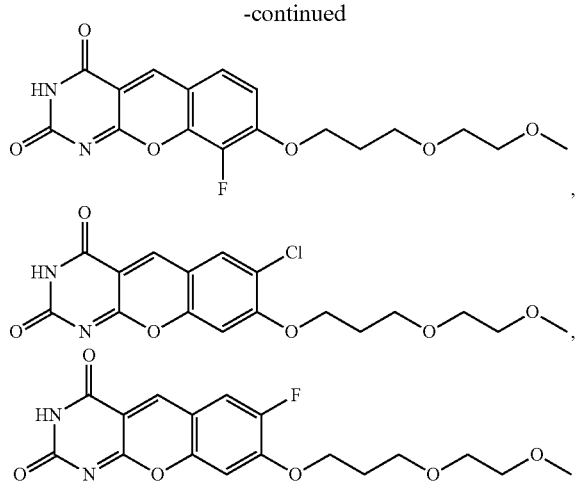

and crystalline forms, hydrates, or pharmaceutically acceptable salts thereof.

A further embodiment of the present invention is a compound. The compound is selected from the group consisting of:

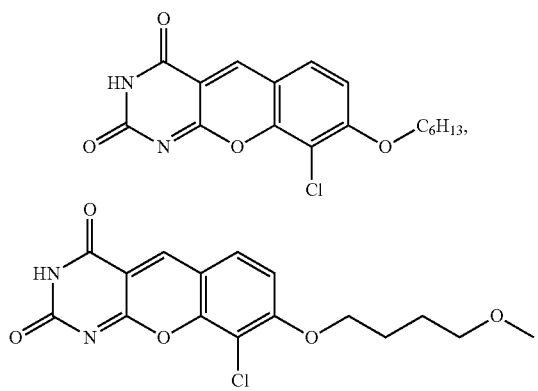

and crystalline forms, hydrates, or pharmaceutically acceptable salts thereof.

An additional embodiment of the present invention is a compound capable of inhibiting NF-κB. The compound has the structure of formula (I):

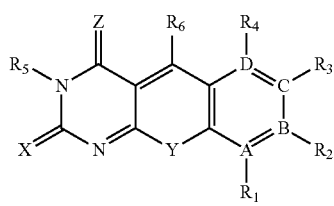

wherein:
A, B, C, and D are independently selected from the group consisting of carbon and nitrogen;
X, Y, and Z are independently selected from the group consisting of oxygen, sulfur, and $NR^a$;
$R_1$, $R_2$, $R_3$, and $R_4$ are independently selected from the group consisting of no atom, hydrogen, halogen, $C_{1-9}$ alkyl, $C_{1-9}$ alkenyl, $C_{1-9}$ alkynyl, aryl, $C_{1-9}$ heterocyclic, —OH, —$OR^a$, —$OR^aOR^b$, —$OR^aOR^bOR^c$, —O(C=O)$R^a$, —O(C=O)$OR^a$, —O(C=O)$NR^aR^b$, cyano, nitro, $CF_3$, $CHF_2$, $CH_2F$, —CHO, —COOH, —$COR^a$, —$COOR^a$, —$CONR^aR^b$, —$CONHCONR^aR^b$, —$NR^aR^b$, —$NHCOR^a$, —$NR^bCOR^a$, —CSOH, —$CSR^a$, —$CSOR^a$, —$CSNR^aR^b$, —CSNHCSN-$R^aR^b$, —SH, —$SR^a$, —S(C=O)$R^a$, —S(C=O)$OR^a$, —S(C=O)$NR^aR^b$;

$R_5$ is selected from the group consisting of hydrogen, $C_{1-9}$ alkyl, $C_{1-9}$ alkenyl, $C_{1-9}$ alkynyl, aryl, $C_{1-9}$ heterocyclic, —$R^aCO$, —$R^aNHCO$, and —$R^aOCO$; and $R_6$, $R^a$, $R^b$, and $R^c$ are independently selected from the group consisting of hydrogen, hydroxyl, amine, $C_{1-9}$ alkyl, $C_{1-9}$ alkenyl, $C_{1-9}$ alkynyl, aryl, and $C_{1-9}$ heterocyclic,
or is a crystalline form, hydrate, or pharmaceutically acceptable salt thereof.

In the present invention, the compound capable of inhibiting NF-κB may function as a direct or indirect NF-κB/Rel inhibitor. A direct NF-κB/Rel inhibitor is a compound that binds to or interacts with NF-κB/Rel directly and inhibits its DNA binding and transcriptional function. An indirect NF-κB/Rel inhibitor is a compound that binds to or interacts with a compound other than NF-κB/Rel, thereby generating a downstream inhibitory effect on NF-κB/Rel activity.

In one aspect of this embodiment,
X, Y, and Z are independently selected from the group consisting of oxygen and sulfur;
$R_1$ is selected from the group consisting of —H, —F, —Cl, —OMe, and —OEt;
$R_2$ is selected from the group consisting of —H, —$CH_3$, —OH, —OMe, —OEt, -Et, -nPr, —O-nPr, —OEtnPr, —$OC_4H_9$, —$OC_5H_{11}$, —$OC_6H_{13}$, —$OC_7H_{15}$, —O-isobutyl, —O-isopentyl, —$OC_nH_{2n}OMe$, —$OC_nH_{2n}OC_mH_{2m}OMe$, —$OC_nH_{2n}OH$, —$OC_nH_{2n}OC_mH_{2m}OH$, $OC_nH_{2n}OEt$, —$OC_nH_{2n}OC_mH_{2m}OEt$, —O—$C_nH_{2n}COOH$, —O—$C_nH_{2n}CONH2$, —O—$C_nH_{2n}CONHMe$,

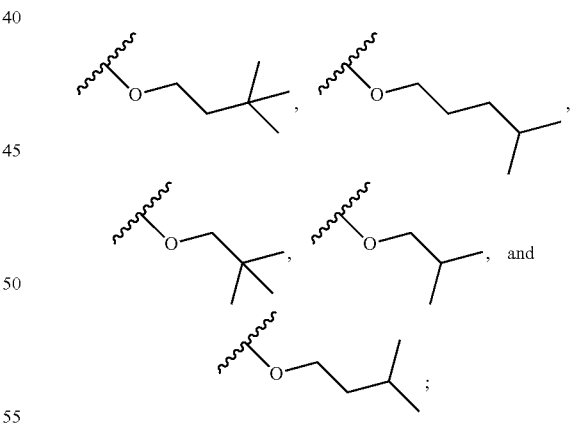

$R_3$ is selected from the group consisting of —H, —Cl, —Br, —F, and —OMe;
$R_4$ is selected from the group consisting of —H and —OMe;
$R_5$ is selected from the group consisting of —H, -Me, and -nBu;
$R_6$ is selected from the group consisting of —H and —$CH_3$;
m is 2, 3, 4 or 5; and n is 2, 3, 4, or 5.

In another aspect of this embodiment,
X, Y, and Z are independently selected from the group consisting of oxygen and sulfur; and
$R_6$ is hydrogen.

Preferably,
Z is oxygen;
$R_1$ and $R_3$ are selected from the group consisting of hydrogen, halogen, —CN, and —$CF_3$;
$R_2$ is selected from the group consisting of $C_{1-9}$ alkoxy, —$OC_nH_{2n}OMe$, —$OC_nH_{2n}OC_mH_{2m}OMe$, —$OC_nH_{2n}OH$, —$OC_nH_{2n}OC_mH_{2m}OH$, —$OC_nH_{2n}OEt$, —$OC_nH_{2n}OC_mH_{2m}OEt$, and —OH;
$R_4$ is selected from the group consisting of hydrogen, $C_{1-9}$ alkoxy and —OH;
m is 2, 3, 4 or 5; and n is 2, 3, 4, or 5.

More preferably,
X and Y are oxygen; and
$R_4$ is hydrogen.

In an exemplary aspect of this embodiment, the compound is selected from the group consisting of:

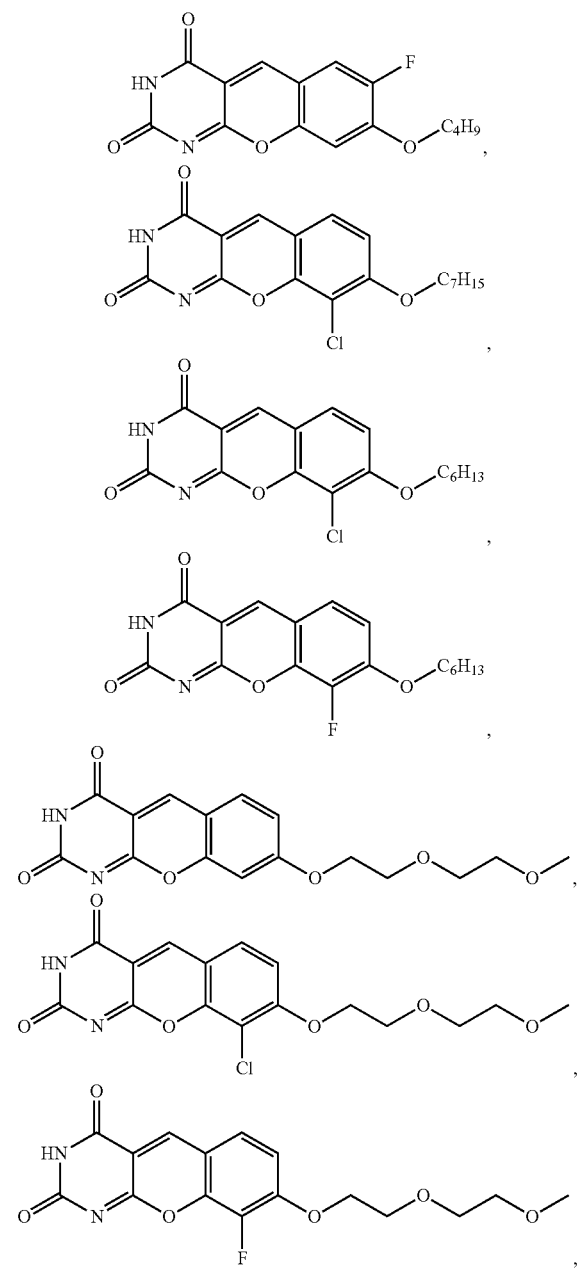

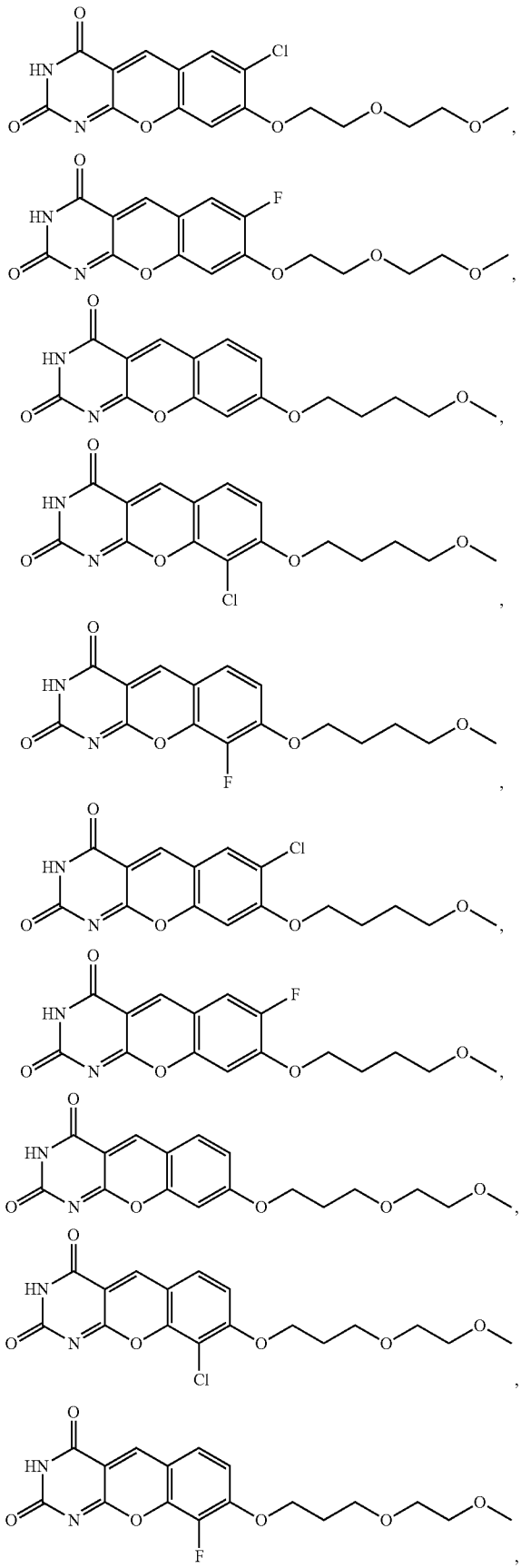

-continued

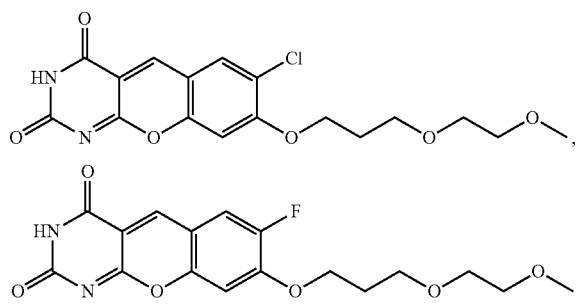

and crystalline forms, hydrates, or pharmaceutically acceptable salts thereof.

In an additional aspect of this embodiment, $R_1$ and $R_2$ are linked by at least one bond.

In a further aspect of this embodiment, $R_2$ and $R_3$ are linked by a bond.

In another aspect of this embodiment, $R_3$ and $R_4$ are linked by a bond.

A further embodiment of the present invention is a compound capable of inhibiting NF-κB. The compound is selected from the group consisting of:

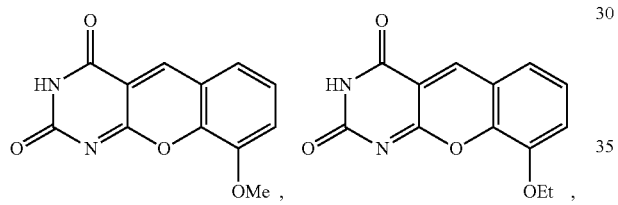

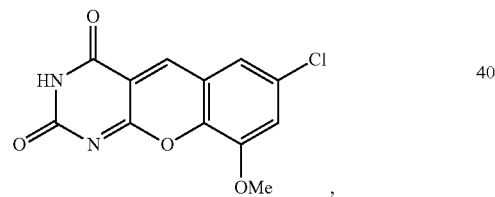

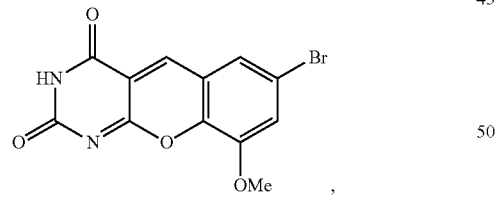

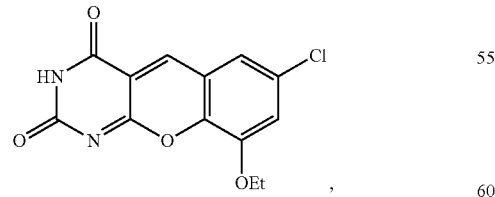

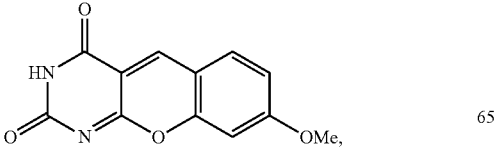

-continued

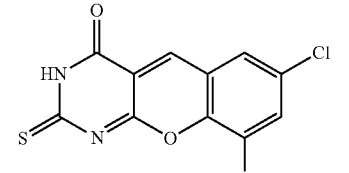

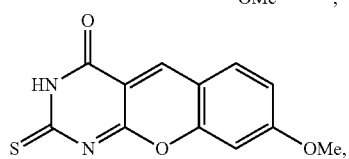

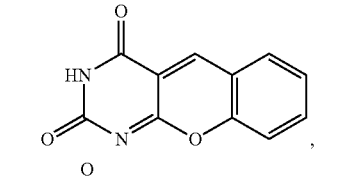

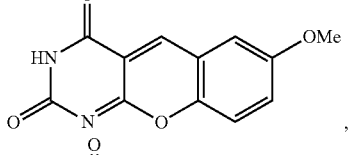

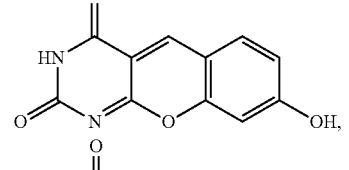

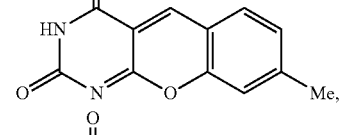

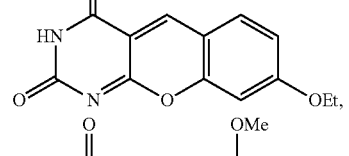

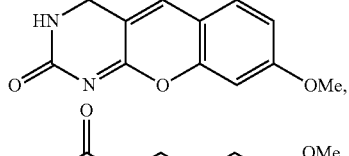

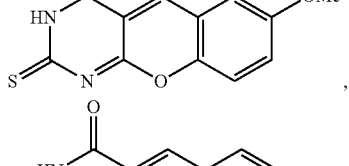

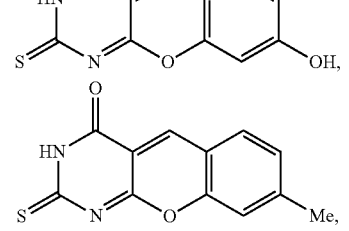

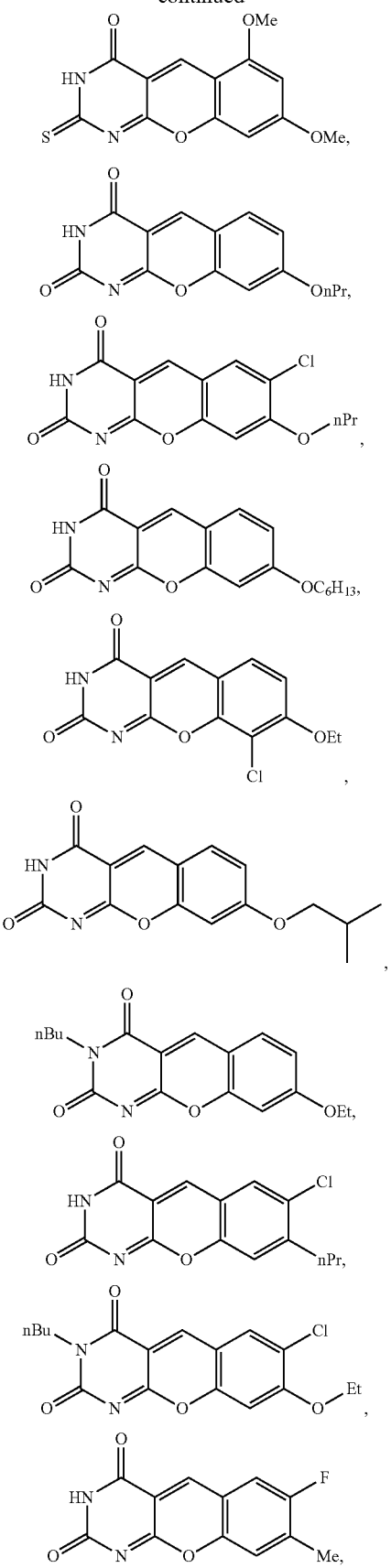
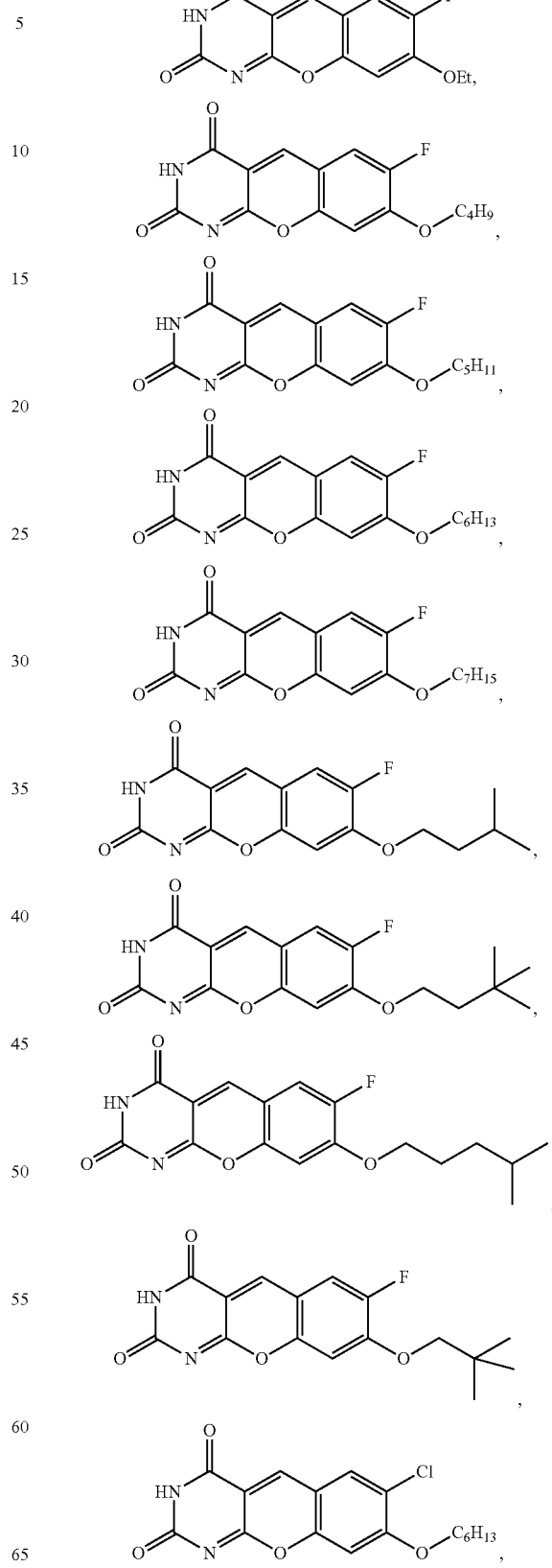

-continued
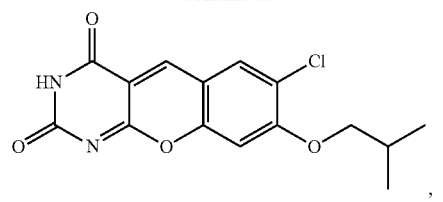
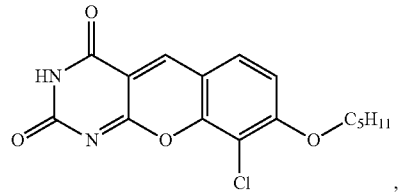
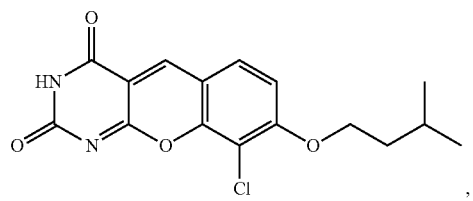
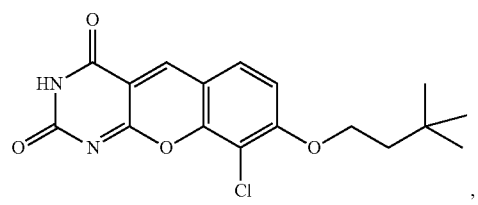
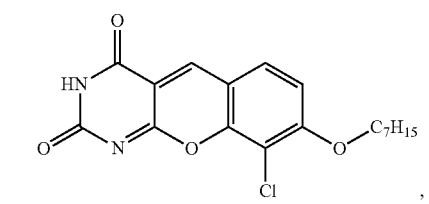
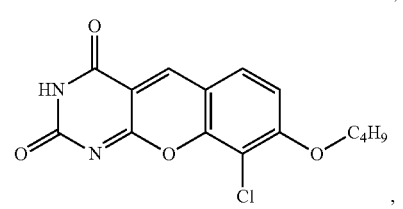
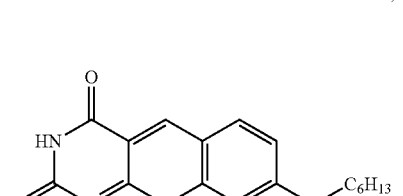
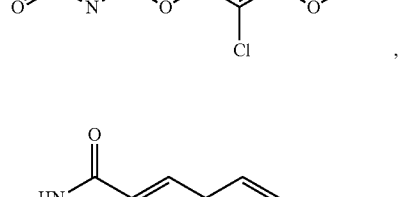
-continued
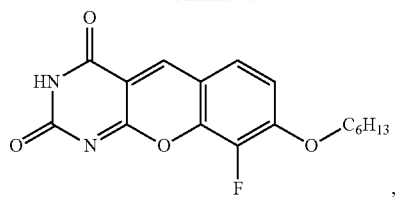
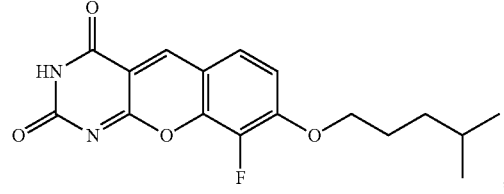
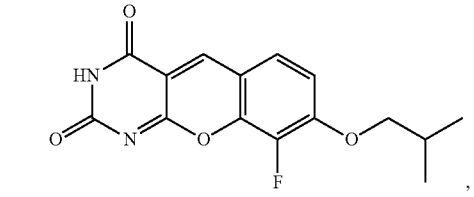
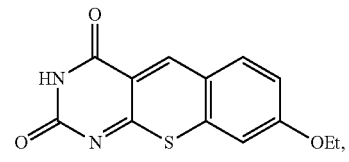
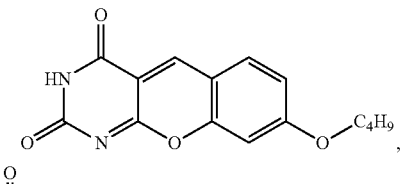
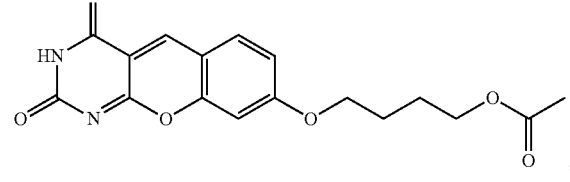
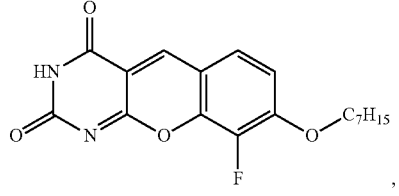
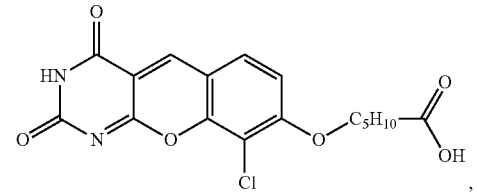
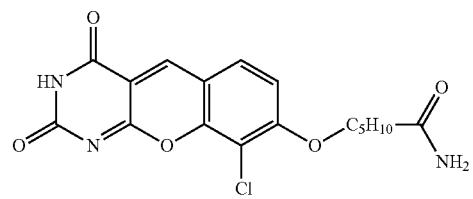

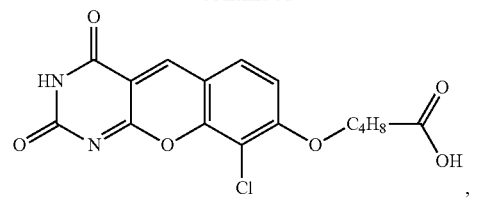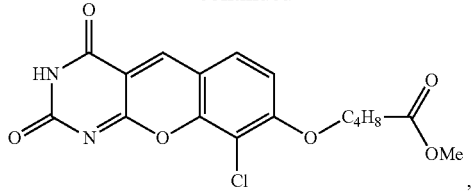

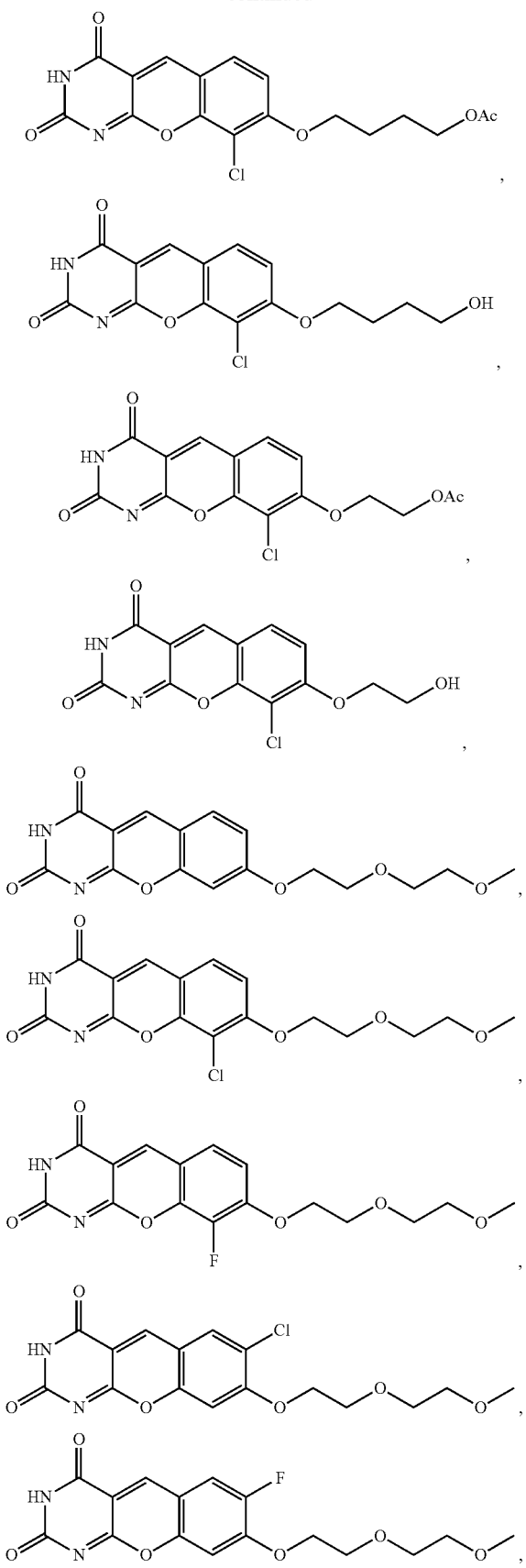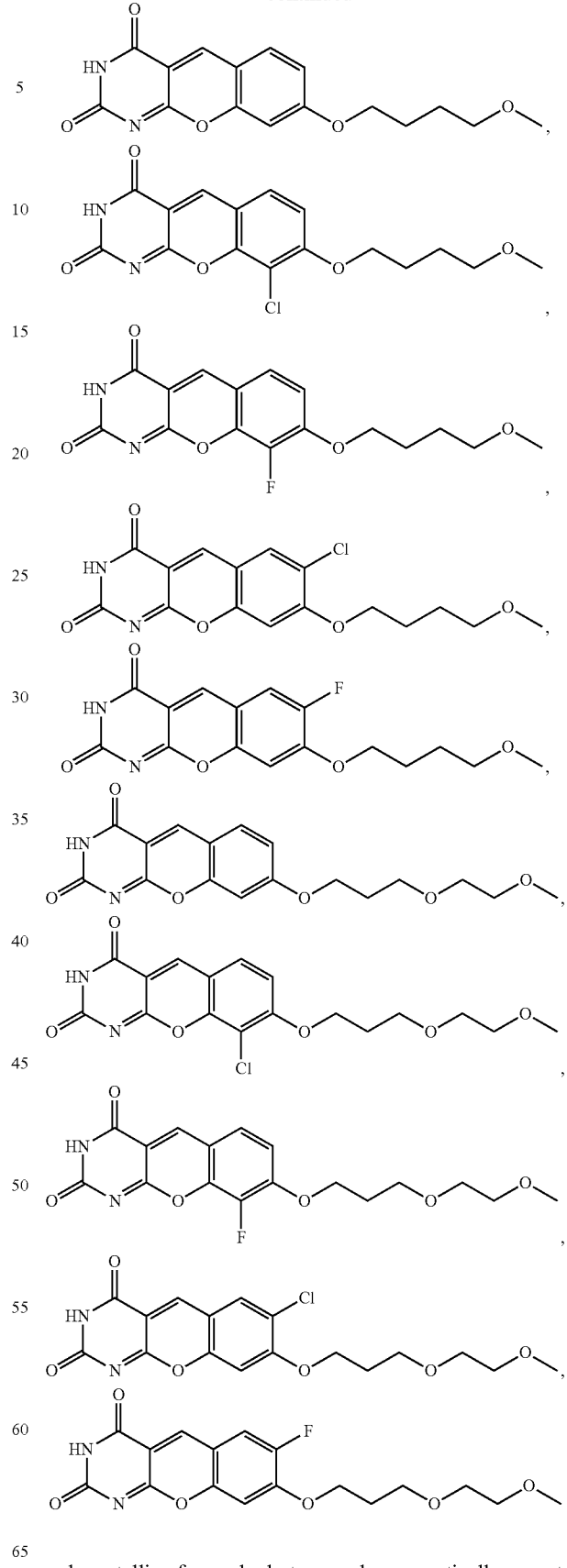
and crystalline forms, hydrates, or pharmaceutically acceptable salts thereof.

An additional embodiment of the present invention is a compound capable of inhibiting NF-κB. The compound is selected from the group consisting of:

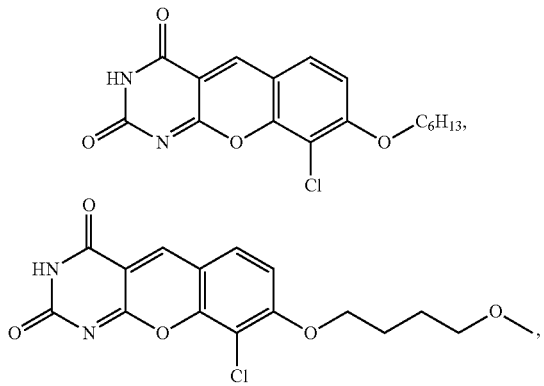

and crystalline forms, hydrates, or pharmaceutically acceptable salts thereof.

$R_1$ and $R_2$, $R_2$ and $R_3$, and $R_3$ and $R_4$, can be joined to form a ring, aromatic or not. The ring can be a hydrocarbon ring or a heterocyclic ring.

Another embodiment of the present invention is a pharmaceutical composition. The pharmaceutical composition comprises a pharmaceutically acceptable carrier and any of the compounds disclosed herein. The pharmaceutical composition may also include any number of other auxiliary agents used in the art, e.g., buffering agents, stabilizing agents, emulsifying agents, pH adjusting agents, surfactants, and flavorants.

A further embodiment of the present invention is a method of inhibiting NF-κB in a cell. The method comprises contacting the cell with any of the compounds disclosed herein.

As used herein, the term "contacting" means bringing a compound of the present invention into close proximity to the cells of the present invention. This may be accomplished using conventional techniques of drug delivery to mammals (e.g., tail vein injection, intravenous injection, peroral administration) or in the in vitro situation by, e.g., providing a compound of the present invention to a culture media to which the cells of the present invention are exposed.

Cells of the present invention include any cell type, cancerous or non-cancerous, in vitro or in vivo, that expresses NF-κB or any NF-κB family member. Cells of the present invention include, but are not limited to, human, monkey, ape, hamster, rat, or mouse cells. In some embodiments, cells of the present invention include, but are not limited to, CHO (e.g., CHO K1, DXB-11 CHO, Veggie-CHO), COS (e.g., COS-7), retinal cells, Vero, CV1, kidney (e.g., HEK293, 293 EBNA, MSR293, MDCK, HaK, BHK), HeLa, HepG2, WI38, MRC 5, Col0205, HB 8065, HL-60, (e.g., BHK21), Jurkat, Daudi, A431 (epidermal), CV-1, U937, 3T3, L cells, C127 cells, SP2/0, NS-0, MMT 060562, Sertoli cells, BRL 3A cells, HT1080 cells, myeloma cells, tumor cells, and any cell line derived from any of the aforementioned cells.

DEFINITIONS

The term "aliphatic", as used herein, means a group composed of carbon and hydrogen atoms that does not contain aromatic rings. Accordingly, aliphatic groups include alkyl, alkenyl, alkynyl, and carbocyclyl groups.

The term "alkyl" means the radical of saturated aliphatic groups that does not have a ring structure, including straight chain alkyl groups, and branched chain alkyl groups. Alkyl groups of the present invention have at least one and up to twenty carbon atoms and can be optionally substituted with one or more heteroatoms selected from halogen, nitrogen, oxygen, and sulfur.

The term "alkyl" also refers to cyclic hydrocarbon rings having at least three, and up to twenty, carbon atoms, optionally substituted with one or more heteroatoms selected from halogen, nitrogen, oxygen, and sulfur. The cyclic hydrocarbon ring can be monocyclic, bicyclic, polycyclic or bridge cyclic. Examples of alkyl groups include, but are not limited to, methyl, ethyl, propyl, isopropyl, butyl, isobutyl, pentyl, neopentyl, cyclopropyl, cyclobutyl, 2-chlorobutyl, 3-fluoropentyl, 4-hydroxybutyl, 3-methoxypropyl, 2-methoxypropyl, 2-methylbutyl, 3-methylbutyl (isopentyl), 2-chloro-4-hydroxybutyl, 5-aminohexyl, 2,2-difluorocyclobutyl, 1,3-difluorocyclohexyl, 3-thiolhexyl, and the like.

The term "alkenyl" refers to a straight or branched hydrocarbon chain having at least three, and up to twenty, carbon atoms with at least one double bond (—C=C—), optionally substituted with one or more heteroatoms selected from halogen, nitrogen, oxygen, and sulfur.

The term "alkenyl" also refers to cyclic hydrocarbon rings having at least three, and up to twenty, carbon atoms with at least one double bond (—C=C—), optionally substituted with one or more heteroatoms selected from halogen, nitrogen, oxygen, and sulfur. Examples of alkenyl groups include, but are not limited to, ethenyl, chlorovinyl, propenyl, propenylene, allyl, 1,4-butandienyl, 1,2-cyclobutenyl, and the like.

The term "alkynyl" refers to a straight or branched hydrocarbon chain having at least three, and up to twenty, carbon atoms with at least one triple bond, with or without one or more double bond, and optionally substituted with one or more heteroatoms selected from halogen, nitrogen, oxygen, and sulfur. The term "alkenyl" also refers to cyclic hydrocarbon rings with at least one triple bond with or without one or more double bond (—C=C—) and optionally substituted with one or more heteroatoms selected from halogen, nitrogen, oxygen, and sulfur. Examples of alkynyl groups include, but are not limited to, ethynyl, propynyl, butynyl, 3-methylbutynyl, and the like.

The term "aryl" refers to monocyclic, bicyclic or polycyclic aromatic hydrocarbon ring structures optionally substituted with one or more heteroatoms selected from halogen, nitrogen, oxygen, and sulfur, and/or optionally substituted with one or more alkyl, alkenyl or alkynyl groups. Examples of aryl groups include, but are not limited to, phenyl, naphthyl, hydroxyl phenyl, chlorophenyl, 2-chloro-4-fluorophenyl, methylphenyl, cyanonaphthyl, and the like.

The term "heterocyclic" refers to saturated or unsaturated mono- or poly-carbocyclic structures in which at least one carbon atom of at least one of the rings is replaced by nitrogen, sulfur, phosphorus, or oxygen. The term "heterocyclic" is intended to encompass fully saturated and unsaturated ring systems as well as partially unsaturated ring systems, including all possible isomeric forms of the heterocycle (for example, pyrrolyl comprises 1H-pyrrolyl and 2H-pyrrolyl).

Examples of a monocyclic heterocycle (e.g., a 4-, 5-, or 6-membered ring) or a bicyclic (e.g., a 5/6, 5/5, 6/6 system) saturated heterocycle include, but are not limited to, tetrahydrofuranyl, pyrrolidinyl, tetrahydrothienyl, dihydrooxazolyl, piperidinyl, hexahydropyrimidinyl, dioxanyl, morpholinyl, dithianyl, thiomorpholinyl, piperazinyl and the like.

Examples of a partially saturated monocyclic, bicyclic or tricyclic heterocycle include, but are not limited to, pyrrolinyl, imidazolinyl, pyrazolinyl, 2,3-dihydrobenzofuranyl, 1,3-benzodioxolanyl, 2,3dihydro-1,4-benzodioxinyl, indolinyl and the like.

Examples of an aromatic monocyclic, bicyclic or tricyclic heterocycle include, but are not limited to, pyrrolyl, furanyl, thienyl, imidazolyl, oxazolyl, isoxazolyl, thiazolyl, isothiazolyl, pyrazolyl, 1,2,3-triazolyl, 1,2,5-thiadiazolyl, 1,2,3-thiadiazolyl, 1,2,3-oxadiazolyl, 1,2,5-oxadiazolyl, pyridinyl, pyrimidinyl, pyrazinyl, pyridazinyl, triazinyl, benzofuranyl, isobenzofuranyl, benzothienyl, isobenzothienyl, indolizinyl, indolyl, isoindoly, benzoxazolyl, benzimidazolyl, indazolyl, benzisoxazolyl, benzisothiazolyl, benzopyrazolyl, benzoxadiazolyl, benzothiadiazolyl, benzotriazolyl, quinolinyl, isoquinolinyl, cinnolinyl, quinolizinyl, phthalazinyl, quinoxalinyl, quinazolinyl, naphthyridinyl, pteridinyl, pyrrolopyridinyl, thienopyridinyl, furanopyridinyl, isothiazolopyridinyl, thiazolopyridinyl, isoxazolopyridinyl, oxazolopyridinyl, pyrazolopyridinyl, imidazopyridinyl, pyrrolopyrazinyl, thienopyrazinyl, furanopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furanopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furanopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridinyl, thiadiazolopyridinyl, triazolopyridinyl, oxadiazolopyrazinyl, thiadiazolopyrazinyl, triazolopyrazinyl, oxadiazolopyrimidinyl, thiadiazolopyrim idinyl, triazolopyrimidinyl, oxadiazolopyridazinyl, thiadiazolopyridazinyl, triazolopyridazinyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl and the like.

The term "carbonyl" includes, but is not limited to, CHO (aldehyde group), COOH (carboxylic acid), COR$^a$ (ketone), COOR$^a$ (carboxylic ester), CONR$^a$R$^b$ (amide), CONHCONR$^a$R$^b$ (imide), R$^a$COX (acyl halide), and R$^a$COOCOR$^b$ (acid anhydride).

The term "halogen" includes, but is not limited to, fluorine, chlorine, bromine, iodine, and astatine.

In the present invention, the term "crystalline form" means the crystal structure of a compound. A compound may exist in one or more crystalline forms, which may have different structural, physical, pharmacological, or chemical characteristics. Different crystalline forms may be obtained using variations in nucleation, growth kinetics, agglomeration, and breakage.

Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

The term "hydrate", as used herein, means a solid or a semi-solid form of a chemical compound containing water in a molecular complex. The water is generally in a stoichiometric amount with respect to the chemical compound.

As used herein, "pharmaceutically acceptable salts" refer to derivatives of the compounds disclosed herein wherein the compounds are modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxy-ethyl)-pyrrolidine, sodium hydroxide, triethanolamine (2,2',2"-nitrilotris(ethanol)), trometh-amine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycero-phosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminum, calcium, lithium, magnesium, potassium, sodium, zinc and the like. (Pharmaceutical salts, Berge, S. M. et al., J. Pharm. Sci., (1977), 66, 1-19).

The pharmaceutically acceptable salts of the present invention can be synthesized from a compound disclosed herein which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

The compositions of the invention comprise one or more active ingredients in admixture with one or more pharmaceutically acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21 st Edition, Lippincott Williams and Wilkins, Philadelphia, Pa.).

Pharmaceutically acceptable diluents or carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

Any formulation of the invention may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The following examples are provided to further illustrate the methods of the present invention. These examples are illustrative only and are not intended to limit the scope of the invention in any way.

EXAMPLES

Example 1

General Synthesis Scheme

The NF-κB inhibitors of the present invention can be synthesized by any of the suitable methods known in the art, or as further described below.

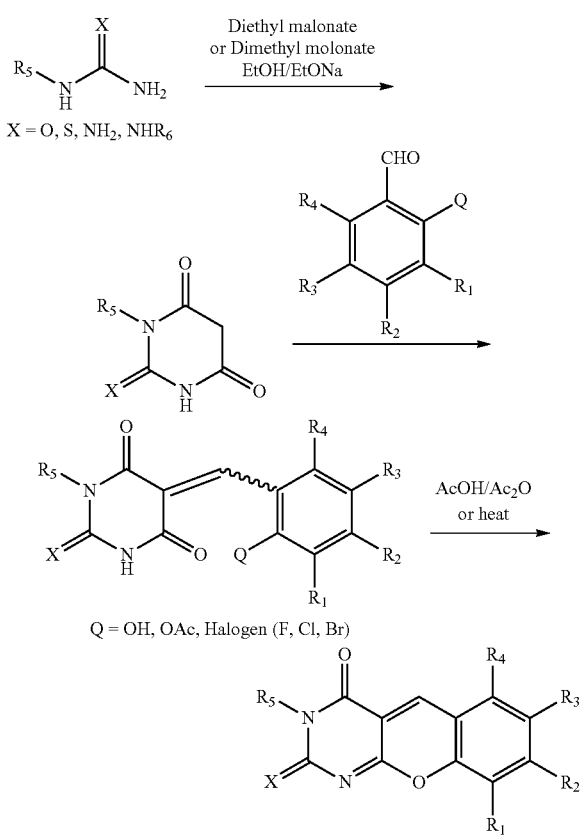

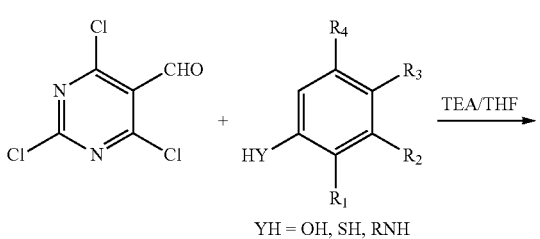

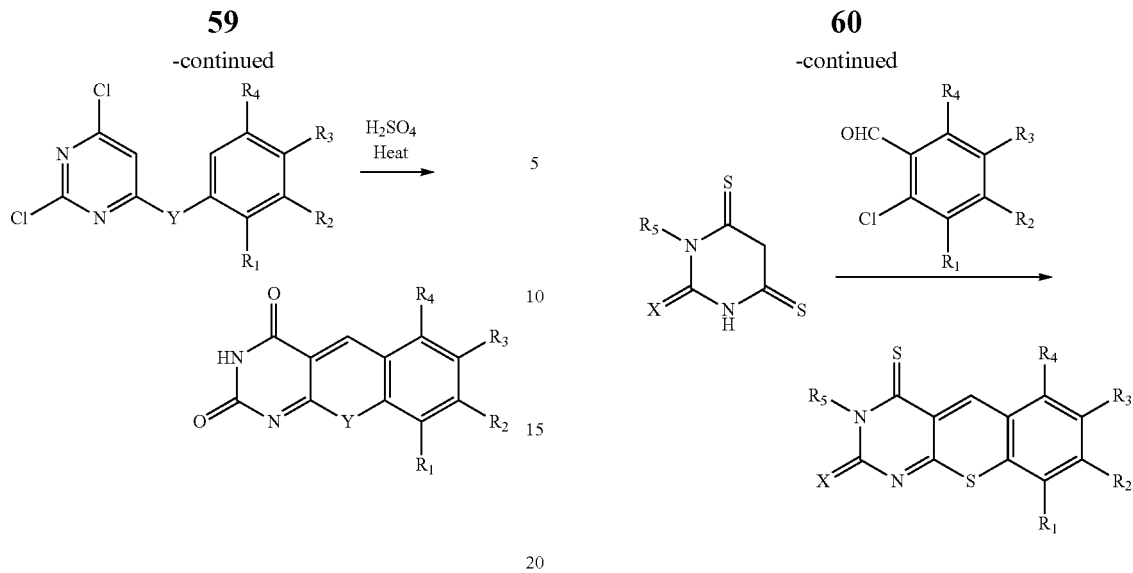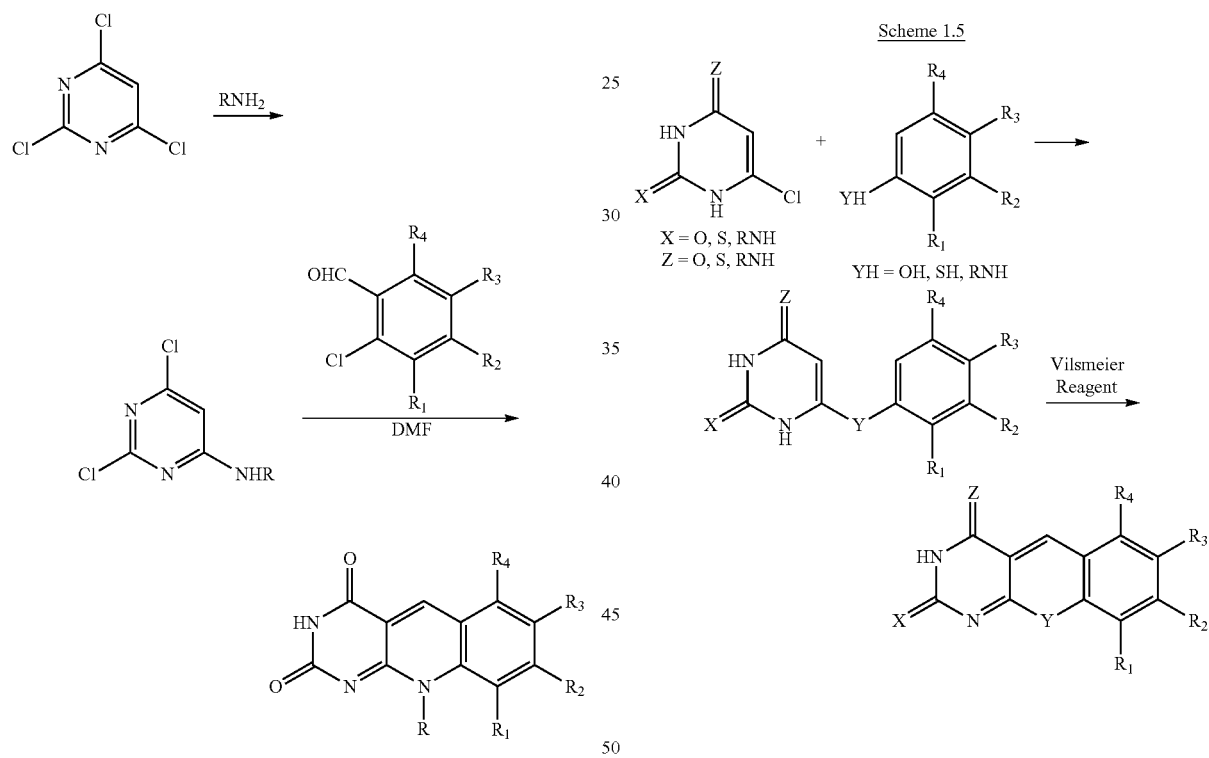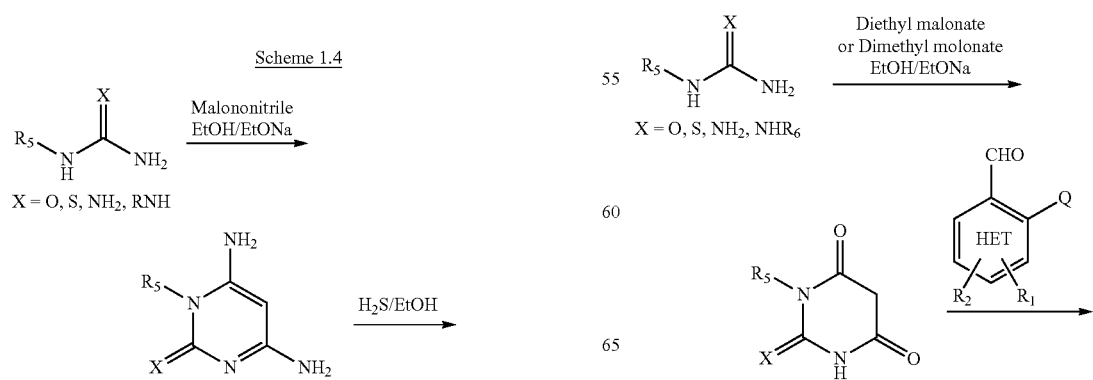

-continued

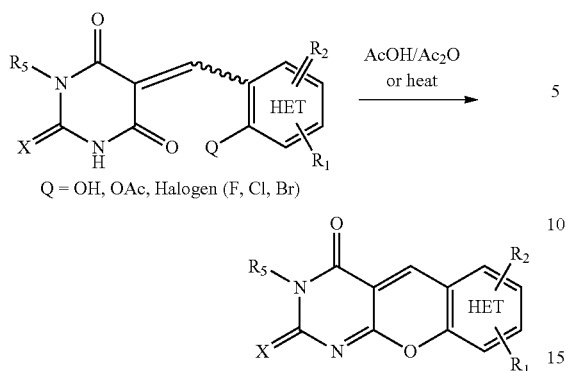

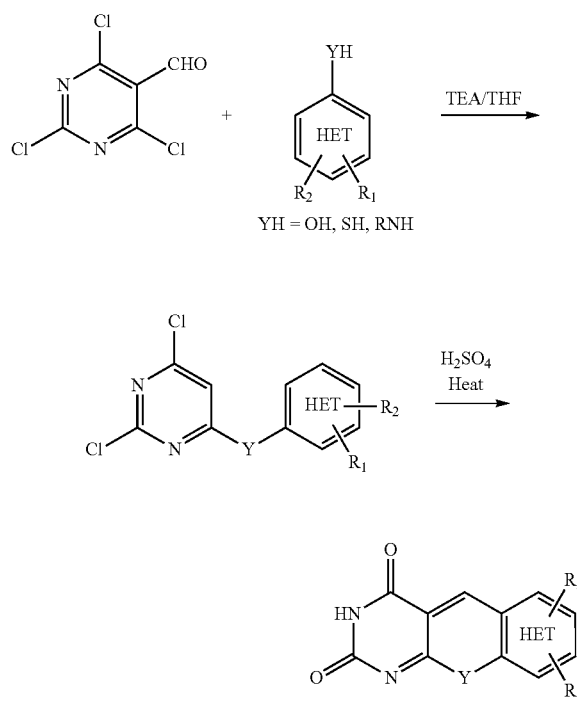

Scheme 2.2

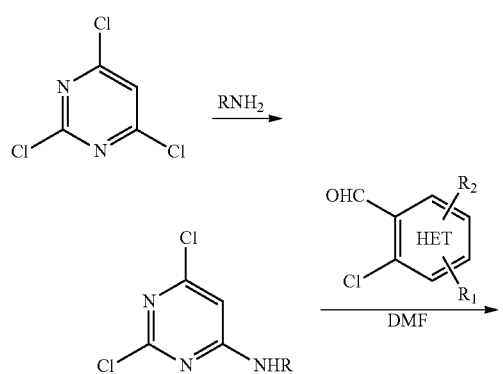

Scheme 2.3

-continued

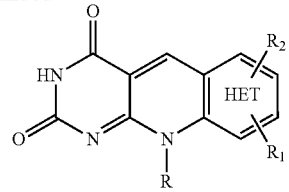

Example 2

Compound-Specific Synthesis Protocols

Preparation of 9-methoxy-2H-chromeno[2,3-d]pyrimidine-2,4(3H)-dione

Step 1: Preparation of compound 1a, 5-(2-hydroxy-3-methoxybenzylidene)pyrimidine-2,4,6(1H,3H,5H)-trione, 1a In a round bottom flask, a mixture of O-vanillin (1.52 g, 10.0 mmol) and barbituric acid (1.28 g, 10.0 mmol) in ethanol (20 ml) was stirred and heated to 30° C. overnight. The reaction mixture was cooled to room temperature. Subsequently, the reaction mixture was filtered. Solid yellow cake was collected and vacuum dried at 40° C. to 50° C. to yield desired product 1a, (2.20 g, 8.4 mmol, 84%).

Step 2: Preparation of 9-methoxy-2H-chromeno[2,3-d]pyrimidine-2,4(3H)-dione

In a scintillation vial, a suspension of compound 1a, (500 mg, 1.9 mmol) in a mixture of acetic acid (15 ml) and acetic anhydride (2 ml) was stirred and heated to 80° C. After 10 minutes at 80° C., the mixture turned homogeneous. The mixture was stirred at 80° C. for 3 hours. The mixture was cooled to room temperature and stirred overnight. Precipitation occurred during overnight stirring. Yellow solid was filtered, washed with water and vacuum dried at 40° C. to 50° C. to yield compound 1 (355 mg, 1.45 mmol, 77%).

Preparation of 9-ethoxy-2H-chromeno[2,3-d]pyrimidine-2,4(3H)-dione

Step 1: Preparation of compound 2a, 5-(3-ethoxy-2-hydroxybenzylidene)pyrimidine-2,4,6(1H,3H,5H)-trione, 2a In a scintillation vial, a mixture of 3-ethoxysalicyladehide (0.332 g, 2.0 mmol) and barbituric acid (0.256 g, 2.0 mmol) in ethanol (10 ml) was stirred and heated to 40° C. overnight. The reaction mixture was cooled to room temperature. Subsequently, the reaction mixture was filtered. Solid yellow cake was collected and vacuum dried at 40° C. to 50° C. to yield desired product 2a, (0.37 g, 1.3 mmol, 67%).

Step 2: Preparation of 9-ethoxy-2H-chromeno[2,3-d]pyrimidine-2,4(3H)-dione

In a scintillation vial, a suspension of compound 2a, (138 mg, 0.5 mmol) in a mixture of acetic acid (4.5 ml) and acetic anhydride (0.5 ml) was stirred and heated to 80° C. After 10 minutes at 80° C., the mixture turned homogeneous and remained homogeneous during the heating. The mixture was stirred at 80° C. for 1 hour. The mixture was cooled to room temperature. Acetic acid and acetic anhydride were removed from the reaction mixture by $N_2$ stream blowing to cause precipitation. Yellow solid was filtered, washed with water and vacuum dried at 40° C. to 50° C. to yield compound 2 (62 mg, 0.24 mmol, 48%).

Preparation of 7-chloro-9-methoxy-2H-chromeno[2, 3-d]pyrimidine-2,4(3H)-dione

Step 1: Preparation of 5-(5-chloro-2-hydroxy-3-methoxybenzylidene)pyrimidine-2,4,6(1H,3H,5H)-trione, 3a In a scintillation vial, a mixture of 5-chloro-2-hydroxy-3-methoxybenzaldehyde (0.374 g, 2.0 mmol) and barbituric acid (0.256 g, 2.0 mmol) in a mixture of ethanol (10 ml) and water (5 ml) was stirred and heated to 25° C. for 2 hours. The reaction mixture was cooled to room temperature. Subsequently, the reaction mixture was filtered. Solid yellow cake was collected and vacuum dried at 40° C. to 50° C. to yield desired product 3a, (0.51 g, 1.7 mmol, 86%).

Step 2: Preparation of 7-chloro-9-methoxy-2H-chromeno[2,3-d]pyrimidine-2,4(3H)-dione In a scintillation vial, a suspension of compound 3a, (148 mg, 0.5 mmol) in a mixture of acetic acid (4.5 ml) and acetic anhydride (0.5 ml) was stirred and heated to 80° C. for 1.5 hour. The mixture was cooled to room temperature. Acetic acid and acetic anhydride were removed from the reaction mixture by $N_2$ stream blowing to cause precipitation. Yellow solid was filtered, washed with water and vacuum dried at 40° C. to 50° C. to yield compound 3 (98 mg, 0.35 mmol, 70%).

Preparation of 7-bromo-9-methoxy-2H-chromeno[2, 3-d]pyrimidine-2,4(3H)-dione

Step 1: Preparation of 5-(5-bromo-2-hydroxy-3-methoxybenzylidene)pyrimidine-2,4,6(1H,3H,5H)-trione, 4a A solution of 5-bromo-2-hydroxy-3-methoxybenzaldehyde (0.462 g, 2.0 mmol) in ethanol (40 ml) was added to a solution of barbituric acid (0.256 g, 2.0 mmol) in water (40 ml). The mixture was stirred at room temperature for 2 days. Subsequently, the reaction mixture was filtered. Orange solid cake was collected and vacuum dried at 40° C. to 50° C. to yield desired product 4a, (0.46 g, 1.34 mmol, 67%).

Step 2: Preparation of 7-bromo-9-methoxy-2H-chromeno[2,3-d]pyrimidine-2,4(3H)-dione In a scintillation vial, a suspension of compound 4a, (170 mg, 0.5 mmol) in a mixture of acetic acid (4.5 ml) and acetic anhydride (0.5 ml) was stirred and heated to 80° C. for 30 hours. The mixture was cooled to room temperature. Acetic acid and acetic anhydride were removed from the reaction mixture by $N_2$ stream blowing to cause precipitation. Yellow solid was filtered, washed with water and vacuum dried at 40° C. to 50° C. to yield compound 4 (145 mg, 0.45 mmol, 90%).

Preparation of 7-chloro-9-methoxy-2H-chromeno[2, 3-d]pyrimidine-2,4(3H)-dione

Step 1: Preparation of 5-chloro-3-ethoxy-2-hydroxybenzaldehyde, 5a

In a round bottom flask, N-chlorosuccinimide (8.68 g, 65 mmol) was added to a solution of 3-ethoxysalicylaldehyde (8.30 g, 50 mmol) in THF (100 ml). The mixture was stirred at room temperature for 5 hours. The reaction was quenched with water (100 ml) and extracted with ethyl acetate (150 ml). The organic layer was washed successively with saturated $NaHCO_3$ aq, HCl aq. (0.5 M, 150 ml) and then with brine (150 ml). Organic layer was concentrated to dryness to yield compound 5a (9.60 g, 48 mmol, 96%) that can be used in the next step without further purification.

Step 2: Preparation of 5-(5-bromo-2-hydroxy-3-methoxybenzylidene)pyrimidine-2,4,6(1H,3H,5H)-trione, 5b In a scintillation vial, a mixture of 5a (0.40 g, 2.0 mmol), barbituric acid (0.256 g, 2.0 mmol), ethanol (7 ml) and water (10 ml) was stirred at room temperature for 2 hours. Subsequently, the reaction mixture was filtered. Solid yellow cake was collected and vacuum dried at 40° C. to 50° C. to yield desired product 5b, (0.558 g, 1.88 mmol, 94%).

Step 3: Preparation of 7-chloro-9-methoxy-2H-chromeno[2,3-d]pyrimidine-2,4(3H)-dione In a scintillation vial, a suspension of compound 5b, (100 mg, 0.5 mmol) in a mixture of acetic acid (4.5 ml) and acetic anhydride (0.5 ml) was stirred and heated to 80° C. for 0.5 hour. The mixture turned homogeneous after 10 minutes at 80° C. Precipitation reoccurred after 20 minutes at 80° C. The reaction was stopped after 30 minutes. The mixture was cooled to room temperature. Yellow solid was filtered, washed with water and vacuum dried at 40° C. to 50° C. to yield compound 5 (58 mg, 0.20 mmol, 40%).

Preparation of 8-methoxy-2H-chromeno[2,3-d]pyrimidine-2,4(3H)-dione

Step 1: Preparation of 5-(2-hydroxy-4-methoxybenzylidene)pyrimidine-2,4,6(1H,3H,5H)-trione, 6a In a scintillation vial, a mixture of 2-hydroxy-4-methoxybenzaldehyde (0.456 g, 3.0 mmol), barbituric acid (0.384 g, 3.0 mmol), ethanol (10 ml) and water (5 ml) was stirred at room temperature for 15 hours. Subsequently, the reaction mixture was filtered. Solid yellow cake was collected and vacuum dried at 40° C. to 50° C. to yield desired product 6a, (0.695 g, 2.65 mmol, 88%).

Step 2: Preparation of 8-methoxy-2H-chromeno[2, 3-d]pyrimidine-2,4(3H)-dione

In a scintillation vial, a suspension of compound 6a, (278 mg, 1.0 mmol) in a mixture of acetic acid (4.5 ml) and acetic anhydride (0.5 ml) was stirred and heated to 80° C. for 2 hours. The mixture turned homogeneous after 10 minutes at 80° C. The mixture was cooled to room temperature. Yellow solid was filtered, washed with ethanol and then with water and vacuum dried at 40° C. to 50° C. to yield compound 6 (148 mg, 0.60 mmol, 60%).

Preparation of 7-chloro-9-methoxy-2-thioxo-2H-chromeno[2,3-d]pyrimidin-4(3H)-one Step 1: Preparation of 5-(5-chloro-2-hydroxy-3-methoxybenzylidene)-2-thioxodihydropyrimidine-4, 6(1H,5H)-dione, 7a In a scintillation vial, a mixture of 5-chloro-2-hydroxy-3-methoxybenzaldehyde (0.374 g, 2.0 mmol), 2-thiobarbituric acid (0.288 g, 3.0 mmol), ethanol (15 ml) and water (5 ml) was stirred at room temperature for 15 hours. Subsequently, the reaction mixture was filtered. Solid orange cake was collected and vacuum dried at 40° C. to 50° C. to yield desired product 7a, (0.47 g, 1.5 mmol, 75%).

Step 2: Preparation of 7-chloro-9-methoxy-2-thioxo-2H-chromeno[2,3-d]pyrimidin-4(3H)-one In a scintillation vial, a suspension of compound 7a, (158 mg, 0.5 mmol) in a mixture of acetic acid (4.5 ml) and acetic anhydride (0.5 ml) was stirred and heated to 80° C. for 2 hours. The mixture was cooled to room temperature. Red solid was filtered, washed with ethanol and then with water and vacuum dried at 40° C. to 50° C. to yield compound 7 (62 mg, 0.21 mmol, 42%).

Preparation of 8-methoxy-2-thioxo-2H-chromeno[2,3-d]pyrimidin-4(3H)-one

Step 1: Preparation of 5-(2-hydroxy-4-methoxybenzylidene)-2-thioxodihydropyrimidine-4,6(1H,5H)-dione, 8a In a scintillation vial, a mixture of 2-hydroxy-4-methoxybenzaldehyde (0.456 g, 3.0 mmol), 2-thiobarbituric acid (0.288 g, 3.0 mmol), ethanol (10 ml) and water (5 ml) was stirred at room temperature for 2 hours. Subsequently, the reaction mixture was filtered. Solid yellow cake was collected and vacuum dried at 40° C. to 50° C. to yield desired product 8a, (0.761 g, 2.73 mmol, 91%).

Step 2: Preparation of 8-methoxy-2-thioxo-2H-chromeno[2,3-d]pyrimidin-4(3H)-one

In a scintillation vial, a suspension of compound 8a, (150 mg, 0.54 mmol) in a mixture of acetic acid (4.5 ml) and acetic anhydride (0.5 ml) was stirred and heated to 80° C. for 2 hours. The mixture was cooled to room temperature. Red solid was filtered, and re-suspended in saturated aqueous solution of NaHCO3 for 1 hour. Red solid was filtered again, washed with water and vacuum dried at 40° C. to 50° C. to yield compound 8 (84 mg, 0.32 mmol, 60%).

Preparation of 2H-chromeno[2,3-d]pyrimidine-2,4(3H)-dione

Step 1: Preparation of 5-(2-hydroxybenzylidene)pyrimidine-2,4,6(1H,3H,5H)-trione, 9a In a scintillation vial, a mixture of salicylaldehyde (0.122 g, 1.0 mmol), barbituric acid (0.128 g, 1.0 mmol) and water (10 ml) was stirred at room temperature for 1 hour. Subsequently, the reaction mixture was filtered. Solid yellow cake was collected and vacuum dried at 40° C. to 50° C. to yield desired product 9a, (0.761 g, 2.73 mmol, 91%).

Step 2: Preparation of 2H-chromeno[2,3-d]pyrimidine-2,4(3H)-dione

In a scintillation vial, a suspension of compound 9a, (116 mg, 0.5 mmol) in a mixture of acetic acid (4.5 ml) and acetic anhydride (0.5 ml) was stirred and heated to 80° C. for 2 hours. The mixture was cooled to room temperature. Yellow solid was filtered, washed with water and vacuum dried at 40° C. to 50° C. to yield compound 9 (43 mg, 0.20 mmol, 40%).

Preparation of 7-methoxy-2H-chromeno[2,3-d]pyrimidine-2,4(3H)-dione

Step 1: Preparation of 5-(2-hydroxy-5-methoxybenzylidene)pyrimidine-2,4,6(1H,3H,5H)-trione, 10a In a scintillation vial, a mixture of 2-hydroxy-5-methoxybenzaldehyde (0.304 g, 2.0 mmol), barbituric acid (0.256 g, 2.0 mmol) and water (10 ml) was stirred at room temperature for 3 hours. Subsequently, the reaction mixture was filtered. Solid red cake was collected and vacuum dried at 40° C. to 50° C. to yield desired product 10a, (0.42 g, 1.60 mmol, 80%).

Step 2: Preparation of 7-methoxy-2H-chromeno[2,3-d]pyrimidine-2,4(3H)-dione

In a scintillation vial, a suspension of compound 10a, (131 mg, 0.5 mmol) in a mixture of acetic acid (4.5 ml) and acetic anhydride (0.5 ml) was stirred and heated to 80° C. for 3 hours. The mixture was cooled to room temperature. Yellow solid was filtered, washed with water and vacuum dried at 40° C. to 50° C. to yield compound 10 (110 mg, 0.20 mmol, 90%).

Preparation of 8-hydroxy-2H-chromeno[2,3-d]pyrimidine-2,4(3H)-dione

Step 1: Preparation of 5-(2,4-dihydroxybenzylidene)pyrimidine-2,4,6(1H,3H,5H)-trione, 11a In a scintillation vial, a mixture of 2,4-dihydroxybenzaldehyde (0.276 g, 2.0 mmol), barbituric acid (0.256 g, 2.0 mmol) and ethanol (8 ml) was stirred at room temperature for 15 hours. Subsequently, the reaction mixture was filtered. Solid orange cake was collected and vacuum dried at 40° C. to 50° C. to yield desired product 11a, (0.447 g, 1.8 mmol, 90%).

Step 2: Preparation of 8-hydroxy-2H-chromeno[2,3-d]pyrimidine-2,4(3H)-dione

In a scintillation vial, a suspension of compound 11a, (124 mg, 0.5 mmol) in a mixture of acetic acid (3 ml) and acetic anhydride (1 ml) was stirred and heated to 80° C. for 18 hours. The mixture was cooled to room temperature and stirred overnight. Yellow solid was filtered, washed with water and vacuum dried at 40° C. to 50° C. to yield compound 11 (85 mg, 0.37 mmol, 74%).

Preparation of 8-methyl-2H-chromeno[2,3-d]pyrimidine-2,4(3H)-dione

Step 1: Preparation of 5-(2-hydroxy-4-methylbenzylidene)pyrimidine-2,4,6(1H,3H,5H)-trione, 12a In a scintillation vial, a mixture of 2-hydroxy-4-methylbenzaldehyde (0.272 g, 2.0 mmol), barbituric acid (0.256 g, 2.0 mmol) and water (10 ml) was stirred at room temperature for 3 hours. Subsequently, ethyl acetate (5 ml) was added to the reaction mixture to wash unreacted 2-hydroxy-4-methylbenzaldehyde. The reaction mixture was filtered. Solid yellow cake was collected and vacuum dried at 40° C. to 50° C. to yield desired product 12a, (0.461 g, 1.87 mmol, 94%).

Step 2: Preparation of 8-methyl-2H-chromeno[2,3-d]pyrimidine-2,4(3H)-dione

In a scintillation vial, a suspension of compound 12a, (123 mg, 0.5 mmol) in a mixture of acetic acid (2.5 ml) and acetic anhydride (0.25 ml) was stirred and heated to 80° C. for 5 hours. The mixture was cooled to room temperature and stirred overnight. Yellow solid was filtered, washed with water and vacuum dried at 40° C. to 50° C. to yield compound 12 (100 mg, 0.44 mmol, 88%).

Preparation of 8-ethoxy-2H-chromeno[2,3-d]pyrimidine-2,4(3H)-dione

Step 1: Preparation of 4-ethoxy-2-hydroxybenzaldehyde, 13a

A suspension of 2,4-dihydroxybenzaldehyde (3.04 g, 20 mmol), ethyl bromide (2.29 g, 21 mmol), potassium carbonate (2.90 g, 21 mmol), NaI (2.98 g, 20 mmol) and 18-crown-6 (0.528 g, 2 mmol) in acetone (15 ml) was stirred and heated to 70° C. for 15 hours. The mixture was cooled to room temperature and quenched with HCl, aq. 1M. The mixture was extracted with ethyl acetate (50 ml). Organic layer was washed with water (50 ml) twice and then with brine (50 ml). Organic layer was dried over MgSO4, concentrated and chromatographed to yield 4-ethoxy-2-hydroxybenzaldehyde (3.01 g, 18.1 mmol, 90%) and 2,4-diethoxybenzaldehyde (0.134 g, 0.7 mmol, 3.4%).

Step 2: Preparation of 5-(4-ethoxy-2-hydroxybenzylidene)pyrimidine-2,4,6(1H,3H,5H)-trione, 13b In a scintillation vial, a mixture of 2-hydroxy-4-ethoxybenzaldehyde (0.498 g, 3.0 mmol), barbituric acid (0.384 g, 3.0 mmol) and water (10 ml) was stirred at room temperature for 2 hours. The reaction mixture was filtered. Solid yellow cake was collected and vacuum dried at 40° C. to 50° C. to yield desired product 13b, (0.68 g, 2.46 mmol, 82%).

Step 3: Preparation of 8-ethoxy-2H-chromeno[2,3-d]pyrimidine-2,4(3H)-dione

In a scintillation vial, a suspension of compound 13b, (276 mg, 1.0 mmol) in a mixture of acetic acid (5.0 g) and acetic anhydride (0.612 g, 6 mmol) was stirred and heated to 80° C. for 3 hours. Yellow solid was filtered, washed with water and vacuum dried at 40° C. to 50° C. to yield compound 13 (177 mg, 0.68 mmol, 68%).

Preparation of 6,8-dimethoxy-2H-chromeno[2,3-d]pyrimidine-2,4(3H)-dione

Step 1: Preparation of 2,4,6-trimethoxybenzaldehyde, 14a

In a round bottom flask, POCl3 (7.3 ml, 80 mmol) was added to a mixture of 1,3,5-trimethoxybenzene (8.41 g, 50 mmol) in DMF (15 ml). The temperature of reaction mixture was kept below 30° C. by slowly adding POCl3. After addition of POCl3, the mixture was still stirred at room temperature for an addition 1 hour. The reaction mixture was added into a cold saturated NaHCO3 solution. The pH of the solution was adjusted to remain above 7. Precipitation of desired product occurred. The off-white product was filtered and rinsed with NaHCO3 aq., then with HCl aq. 0.5M and then with water. Off-white solid was collected and vacuum dried at room temperature to yield 14a (9.60 g, 48 mmol, 98%).

Step 2: 2-hydroxy-4,6-dimethoxybenzaldehyde, 14b

A solution of 14a (5.88 g, 30 mmol) in dichloromethane (40 ml) in a round bottom flask was cooled to 0° C. (ice+brine bath). To the solution was added BCl3 (45 ml of 1M solution in hexane, 45 mmol). The reaction mixture was allowed to slowly warm to room temperature over 1 hour. After 1.5 hour of reaction, TLC analysis indicated that trace amount of starting material remained. An additional BCl3 (10 ml of 1M solution in hexane, 10 mmol) was added into the mixture. The mixture was stirred at room temperature for an additional 1 hour. Subsequently, the reaction mixture was quenched with HCl aq. 1M (100 ml). The mixture was extracted with ethyl acetate. The organic layer was successively washed with HCl aq. 1M and brine, and then dried over Mg2SO4. The organic layer was concentrated and chromatographed to yield 14b (5.44 g, 29.8 mmol, 99%).

Step 3: Preparation of 5-(2-hydroxy-4,6-dimethoxybenzylidene)pyrimidine-2,4,6(1H,3H,5H)-trione, 14c In a scintillation vial, a mixture of 4,6-dimethoxysalicylaldehyde (0.364 g, 2.0 mmol), barbituric acid (0.256 g, 2.0 mmol) and water (10 ml) was stirred at room temperature for 4.5 hours. The reaction mixture was filtered. Solid orange cake was collected and vacuum dried at 40° C. to 50° C. to yield a mixture containing 4,6-dimethoxysalicylaldehyde, 5-(2-hydroxy-4,6-dimethoxybenzylidene)pyrimidine-2,4,6 (1H,3H,5H)-trione and 5-(6,8-dimethoxy-2,4-dioxo-2,3,4,5-tetrahydro-1H-chromeno[2,3-d]pyrimidin-5-yl)pyrimidine-2,4,6(1H,3H,5H)-trione. The mixture was purified by (1) washed with hot ethyl acetate to remove 4,6-dimethoxysalicylaldehyde; (2) re suspended solid obtained after ethyl acetate wash in NaHCO3 aq. The suspension was filtered to obtain a yellow cake. The yellow cake was vacuum dried at 40° C. to 50° C. to yield desired product 14c, (56 mg, 0.19 mmol, 9.6%).

Step 4: Preparation of 6,8-dimethoxy-2H-chromeno[2,3-d]pyrimidine-2,4(3H)-dione In a scintillation vial, a suspension of compound 14c, (56 mg, 0.19 mmol) in a mixture of acetic acid (2 ml) and acetic anhydride (0.2 ml) was stirred and heated to 80° C. for 5 hours. Yellow solid was filtered, washed with water and vacuum dried at 40° C. to 50° C. to yield compound 14 (35 mg, 0.13 mmol, 67%).

Preparation of 7-methoxy-2-thioxo-2H-chromeno[2,3-d]pyrimidin-4(3H)-one

Step 1: Preparation of 5-(2-hydroxy-5-methoxybenzylidene)-2-thioxodihydropyrimidine-4,6(1H,5H)-dione, 15a In a scintillation vial, a mixture of 2-hydroxy-5-methoxybenzaldehyde (0.456 g, 3.0 mmol), 2-thiobarbituric acid (0.432 g, 2.0 mmol), ethanol (10 ml) and water (5 ml) was stirred at room temperature for 15 hours. Subsequently, the reaction mixture was filtered. Solid red cake was collected and vacuum dried at 40° C. to 50° C. to yield desired product 15a, (0.716 g, 2.57 mmol, 86%).

Step 2: Preparation of 7-methoxy-2-thioxo-2H-chromeno[2,3-d]pyrimidin-4(3H)-one In a scintillation vial, a suspension of compound 15a, (139 mg, 0.5 mmol) in a mixture of acetic acid (4.5 ml) and acetic anhydride (0.5 ml) was stirred and heated to 80° C. for 4 hours. The mixture was cooled to room temperature. Bordeaux red solid was filtered, washed with water and vacuum dried at 40° C. to 50° C. to yield compound 15 (85 mg, 0.33 mmol, 65%).

Preparation of 8-hydroxy-2-thioxo-2H-chromeno[2,3-d]pyrimidin-4(3H)-one

Step 1: Preparation of 5-(2,4-dihydroxybenzylidene)-2-thioxodihydropyrimidine-4,6(1H,5H)-dione, 16a In a scintillation vial, a mixture of 2,4-dihydroxybenzaldehyde (0.414 g, 3.0 mmol), 2-thiobarbituric acid (0.432 g, 2.0 mmol), ethanol (10 ml) and water (5 ml) was stirred at room temperature for 5 hours. Subsequently, the reaction mixture was filtered. Solid red cake was collected and vacuum dried at 40° C. to 50° C. to yield desired product 16a, (0.697 g, 2.60 mmol, 88%).

Step 2: Preparation of 8-hydroxy-2-thioxo-2H-chromeno[2,3-d]pyrimidin-4(3H)-one In a scintillation vial, a suspension of compound 16a, (132 mg, 0.5 mmol) in a mixture of acetic acid (4.5 ml) and acetic anhydride (0.5 ml) was stirred and heated to 80° C. for 4 hours. The mixture was cooled to room temperature. Orange solid was filtered, washed with water and vacuum dried at 40° C. to 50° C. to yield compound 16 (115 mg, 0.47 mmol, 93%).

Preparation of 8-methyl-2-thioxo-2H-chromeno[2,3-d]pyrimidin-4(3H)-one

Step 1: Preparation of 5-(2-hydroxy-4-methylbenzylidene)-2-thioxodihydropyrimidine-4,6(1H,5H)-dione, 17a In a scintillation vial, a mixture of 2-hydroxy-4-methoxybenzaldehyde (0.272 g, 3.0 mmol), 2-thiobarbituric acid (0.288 g, 2.0 mmol), and water (10 ml) was stirred at room temperature for 13 hours. Ethyl acetate (5 ml) was added to the reaction mixture to wash unreacted 2-hydroxy-4-methoxybenzaldehyde. Subsequently, the reaction mixture was filtered. Solid yellow cake was collected and vacuum dried at 40° C. to 50° C. to yield desired product 17a, (0.437 g, 1.67 mmol, 83%).

Step 2: Preparation of 8-methyl-2-thioxo-2H-chromeno[2,3-d]pyrimidin-4(3H)-one In a scintillation vial, a suspension of compound 17a, (131 mg, 0.5 mmol) in a mixture of acetic acid (2.5 ml) and acetic anhydride (0.25 ml) was stirred and heated to 80° C. for 7 hours. The mixture was cooled to room temperature. Yellow solid was filtered, washed with NaHCO3 aq., then with water and vacuum dried at 40° C. to 50° C. to yield compound 17 (33 mg, 0.13 mmol, 27%).

Preparation of 6,8-dimethoxy-2-thioxo-2H-chromeno[2,3-d]pyrimidin-4(3H)-one

Step 1, Preparation of 5-(2-hydroxy-4,6-dimethoxybenzylidene)-2-thioxodihydropyrimidine-4,6(1H, 5H)-dione, 18a In a scintillation vial, a mixture of 4,6-dimethoxysalicylaldehyde (0.364 g, 2.0 mmol), 2-thiobarbituric acid (0.288 g, 2.0 mmol) and water (15 ml) was stirred and warmed to 50° C. for 30 minutes. The mixture was cooled to room temperature for 15 hours. The reaction mixture was filtered. Solid orange cake was collected and re-suspended in ethyl acetate (20 ml). The suspension was filtered to remove ethyl acetate and unreacted 4,6-dimethoxysalicylaldehyde. The solid orange from ethyl acetate was again re-suspended in saturated NaHCO3 aq. The suspension was filtered and washed with water. The solid orange from saturated NaHCO3 aq. suspension was vacuum dried at 40° C. to 50° C. to yield compound 18a, (0.202 g, 0.65 mmol, 33%).

Step 2: Preparation of 6,8-dimethoxy-2-thioxo-2H-chromeno[2,3-d]pyrimidin-4(3H)-one In a scintillation vial, a suspension of compound 18a, (154 mg, 0.5 mmol) in a mixture of acetic acid (2.7 ml) and acetic anhydride (0.3 ml) was stirred and heated to 80° C. for 4 hours. The mixture was cooled to room temperature. Red solid was filtered, washed with water and vacuum dried at 40° C. to 50° C. to yield compound 18 (85 mg, 0.29 mmol, 58%).

Preparation of 8-propoxy-2H-chromeno[2,3-d]pyrimidine-2,4(3H)-dione

Step 1: Preparation of 4-n-Propoxy-2-hydroxybenzaldehyde, 19a

A suspension of 2,4-dihydroxybenzaldehyde (0.76 g, 5.5 mmol), 1-iodopropane (1.02 g, 6 mmol), potassium carbonate (7.60 g, 5.5 mmol), and 18-crown-6 (0.132 g, 0.5 mmol) in acetone (12 ml) was stirred and heated to 65° C. for 15 hours. The mixture was cooled to room temperature and quenched with HCl, aq. 1M. The mixture was extracted with ethyl acetate (50 ml). Organic layer was washed with water (50 ml) twice and then with brine (50 ml). Organic layer was dried over MgSO4, concentrated and chromatographed to yield 4-n-Propoxy-2-hydroxybenzaldehyde, 19a (0.747 g, 3.85 mmol, 77%).

Step 2: Preparation of 5-(2-hydroxy-4-propoxybenzylidene)pyrimidine-2,4,6(1H,3H,5H)-trione, 19b In a round bottom flask, a mixture of 19a (0.66 g, 4.0 mmol), barbituric acid (0.512 g, 4.0 mmol), ethanol (15 ml) and water (20 ml) was stirred at room temperature for 15 hours. The reaction mixture was concentrated to reduce volume by 30% by evaporation. After ethanol evaporation, water (30 ml) was added to the reaction mixture. The reaction was stirred at room temperature for 30 minutes and then filtered. Solid yellow cake was collected and vacuum dried at 40° C. to 50° C. to yield compound 19b, (0.777 g, 2.68 mmol, 67%).

Step 3: Preparation of 8-propoxy-2H-chromeno[2,3-d]pyrimidine-2,4(3H)-dione

In a scintillation vial, a suspension of compound 19b, (145 mg, 0.5 mmol) in a mixture of acetic acid (2.5 g) and acetic anhydride (0.31 g, 3 mmol) was stirred and heated to 80° C. for 15 hours. The mixture was cooled to room temperature. Yellow solid was filtered, washed with water and vacuum dried at 40° C. to 50° C. to yield compound 19 (42 mg, 0.15 mmol, 30%).

Preparation of 7-chloro-8-propoxy-2H-chromeno[2,3-d]pyrimidine-2,4(3H)-dione

Step 1: Preparation of 5-chloro-2,4-dihydroxybenzaldehyde

In a scintillation vial, 2,4-dihydroxybenzaldehyde (1.38 g, 10 mmol) was dissolved in ethyl ether (18 ml). The mixture was placed under N2 atmosphere and cooled to 0° C. To the mixture was added sulfuryl chloride (0.91 ml, 11 mmol). The mixture was kept under N2 atmosphere at 0° C. for 30 minutes. The reaction mixture was poured into ice water and extracted with ethyl acetate (20 ml). Organic layer was washed with brine, concentrated and chromatographed to yield 5-chloro-2,4-dihydroxybenzaldehyde (0.55 g, 3.2 mmol, 32%) and 3-chloro-2,4-dihydroxybenzaldehyde (0.233 g, 1.34 mmol, 13.4%)

Step 2: Preparation of 5-chloro-2-hydroxy-4-propoxybenzaldehyde

A suspension of 5-chloro-2,4-dihydroxybenzaldehyde (0.517 g, 3.0 mmol), 1-iodopropane (0.501 g, 3 mmol), potassium carbonate (0.414 g, 3.0 mmol), and 18-crown-6 (0.079 g, 0.3 mmol) in acetone (10 ml) was stirred and heated to 70° C. for 15 hours. The mixture was cooled to room temperature and quenched with HCl, aq. 1M. The mixture was extracted with ethyl acetate (30 ml). Organic layer was washed with saturated NaHCO3 aq. (30 ml), water (30 ml) and then with brine (30 ml). Organic layer was dried over MgSO4, concentrated and chromatographed to yield 5-chloro-2-hydroxy-4-propoxybenzaldehyde (0.41 g, 1.91 mmol, 63%).

Step 3: Preparation of 5-(5-chloro-2-hydroxy-4-propoxybenzylidene)pyrimidine-2,4,6(1H,3H,5H)-trione, 20a In a round bottom flask, a mixture of 5-chloro-2-hydroxy-4-propoxybenzaldehyde (0.41 g, 1.91 mmol), barbituric acid (0.256 g, 2.0 mmol), ethanol (15 ml) and water (10 ml) was stirred at room temperature for 5 hours. The reaction mixture was concentrated to reduce volume by 30% by evaporation. After ethanol evaporation, water (20 ml) was added to the reaction mixture. The reaction was stirred at room temperature for 30 minutes and then filtered. Solid yellow cake was collected and vacuum dried at 40° C. to 50° C. to yield compound 20a, (0.59 g, 1.82 mmol, 95%).

Step 4: Preparation of 7-chloro-8-propoxy-2H-chromeno[2,3-d]pyrimidine-2,4(3H)-dione In a scintillation vial, a suspension of compound 20a, (162 mg, 0.5 mmol) in a mixture of acetic acid (2.5 g) and acetic anhydride (0.31 g, 3 mmol) was stirred and heated to 80° C. for 6 hours. The mixture was cooled to room temperature. Yellow solid was filtered, washed with water and vacuum dried at 40° C. to 50° C. to yield compound 20 (126 mg, 0.40 mmol, 80%).

Preparation of 8-(n-hexyloxy)-2H-chromeno[2,3-d]pyrimidine-2,4(3H)-dione

Step 1: Preparation of 4-(n-hexyloxy)-2-hydroxybenzaldehyde

A suspension of 2,4-dihydroxybenzaldehyde (0.828 g, 6.0 mmol), 1-iodohexane (1.40 g, 6.6 mmol), potassium carbonate (0.497 g, 3.6 mmol), and 18-crown-6 (0.158 g, 0.6 mmol) in acetone (15 ml) was stirred and heated to 70° C. for 15 hours. The mixture was cooled to room temperature and quenched with HCl, aq. 1M. The mixture was extracted with ethyl acetate (50 ml). Organic layer was washed with water (50 ml) twice and then with brine (50 ml). Organic layer was dried over MgSO4, concentrated and chromatographed to yield 4-(n-hexyloxy)-2-hydroxybenzaldehyde (0.973 g, 4.38 mmol, 73%).

Step 2: Preparation of 5-(4-(n-hexyloxy)-2-hydroxybenzylidene)pyrimidine-2,4,6(1H,3H,5H)-trione, 21a In a round bottom flask, a mixture of 4-(n-hexyloxy)-2-hydroxybenzaldehyde (0.444 g, 2.0 mmol), barbituric acid (0.256 g, 2.0 mmol), ethanol (15 ml) and water (15 ml) was stirred at room temperature for 3 hours. The reaction mixture was concentrated to reduce volume by 30% by evaporation. After ethanol evaporation, water (30 ml) was added to the reaction mixture. The reaction was stirred at room temperature for 30 minutes and then filtered. Solid yellow cake was collected and vacuum dried at 40° C. to 50° C. to yield compound 21a, (0.564 g, 1.70 mmol, 85%).

Step 3: Preparation of 8-(n-hexyloxy)-2H-chromeno[2,3-d]pyrimidine-2,4(3H)-dione In a scintillation vial, a suspension of compound 21a, (332 mg, 1.0 mmol) in a mixture of acetic acid (3.0 g) and acetic anhydride (0.51 g, 5 mmol) was stirred and heated to 80° C. for 5 hours. The mixture was cooled to room temperature. Yellow solid was filtered, washed with water and vacuum dried at 40° C. to 50° C. to yield compound 21 (148 mg, 0.46 mmol, 46%).

Preparation of 9-chloro-8-ethoxy-2H-chromeno[2,3-d]pyrimidine-2,4(3H)-dione

Step 1: Preparation of 3-chloro-2,4-dihydroxybenzaldehyde

In a scintillation vial, 2,4-dihydroxybenzaldehyde (1.38 g, 10 mmol) was dissolved in ethyl ether (18 ml). The mixture was placed under N2 atmosphere and cooled to 0° C. To the mixture was added sulfuryl chloride (0.91 ml, 11 mmol). The mixture was kept under N2 atmosphere at 0° C. for 30 minutes. The reaction mixture was poured into ice water and extracted with ethyl acetate (20 ml). Organic layer was washed with brine, concentrated and chromatographed to yield 5-chloro-2,4-dihydroxybenzaldehyde (0.55 g, 3.2 mmol, 32%) and 3-chloro-2,4-dihydroxybenzaldehyde (0.233 g, 1.34 mmol, 13.4%)

Step 2: Preparation of 3-chloro-2-hydroxy-4-ethoxybenzaldehyde

A suspension of 3-chloro-2,4-dihydroxybenzaldehyde (0.465 g, 2.7 mmol), iodoethane (0.421 g, 2.7 mmol), potassium carbonate (0.226 g, 1.62 mmol), and 18-crown-6 (0.071 g, 0.27 mmol) in acetone (10 ml) was stirred and heated to 70° C. for 15 hours. The mixture was cooled to room temperature and quenched with HCl, aq. 1M. The mixture was extracted with ethyl acetate (30 ml). Organic layer was washed with saturated NaHCO3 aq. (30 ml), water (30 ml) and then with brine (30 ml). Organic layer was dried over MgSO4, concentrated and chromatographed to yield 3-chloro-2-hydroxy-4-ethoxybenzaldehyde (0.217 g, 1.08 mmol, 40%) and 3-chloro-2,4-diethoxybenzaldehyde (0.057 g, 0.25 mmol, 9.4%).

Step 3: Preparation of 5-(3-chloro-4-ethoxy-2-hydroxybenzylidene)pyrimidine-2,4,6(1H,3H,5H)-trione, 22a In a round bottom flask, a mixture of 3-chloro-2-hydroxy-4-ethoxybenzaldehyde (0.217 g, 1.08 mmol), barbituric acid (0.139 g, 1.08 mmol), ethanol (10 ml) and water (10 ml) was stirred at room temperature for 10 hours. The reaction mixture was concentrated to reduce volume by 30% by evaporation. After ethanol evaporation, water (20 ml) was added to the reaction mixture. The reaction was stirred at room temperature for 30 minutes and then filtered. Solid yellow cake was collected and vacuum dried at 40° C. to 50° C. to yield compound 22a, (0.30 g, 0.97 mmol, 90%).

Step 4: Preparation of 9-chloro-8-ethoxy-2H-chromeno[2,3-d]pyrimidine-2,4(3H)-dione In a scintillation vial, a suspension of compound 22a, (155 mg, 0.5 mmol) in a mixture of acetic acid (1.5 g) and acetic anhydride (0.306 g, 3 mmol) was stirred and heated to 80° C. for 16 hours. The mixture was cooled to room temperature. Yellow solid was filtered, washed with water and vacuum dried at 40° C. to 50° C. to yield compound 22 (127 mg, 0.40 mmol, 80%).

Preparation of 8-isobutoxy-2H-chromeno[2,3-d]pyrimidine-2,4(3H)-dione

Step 1: Preparation of 2-hydroxy-4-isobutoxybenzaldehyde

A suspension of 2,4-dihydroxybenzaldehyde (0.76 g, 5.5 mmol), 1-iodo-2-methylpropane (1.196 g, 6.5 mmol), potassium carbonate (0.828 g, 6.0 mmol), and 18-crown-6 (0.132 g, 0.5 mmol) in acetone (10 ml) was stirred and heated to 70° C. for 3 days. The mixture was cooled to room temperature and quenched with HCl, aq. 1M. The mixture was extracted with ethyl acetate (50 ml). Organic layer was washed with water (50 ml) twice and then with brine (50 ml). Organic layer was dried over MgSO4, concentrated and chromatographed to yield 2-hydroxy-4-isobutoxybenzaldehyde (0.425 g, 2.2 mmol, 40%).

Step 2: Preparation of 5-(2-hydroxy-4-isobutoxybenzylidene)pyrimidine-2,4,6(1H,3H,5H)-trione, 23a In a round bottom flask, a mixture of 2-hydroxy-4-isobutoxybenzaldehyde (0.388 g, 2.0 mmol), barbituric acid (0.256 g, 2.0 mmol), ethanol (5 ml) and water (10 ml) was stirred at room temperature for 5 hours. The reaction mixture was concentrated to reduce volume by 30% by evaporation. After ethanol evaporation, water (30 ml) was added to the reaction mixture. The reaction was stirred at room temperature for 30 minutes and then filtered. Solid yellow cake was collected and vacuum dried at 40° C. to 50° C. to yield compound 23a, (0.563 g, 1.85 mmol, 92%).

Step 3: Preparation of 8-isobutoxy-2H-chromeno[2,3-d]pyrimidine-2,4(3H)-dione In a scintillation vial, a suspension of compound 23a, (152 mg, 0.5 mmol) in a mixture of acetic acid (1.5 g) and acetic anhydride (0.31 g, 3 mmol) was stirred and heated to 80° C. for 6 hours. The mixture was cooled to room temperature. Yellow solid was filtered, and chromatographed (MeOH:DCM, 5:95) to yield compound 23 (17 mg, 0.06 mmol, 12%).

Preparation of 3-(n-butyl)-8-ethoxy-2H-chromeno[2,3-d]pyrimidine-2,4(3H)-dione

Step 1: Preparation of 1-butylpyrimidine-2,4,6(1H,3H,5H)-trione

In a round bottom flask, dimethyl malonate (6.60 g, 50 mmol) was added to a mixture of n-Butyl urea (5.80 g, 50 mmol) and sodium ethoxide (21% in ethanol, 19.43 g, 60 mmol). Upon the addition of dimethyl malonate, the reaction mixture was placed under nitrogen and heated to reflux. After 1 hour at reflux, the reaction mixture turned a viscous suspension. Ethanol (15 ml) was added into the mixture. The mixture was stirred at reflux for a total reaction time of 18 hours. At the end of the reaction, solid was filtered (crop 1). Filtrate was collected and concentrated to cause precipitation. The second crop of solid was filtered. Combined solid crop 1 and crop 2 was dissolved in water (100 ml) and acidified with HCl, aq. 1M to cause precipitation of desired product. Filtrate residue from crop 2 was concentrate and chromatographed to yield desired product. Combined desired product (7.103 g, 38 mmol, 77%) was vacuum dried.

Step 2: Preparation of 1-butyl-5-(4-ethoxy-2-hydroxybenzylidene)pyrimidine-2,4,6(1H,3H,5H)-trione, 24a In a round bottom flask, a mixture of 2-hydroxy-4-ethoxybenzaldehyde (0.498 g, 3.0 mmol), 1-butylpyrimidine-2,4,6(1H,3H,5H)-trione (0.555 g, 5.0 mmol), ethanol (10 ml) and water (10 ml) was stirred at room temperature for 15 hours. The reaction mixture was concentrated to reduce volume by 30% by evaporation. After ethanol evaporation, water (30 ml) was added to the reaction mixture. The reaction was stirred at room temperature for 30 minutes and then filtered. Solid yellow cake was collected, washed with a mixture of ethyl acetate:hexane (20:80) and vacuum dried at 40° C. to 50° C. to yield compound 24a, (0.7939 g, 1.39 mmol, 80%).

Step 3: Preparation of 3-(n-butyl)-8-ethoxy-2H-chromeno[2,3-d]pyrimidine-2,4(3H)-dione In a scintillation vial, a suspension of compound 24a, (0.498 mg, 0.5 mmol) in a mixture of acetic acid (3.5 g) and acetic anhydride (0.765 g, 7.5 mmol) was stirred and heated to 80° C. for 15 hours. The mixture became homogeneous after 15 minutes at 80° C. The mixture was cooled to room temperature. Yellow solid was filtered, and chromatographed (MeOH:DCM, 5:95) to yield compound 24 (102 mg, 0.32 mmol, 21%).

Preparation of 7-chloro-8-propyl-2H-chromeno[2,3-d]pyrimidine-2,4(3H)-dione

Step 1: Preparation of 4-chloro-3-propylphenol

In a scintillation vial, 3-n-Propylphenol (1.36 g, 10 mmol) was dissolved in ethyl ether (10 ml). The mixture was cooled with ice/brine bath. To the mixture was added sulfuryl chloride (0.91 ml, 11 mmol) over 2 minutes. The mixture remained at −10° C. to 0° C. for an hour. The mixture was quenched with water and extracted with ethyl acetate. The organic layer was concentrated and chromatographed to yield 4-chloro-3-propylphenol (1.156 g, 6.8 mmol, 68%), 2-chloro-3-propylphenol (0.097 g, 0.57 mmol, 5.7%) and 6-chloro-3-propylphenol (0.156 g, 0.92 mmol, 9.2%).

Step 2: Preparation of 5-chloro-2-hydroxy-4-propylbenzaldehyde

In a scintillation vial, a mixture of 4-chloro-3-propylphenol (0.857 g, 5 mmol), magnesium chloride anhydrous (0.712 g, 7.5 mmol), paraformaldehyde (0.90 g, 30 mmol), and triethyl amine (1.01 g, 10 mmol) in acetonitrile anhydrous (10 ml) was heated to 70° C. for 15 hours. The reaction mixture was cooled to room temperature and then filtered. The white cake was washed with HCl aq. 1M (50 ml) and ethyl acetate (80 ml). Filtrate was decanted. Organic layer was separated and washed with brine. Organic layer was concentrate and chromatographed to yield 5-chloro-2-hydroxy-4-propylbenzaldehyde (0.612 g, 3.1 mmol, 61%).

Step 3: Preparation of 5-(5-chloro-2-hydroxy-4-propylbenzylidene)pyrimidine-2,4,6(1H,3H,5H)-trione In a round bottom flask, a mixture of 5-chloro-2-hydroxy-4-propylbenzaldehyde (0.397 g, 2.0 mmol), barbituric acid (0.256 g, 2.0 mmol), ethanol (10 ml) and water (10 ml) was stirred at room temperature for 15 hours. The reaction mixture was concentrated to reduce volume by 30% by evaporation. After ethanol evaporation, water (40 ml) was added to the reaction mixture. The reaction was stirred at room temperature for 30 minutes and then filtered. Solid yellow cake was washed with ethyl acetate:hexane (5:95), collected and vacuum dried at 40° C. to 50° C. to yield compound 25a, (0.41 g, 1.32 mmol, 66%).

Step 4: Preparation of 7-chloro-8-propyl-2H-chromeno[2,3-d]pyrimidine-2,4(3H)-dione In a scintillation vial, a suspension of compound 25a, (0.308 mg, 1.0 mmol) in a mixture of acetic acid (2.5 g) and acetic anhydride (0.612 g, 6.0 mmol) was stirred and heated to 80° C. for 6 hours. The mixture was cooled to room temperature and allowed to sit overnight. Yellow solid was filtered, dried at 40° C. to 50° C. to yield compound 25 (250 mg, 0.86 mmol, 86%).

Preparation of 3-butyl-7-chloro-8-ethoxy-2H-chromeno[2,3-d]pyrimidine-2,4(3H)-dione

Step 1: Preparation of 1-butyl-5-(5-chloro-4-ethoxy-2-hydroxybenzylidene)pyrimidine-2,4,6(1H,3H,5H)-trione, 26a In a round bottom flask, a mixture of 5-chloro-4-ethoxy-2-hydroxybenzaldehyde (0.295 g, 1.475 mmol), barbituric acid (0.192 g, 1.5 mmol), ethanol (20 ml) and water (10 ml) was stirred at room temperature for 3.5 hours. The reaction mixture was concentrated to reduce volume by 30% by evaporation. After ethanol evaporation, water (50 ml) was added to the reaction mixture. The reaction was stirred at room temperature for 30 minutes and then filtered. Solid orange cake was collected and vacuum dried at 40° C. to 50° C. to yield compound 26a, (0.463 g, 1.26 mmol, 85%).

Step 2: Preparation of 3-butyl-7-chloro-8-ethoxy-2H-chromeno[2,3-d]pyrimidine-2,4(3H)-dione, compound 26

In a scintillation vial, a suspension of compound 26a, (0.367 mg, 1.0 mmol) in a mixture of acetic acid (2.5 g) and acetic anhydride (0.51 g, 5.0 mmol) was stirred and heated to 80° C. for 15 hours. The mixture was cooled to room temperature and allowed to sit overnight. Yellow solid was filtered, dried at 40° C. to 50° C. to yield compound 26 (278 mg, 0.80 mmol, 80%).

Preparation of 7-fluoro-8-methyl-2H-chromeno[2,3-d]pyrimidine-2,4(3H)-dione

Step 1: Preparation of 5-fluoro-2-hydroxy-4-methylbenzaldehyde, 27a

In a scintillation vial, a suspension of 4-fluoro-3-methylphenol, (1.26 g, 10.0 mmol), $MgCl_2$ anhydrous (1.42 g, 15 mmol), paraformaldehyde (1.50 g, 50 mmol) and triethylamine (2.02 g, 20 mmol) in acetonitrile anhydrous (15 ml) was stirred and heated to 70° C. for 8 hours. The mixture was cooled to room temperature, quenched with HCl, aq. 1M (20 ml) and extract with ethyl acetate. The organic layer was dried with $MgSO4$, filtered over silica gel, concentrated and chromatographed to yield compound 27a (1.05 g, 6.8 mmol, 68%).

Step 2: Preparation of 5-(5-fluoro-2-hydroxy-4-methylbenzylidene)pyrimidine-2,4,6(1H,3H,5H)-trione In a round bottom flask, a mixture of 27a (0.308 g, 2.0 mmol), barbituric acid (0.256 g, 2.0 mmol), ethanol (10 ml) and water (10 ml) was stirred at room temperature for 5 hours After 5 hours of reaction, water (50 ml) was added to the reaction mixture. The reaction was stirred at room temperature for 30 minutes and then filtered. Solid yellow cake was collected and vacuum dried at 40° C. to 50° C. to yield compound 27b, (0.3424 g, 1.29 mmol, 65%).

Step 3: Preparation of 7-fluoro-8-methyl-2H-chromeno[2,3-d]pyrimidine-2,4(3H)-dione In a scintillation vial, a suspension of compound 27b, (0.264 mg, 1.0 mmol) in a mixture of acetic acid (4 ml) and acetic anhydride (0.51 g, 5.0 mmol) was stirred and heated to 80° C. for 5 hours. The mixture was cooled to room temperature and allowed to sit overnight. Yellow solid was filtered, dried at 40° C. to 50° C. to yield compound 27 (189 mg, 0.77 mmol, 77%).

Preparation of 8-ethoxy-7-fluoro-2H-chromeno[2,3-d]pyrimidine-2,4(3H)-dione

Step 1: Preparation of 3-ethoxy-4-fluorophenol, 28a

In a scintillation vial, a mixture of 4-fluororesorcinal (0.512 g, 4.0 mmol), $K2CO3$ (0.607 g, 4.4 mmol), 18-crown-6 (0.106 g, 0.4 mmol), iodoethane (0.686 g, 4.4 mmol) in acetone (5 ml) was heated to 50° C. overnight. The mixture was cooled to room temperature, quenched with HCl aq. 1M (20 ml), extracted with ethyl acetate (30 ml). Organic layer was concentrated and chromatographed to yield 28a (0.349 g, 2.34 mmol, 56%).

Step 2: Preparation of 4-ethoxy-5-fluoro-2-hydroxybenzaldehyde, 28b

In a scintillation vial, a suspension of 28a, (0.68 g, 4.3 mmol), MgCl2 anhydrous (0.613 g, 6.45 mmol), paraformaldehyde (0.774 g, 25.8 mmol) and triethylamine (0.868 g, 8.6 mmol) in acetonitrile anhydrous (10 ml) was stirred and heated to 70° C. for 4 hours. The mixture was cooled to room temperature, quenched with HCl, aq. 1M (20 ml) and extract with ethyl acetate (30 ml). The organic layer was dried with MgSO4, filtered over silica gel, concentrated and chromatographed to yield compound 28b (0.70 g, 3.48 mmol, 81%).

Step 3: Preparation of 5-(4-ethoxy-5-fluoro-2-hydroxybenzylidene)pyrimidine-2,4,6(1H,3H,5H)-trione, 28c In a round bottom flask, a mixture of 28b (0.184 g, 1.0 mmol), barbituric acid (0.128 g, 1.0 mmol), ethanol (10 ml) and water (10 ml) was stirred at room temperature for 6 hours After 6 hours of reaction, water (50 ml) was added to the reaction mixture. The reaction was stirred at room temperature for 30 minutes and then filtered. Solid yellow cake was collected and vacuum dried at 40° C. to 50° C. to yield compound 28c, (0.263 g, 0.89 mmol, 89%).

Step 4: Preparation of 8-ethoxy-7-fluoro-2H-chromeno[2,3-d]pyrimidine-2,4(3H)-dione In a scintillation vial, a suspension of compound 28c, (0.147 mg, 0.5 mmol) in a mixture of acetic acid (2 ml) and acetic anhydride (0.204 g, 2 mmol) was stirred and heated to 80° C. for 4 hours. The mixture was cooled to room temperature and allowed to sit overnight. Yellow solid was filtered, dried at 40° C. to 50° C. to yield compound 28 (130 mg, 0.48 mmol, 96%).

Synthesis of compounds 29 to 36 follow the same protocol described for compound 28.

Synthesis of compounds 37 to 38 follow the same protocol described for compound 20.

Synthesis of compounds 39 to 48 follow the same protocol described for compound 22.

8-ethoxy-2H-thiochromeno[2,3-d]pyrimidine-2,4(3H)-dione

Preparation of 8-ethoxy-2H-thiochromeno[2,3-d]pyrimidine-2,4(3H)-dione

Step 1, Preparation of 2,4-dichloro-6-((3-ethoxyphenyl)thio)pyrimidine-5-carbaldehyde, 49a In a scintillation vial, 2,4,6-trichloropyrimidine carboxaldehyde (0.422 g, 2 mmol) was dissolved in anhydrous THF (5 ml). The mixture was cooled to −30° C. To the cold mixture was added triethyl amine (0.242 g, 2.4 mmol) and 3-ethoxybenzenethiol (0.308 g, 2 mmol). The mixture was maintained at −30° C. for 3 hours. After 3 hours, the mixture was filtered. Cake was rinsed with ethyl ether. Filtrate contains desired product was concentrated. Product was crystallized on siting under nitrogen stream. Yellow pale solid was filtered and dried under vacuum to yield 49a (0.331 g, 1.0 mmol, 50%).

Step 2, Preparation of 8-ethoxy-2H-thiochromeno[2,3-d]pyrimidine-2,4(3H)-dione In a scintillation vial, compound 49a (0.331 g, 1.0 mmol) was slowly and carefully added to concentrate 98% H2SO4 (4 ml). The mixture was stirred at room temperature overnight. To the mixture was added EtOAc (25 ml) and water (25 ml). Precipitation occurred. Orange solid was filtered, washed with water and vacuum dried to yield compound 49 (0.137 g, 0.5 mmol, 50%).

Synthesis of compounds 50-52 follow the same protocol described for compound 22.

6-((9-chloro-2,4-dioxo-3,4-dihydro-2H-chromeno[2,3-d]pyrimidin-8-yl)oxy)hexanoic acid

Step 1, Preparation of methyl 6-(2-chloro-4-formyl-3-hydroxyphenoxy)hexanoate, 53a In a scintillation vial, a suspension of 3-chloro-2,4-dihydroxybenzaldehyde (0.69 g, 4 mmol), K2CO3 (0.552 g, 4.0 mmol), 18-crown-6 (0.106 g, 0.4 mmol) and methyl 6-bromohexanoate (0.919 g, 4.4 mmol) in acetone (5 ml) was heated and stirred overnight at 65° C. The reaction mixture was cooled to room temperature, acidified with HCl, aq. 1M and extracted with ethyl acetate (50 ml), twice. Organic layer was washed with water (50 ml) twice and then with brine (50 ml). Organic layer was dried over MgSO4, concentrated and chromatographed to yield compound 53a (0.25 g, 0.83 mmol, 20.7%).

Step 2, Preparation of 6-(2-chloro-4-formyl-3-hydroxyphenoxy)hexanoic acid, 53b A mixture of compound 53a (0.25 g, 0.83 mmol) in MeOH (3 ml) and NaOH aq. 1M (5 ml) was warmed to 60° C. for 2 hours. The mixture was cooled to room temperature. To the mixture was added HCl, aq. 1M (8 ml) and then extracted with ethyl acetate (20 ml). Organic layer was dried over MgSO4, concentrated and chromatographed to yield compound 53b (0.192 g, 0.67 mmol, 81%).

Step 3, Preparation of 6-(2-chloro-3-hydroxy-4-((2,4,6-trioxotetrahydropyrimidin-5(2H)-ylidene)methyl)phenoxy)hexanoic acid, 53c In a round bottom flask, a mixture of compound 53b (0.192 g, 0.67 mmol), barbituric acid (0.103 g, 0.8 mmol), iPrOH (6 ml) and water (6 ml) was stirred at room temperature for 24 hours. Water (30 ml) was added to the reaction mixture. The reaction was stirred at room temperature for 30 minutes and then filtered. Solid yellow cake was collected and vacuum dried at 40° C. to 50° C. to yield compound 53c, (0.22 g, 0.55 mmol, 83%).

Step 4, Preparation of 6-((9-chloro-2,4-dioxo-3,4-dihydro-2H-chromeno[2,3-d]pyrimidin-8-yl)oxy)hexanoic acid In a scintillation vial, a suspension of compound 53c, (0.22 g, 0.55 mmol) in a mixture of acetic acid (1.62 g) and acetic anhydride (0.283 g) was stirred and heated to 80° C. for 2 days. The mixture was cooled to room temperature and sit for 3 hours. Yellow solid was filtered, washed with water and vacuum dried at 40° C. to 50° C. to yield compound 53 (161 mg, 0.43 mmol, 78%).

Synthesis of compounds 54-59 follow the same protocol described for compound 53.

4-((9-chloro-2,4-dioxo-3,4-dihydro-2H-chromeno[2,3-d]pyrimidin-8-yl)oxy)butyl acetate

Step 1, 6-(2-chloro-4-formyl-3-hydroxyphenoxy)butyl acetate, 60a

In scintillation vial, a suspension of 3-chloro-2,4-dihydroxybenzaldehyde (0.5175 g, 3 mmol), KHCO$_3$ (0.49 g, 4.9 mmol), NaI (0.45 g, 3 mmol), 18-crown-6 (0.132 g, 0.5 mmol) and methyl 6-bromobutanoate (0.585 g, 3.0 mmol) in acetone (5 ml) was heated and stirred for 4 days at 70° C. The reaction mixture was cooled to room temperature, acidified with HCl, aq. 1M and extracted with ethyl acetate (25 ml). Organic layer was washed with water (25 ml) and then with brine (25 ml). Organic layer was dried over MgSO$_4$, concentrated and chromatographed to yield compound 60a (0.182 g, 0.64 mmol, 21.2%).

Step 2, Preparation of 4-(2-chloro-3-hydroxy-4-((2,4,6-trioxotetrahydropyrimidin-5(2H)-ylidene)methyl)phenoxy)butyl acetate, 60b In a scintillation vial, a mixture of compound 60a (0.182 g, 0.64 mmol), barbituric acid (0.089 g, 0.7 mmol), iPrOH (3 ml) and water (3 ml) was stirred at room temperature for 24 hours. Water (10 ml) was added to the reaction mixture. The reaction was stirred at room temperature for 10 minutes and then filtered. Solid yellow cake was collected and vacuum dried at 40° C. to 50° C. to yield compound 60b, (0.209 g, 0.53 mmol, 82%).

Step 3, Preparation of 4-((9-chloro-2,4-dioxo-3,4-dihydro-2H-chromeno[2,3-d]pyrimidin-8-yl)oxy)butyl acetate In a scintillation vial, a suspension of compound 60b, (0.209 g, 0.55 mmol) in a mixture of acetic acid (1.65 g) and acetic anhydride (0.281 g) was stirred and heated to 80° C. for 4.5 hours. The mixture was cooled to room temperature and sit for 3 hours. Yellow solid was filtered, dried at 40° C. to 50° C. to yield compound 60 (108 mg, 0.28 mmol, 52%).

8-(2-(2-methoxyethoxy)ethoxy)-2H-chromeno[2,3-d]pyrimidine-2,4(3H)-dione

Step 1, Preparation of 2-hydroxy-4-(2-(2-methoxyethoxy)ethoxy)benzaldehyde, 61a In scintillation vial, a suspension of 2,4-dihydroxybenzaldehyde (0.552 g, 4 mmol), K$_2$CO$_3$ (0.552 g, 4.0 mmol), 18-crown-6 (0.106 g, 0.4 mmol) and 1-bromo-2-(2-methoxyethoxy) ethane (90-95% purity, 0.61 g, 3.0 mmol) in acetone (5 ml) was heated and stirred overnight at 80° C. The reaction mixture was cooled to room temperature, acidified with HCl, aq. 1M and extracted with ethyl acetate (25 ml). Organic layer was washed with water (25 ml) and then with brine (25 ml). Organic layer was dried over MgSO$_4$, concentrated and chromatographed to yield compound 61a (0.35 g, 1.46 mmol, 36.4%).

Step 2, Preparation of 5-(2-hydroxy-4-(2-(2-methoxyethoxy)ethoxy)benzylidene)pyrimidine-2,4,6(1H,3H,5H)-trione, 61b In a scintillation vial, a mixture of compound 61a (0.35 g, 1.46 mmol), barbituric acid (0.224 g, 1.75 mmol), ethanol (10 ml) and water (10 ml) was stirred and warmed to 40 to 50° C. for 15 minutes and them stirred at room temperature overnight. Water (30 ml) was added to the reaction mixture. The reaction was stirred at room temperature for 15 minutes and then filtered. Solid yellow cake was collected and vacuum dried at 40° C. to 50° C. to yield compound 61b, (0.434 g, 1.24 mmol, 85%).

Step 3, Preparation of 8-(2-(2-methoxyethoxy)ethoxy)-2H-chromeno[2,3-d]pyrimidine-2,4(3H)-dione In a scintillation vial, a suspension of compound 61b, (0.263 g, 0.75 mmol) in a mixture of acetic acid (2.25 g) and acetic anhydride (0.383 g) was stirred and heated to 80° C. for 6 hours. The mixture was concentrated to remove ~50% of its volume and then cooled to room temperature and sit for 3 hours. Yellow solid was filtered, dried at 40° C. to 50° C. to yield compound 61 (189 mg, 0.57 mmol, 76%).

Synthesis of compounds of example 62-65 follow the same protocol described for compound 61.

9-chloro-8-(4-methoxybutoxy)-2H-chromeno[2,3-d]pyrimidine-2,4(3H)-dione

Step 1, Preparation of 3-chloro-2-hydroxy-4-(4-methoxybutoxy)benzaldehyde, 66a In scintillation vial, a suspension of 3-chloro-2,4-dihydroxybenzaldehyde (1.725 g, 10 mmol), K$_2$CO$_3$ (1.38 g, 10 mmol), 18-crown-6 (0.264 g, 1.0 mmol) and 1-bromo-4-methoxybutane (0.835 g, 5.0 mmol) in acetone (10 ml) was heated and stirred overnight at 70° C. The reaction mixture was cooled to room temperature, acidified with HCl, aq. 1M and extracted with ethyl acetate (50 ml). Organic layer was washed with water (50 ml) and then with brine (50 ml). Organic layer was dried over MgSO$_4$, concentrated and chromatographed to yield compound 66a (0.898 g, 3.47 mmol, 34.7%).

Step 2, Preparation of 5-(3-chloro-2-hydroxy-4-(4-methoxybutoxy)benzylidene)pyrimidine-2,4,6(1H,3H,5H)-trione, 66b In a round bottom flash, a mixture of compound 66a (0.498 g, 1.5 mmol), barbituric acid (0.256 g, 2.0 mmol), ethanol (6 ml) and water (6 ml) was stirred at room temperature overnight. Water (15 ml) was added to the reaction mixture. The reaction was stirred at room temperature for 15 minutes and then filtered. Solid yellow cake was collected and vacuum dried at 40° C. to 50° C. to yield compound 66b, (0.466 g, 1.34 mmol, 89.6%).

Step 3, Preparation of 9-chloro-8-(4-methoxybutoxy)-2H-chromeno[2,3-d]pyrimidine-2,4(3H)-dione In a scintillation vial, a suspension of compound 66b, (0.369 g, 1.0 mmol) in a mixture of acetic acid (2.1 g) and acetic anhydride (0.51 g) was stirred and heated to 80 to 90° C. overnight. The mixture was concentrated to remove ~50% of its volume and then cooled to room temperature and sit for 3 hours. Yellow solid was filtered, dried at 40° C. to 50° C. to yield compound 66 (300 mg, 0.86 mmol, 86%).

Synthesis of compounds of example 67-70 follow the same protocol described for compound 66.

Synthesis of compounds 71-74 follow the same protocol described for compound 75, below.

7-fluoro-8-(3-(2-methoxyethoxy)propoxy)-2H-chromeno[2,3-d]pyrimidine-2,4(3H)-dione Step 1, Preparation of 4-fluoro-3-(3-(2-methoxyethoxy)propoxy)phenol, 75a In scintillation vial, a suspension of 4-fluororesorcinol (1.28 g, 10 mmol), $K_2CO_3$ (1.38 g, 10 mmol), 18-crown-6 (0.264 g, 1.0 mmol) and 1-bromo-3-(2-methoxyethoxy)propane (0.985 g, 5.0 mmol) in acetone (10 ml) was heated and stirred overnight at 70° C. The reaction mixture was cooled to room temperature, acidified with HCl, aq. 1M and extracted with ethyl acetate (50 ml). Organic layer was washed with water (50 ml) and then with brine (50 ml). Organic layer was dried over $MgSO_4$, concentrated and chromatographed to yield compound 75a (0.921 g, 3.74 mmol, 37.4%).

Step 2, Preparation of 5-fluoro-2-hydroxy-4-(3-(2-methoxyethoxy)propoxy)benzaldehyde, 75b In a scintillation vial, a suspension of compound 75a, (0.478 g, 1.96 mmol), $MgCl_2$ anhydrous (0.279 g, 2.93 mmol), paraformaldehyde (0.12 g, 4 mmol) and triethylamine (0.296 g, 2.93 mmol) in acetonitrile anhydrous (5 ml) was stirred and heated to 60° C. for 2 hours. The mixture was cooled to room temperature, quenched with HCl, aq. 1M (15 ml) and extract with ethyl acetate. The organic layer was dried with $MgSO_4$, filtered over silica gel, concentrated and chromatographed to yield compound 75b (0.34 g, 1.25 mmol, 64%).

Step 3, Preparation of 5-(5-fluoro-2-hydroxy-4-(3-(2-methoxyethoxy)propoxy)benzylidene)pyrimidine-2,4,6(1H,3H,5H)-trione, 75c In a round bottom flash, a mixture of compound 75b (0.140 g, 0.51 mmol), barbituric acid (0.079 g, 0.62 mmol), ethanol (3 ml) and water (3 ml) was stirred at room temperature overnight. Water (15 ml) was added to the reaction mixture. The reaction was stirred at room temperature for 15 minutes and then filtered. Solid yellow cake was collected and vacuum dried at 40° C. to 50° C. to yield compound 75c, (0.189 g, 0.49 mmol, 97%).

Step 4, Preparation of 7-fluoro-8-(3-(2-methoxyethoxy)propoxy)-2H-chromeno[2,3-d]pyrimidine-2,4 (3H)-dione In a scintillation vial, a suspension of compound 75c, (0.172 g, 0.45 mmol) in a mixture of acetic acid (1.58 g) and acetic anhydride (0.226 g) was stirred and heated to 80 to 90° C. for 5 hours. The mixture was concentrated to remove ~50% of its volume and then cooled to room temperature and sit for 3 hours. Yellow solid was filtered, washed with water and vacuum dried at 40° C. to 50° C. to yield compound 75 (144 mg, 0.39 mmol, 88%).

NMR Spectroscopy

NMR spectroscopy was performed using standard Bruker® 400 MHz NMR.

| Cmpd. | Structure | MW | 1H NMR, 400 MHz, DMSO-d6 |
|---|---|---|---|
| 1 | 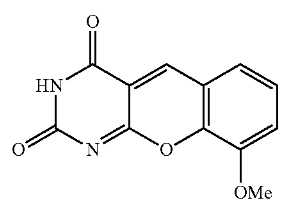 [SMILES: COc1cccc2cc3c(=O)[nH]c(=O)nc-3oc12] | 244 | 3.99 (s, 3H), 7.48 (dd, J = 7.92, 7.92 Hz, 1H), 7.58-7.63 (m, 2H), 8.92 (s, 1H), 11.46 (s, 1H) |
| 2 | 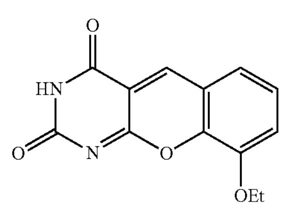 [SMILES: CCOc1cccc2cc3c(=O)[nH]c(=O)nc-3oc12] | 258 | 1.44 (t, J = 7.00 Hz, 3H), 4.26 (q, J = 7.00 Hz, 2H), 7.46 (dd, J = 7.92, 7.92 Hz, 1H), 7.57-7.63 (m, 2H), 8.92 (s, 1H), 11.47 (s, 1H) |
| 3 | 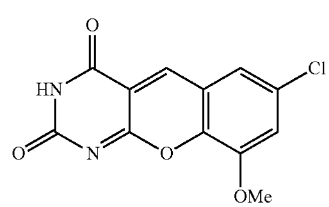 [SMILES: COc1cc(Cl)cc2cc3c(=O)[nH]c(=O)nc-3oc12] | 279 | 4.02 (s, 3H), 7.65 (d, J = 2.30 Hz, 1H), 7.73 (d, J = 2.30 Hz, 1H), 8.85 (s, 1H), 11.53 (s, 1H) |

| Cmpd. | Structure | MW | 1H NMR, 400 MHz, DMSO-d6 |
|---|---|---|---|
| 4 | 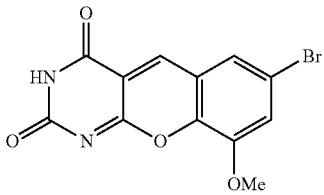 | 323 | 4.01 (s, 3H), 7.73 (d, J = 2.14 Hz, 1H), 7.87 (d, J = 2.14 Hz, 1H), 8.83 (s, 1H), 11.52 (s, 1H) |
| 5 | 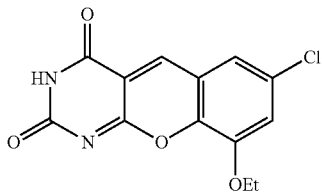 [SMILES: CCOc1cc(Cl)cc2cc3c(=O)[nH]c(=O)nc-3oc12] | 293 | 1.43 (t, J = 7.00 Hz, 3H), 4.28 (q, J = 7.00 Hz, 2H), 7.63 (d, J = 2.28 Hz, 1H), 7.72 (d, J = 2.28 Hz, 1H), 8.84 (s, 1H), 11.53 (s, 1H) |
| 6 | 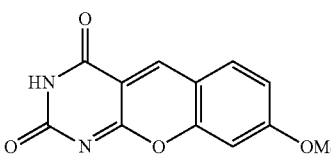 | 244 | 3.91 (s, 3H), 7.11 (dd, J = 8.88, 2.65 Hz, 1H), 7.28 (d, J = 2.65 Hz, 1H), 7.95 (d, J = 8.88 Hz, 1H), 8.83 (s, 1H), 11.28 (s, 1H) |
| 7 | 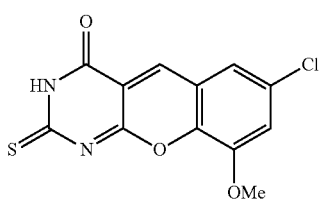 [SMILES: COc1cc(Cl)cc2cc3c(=O)[nH]c(=S)nc-3oc12] | 295 | 4.00 (s, 3H), 7.65 (d, J = 2.30 Hz, 1H), 7.73 (d, J = 2.30 Hz, 1H), 9.01 (s, 1H), 12.63 (s, 1H) |
| 8 | 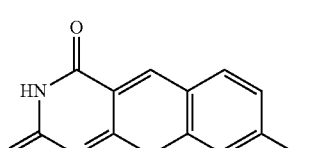 | 260 | 4.00 (s, 3H), 7.24 (dd, J = 8.86, 2.43 Hz, 1H), 7.88 (d, J = 2.43 Hz, 1H), 8.06 (d, J = 8.86 Hz, 1H), 9.01 (s, 1H), 12.62 (s, 1H) |
| 9 | 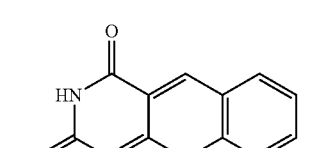 | 214 | 7.56 (ddd, J = 8.30, 7.60, 1.00 Hz, 1H), 7.71 (d, J = 8.30 Hz, 1H), 7.90 (ddd, J = 8.40, 7.30, 1.50 Hz, 1H), 8.09 (dd, J = 8.80, 1.50 Hz, 1H), 8.95 (s, 1H), 11.46 (s, 1H) |
| 10 | 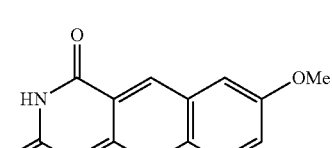 | 244 | 3.86 (s, 3H), 7.50 (dd, J = 9.12, 3.08 Hz, 1H), 7.65 (d, J = 3.08 Hz, 1H), 7.68 (d, J = 8.00 Hz, 1H), 8.88 (s, 1H), 11.43 (s, 1H) |
| 11 | 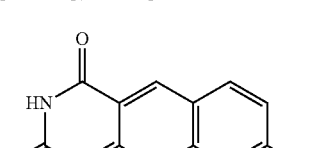 | 230 | 6.98 (d, J = 2.04 Hz, 1H), 7.00 (dd, J = 8.55, 2.04 Hz, 1H), 7.93 (d, J = 8.60 Hz, 1H), 8.84 (s, 1H), 11.27 (s, 1H), 11.62 (bs, 1H) |
| 12 | 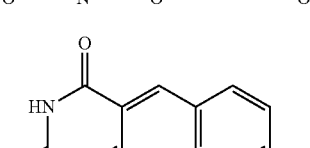 | 228 | 2.60 (s, 3H), 7.49 (dd, J = 8.00, 0.85 Hz, 1H), 7.65 (d, J = 0.85 Hz, 1H), 8.05 (d, J = 8.00 Hz, 1H), 9.00 (s, 1H), 11.49 (s, 1H) |

| Cmpd. | Structure | MW | 1H NMR, 400 MHz, DMSO-d6 |
|---|---|---|---|
| 13 | (chromeno-pyrimidine-2,4-dione with 7-OEt) | 258 | 1.32 (t, J = 6.94 Hz, 3H), 4.19 (q, J = 6.94 Hz, 2H), 7.09 (dd, J = 8.78, 2.50 Hz, 1H), 7.25 (d, J = 2.50 Hz, 1H), 7.93 (d, J = 8.78 Hz, 1H), 8.81 (s, 1H), 11.26 (s, 1H) |
| 14 | (chromeno-pyrimidine-2,4-dione with 6-OMe, 8-OMe) | 274 | 3.98 (s, 3H), 4.01 (s, 3H), 6.71 (d, J = 1.67 Hz, 1H), 6.99 (d, J = 1.67 Hz, 1H), 8.61 (s, 1H), 11.30 (s, 1H) |
| 15 | (2-thioxo-chromeno-pyrimidin-4-one with 7-OMe) | 260 | 3.87 (s, 3H), 7.59 (dd, J = 9.13, 3.02 Hz, 1H), 7.68 (d, J = 3.02 Hz, 1H), 7.73 (d, J = 9.13 Hz, 1H), 8.98 (s, 1H), 12.70 (s, 1H) |
| 16 | (2-thioxo-chromeno-pyrimidin-4-one with 7-OH) | 246 | 7.22 (d, J = 2.00 Hz, 1H), 7.27 (dd, J = 8.70, 2.10 Hz, 1H), 8.19 (d, J = 8.80 Hz, 1H), 9.17 (s, 1H), 12.11 (bs, 1H), 12.77 (s, 1H) |
| 17 | (2-thioxo-chromeno-pyrimidin-4-one with 7-Me) | 244 | 2.45 (s, 3H), 7.37 (dd, J = 8.17, 1.00 Hz, 1H), 7.53 (d, J = 1.00 Hz, 1H), 7.92 (d, J = 8.17 Hz, 1H), 8.94 (s, 1H), 12.61 (s, 1H) |
| 18 | (2-thioxo-chromeno-pyrimidin-4-one with 6-OMe, 8-OMe) | 290 | 3.94 (s, 3H), 3.95 (s, 3H), 6.68 (d, J = 2.01 Hz, 1H), 6.90 (d, J = 2.01 Hz, 1H), 8.60 (s, 1H), 12.53 (s, 1H) |
| 19 | (chromeno-pyrimidine-2,4-dione with 7-OnPr) | 272 | 0.81 (t, J = 7.42 Hz, 3H), 1.55-1.63 (m, 2H), 3.97 (t, J = 6.55 Hz, 2H), 6.97 (dd, J = 8.81, 2.40 Hz, 1H), 7.13 (d, J = 2.40 Hz, 1H), 7.81 (d, J = 8.81 Hz, 1H), 8.69 (s, 1H), 11.14 (s, 1H) |
| 20 | (chromeno-pyrimidine-2,4-dione with 6-Cl, 7-OnPr) | 307 | 0.96 (t, J = 7.32 Hz, 3H), 1.71-1.80 (m, 2H), 4.19 (t, J = 6.38 Hz, 2H), 7.50 (s, 1H), 8.16 (s, 1H), 8.76 (s, 1H), 11.33 (s, 1H) |
| 21 | (chromeno-pyrimidine-2,4-dione with 7-OC6H13) | 314 | 0.87-0.91 (m, 3H), 1.31-1.35 (m, 4H), 1.40-1.45 (m, 2H), 1.74-1.79 (m, 2H), 4.20 (t, J = 6.50 Hz, 2H), 7.16 (dd, J = 8.88, 2.40 Hz, 1H), 7.33 (d, J = 2.40 Hz, 1H), 8.00 (d, J = 8.88 Hz, 1H), 8.89 (s, 1H), 11.33 (s, 1H) |

-continued

| Cmpd. | Structure | MW | 1H NMR, 400 MHz, DMSO-d6 |
|---|---|---|---|
| 22 | 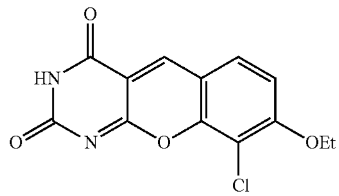 [SMILES: CCOc1ccc2cc3c(=O)[nH]c(=O)nc-3oc2c1Cl] | 293 | 1.43 (t, J = 6.96 Hz, 3H), 4.37 (q, J = 6.96 Hz, 2H), 7.44 (d, J = 8.96 Hz, 1H), 8.05 (d, J = 8.96 Hz, 1H), 8.89 (s, 1H), 11.44 (s, 1H) |
| 23 | 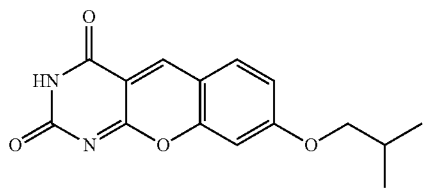 [SMILES: CC(C)COc1ccc2cc3c(=O)[nH]c(=O)nc-3oc2c1] | 286 | 1.12 (s, 3H), 1.14 (s, 3H), 2.15-2.25 (m, 1H), 4.11 (d, J = 6.56 Hz, 2H), 7.29 (dd, J = 8.76, 2.32, Hz, 1H), 7.45 (d, J = 2.24 Hz, 1H), 8.12 (d, J = 8.84 Hz, 1H), 9.01 (s, 1H), 11.45 (s, 1H) |
| 24 | 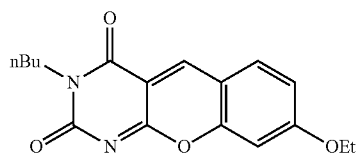 | 314 | 0.92 (t, J = 7.24 Hz, 3H), 1.26-1.33 (m, 2H), 1.40 (t, J = 6.96 Hz, 3H), 1.50-1.57 (m, 2H), 3.84 (t, J = 7.32 Hz, 2H), 4.25 (q, J = 7.00 Hz, 2H), 7.17 (dd, J = 8.76, 2.32, Hz, 1H), 7.34 (d, J = 2.32 Hz, 1H), 8.04 (d, J = 8.84 Hz, 1H), 8.95 (s, 1H) |
| 25 | 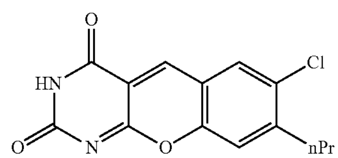 | 291 | 1.05 (t, J = 7.25 Hz, 3H), 1.64-1.70 (m, 2H), 2.81-2.85 (m, 2H), 7.76 (s, 1H), 8.20 (s, 1H), 8.85 (s, 1H), 11.50 (s, 1H) |
| 26 | 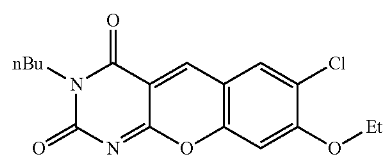 | 349 | 0.86 (t, J = 7.28 Hz, 3H), 1.19-1.28 (m, 2H), 1.36 (t, J = 6.92 Hz, 3H), 1.43-1.50 (m, 2H), 3.76 (q, J = 7.40 Hz, 2H), 4.28 (q, J = 7.00 Hz, 2H), 7.51 (s, 1H), 8.19 (s, 1H), 8.81 (s, 1H) |
| 27 | 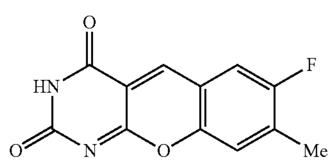 [SMILES: Cc1cc2oc3nc(=O)[nH]c(=O)c-3cc2cc1F] | 246 | 2.43 (d, J = 1.5 Hz, 3H), 7.75 (d, J = 6.17 Hz, 1H), 7.90 (d, J = 9.17 HZ, 1H), 8.87 (s, 1H), 11.47 (s, 47, 1H) |
| 28 | 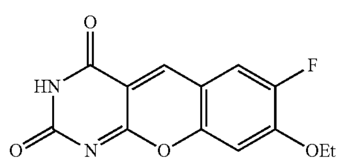 [SMILES: CCOc1cc2oc3nc(=O)[nH]c(=O)c-3cc2cc1F] | 276 | 1.42 (t, J = 6.80 Hz, 3H), 4.28 (q, J = 6.80 Hz, 2H), 7.62 (d, J = 7.05 Hz, 1H), 7.97 (d, J = 10.86 Hz, 1H), 8.83 (s, 1H), 11.38 (s, 1H) |
| 29 | 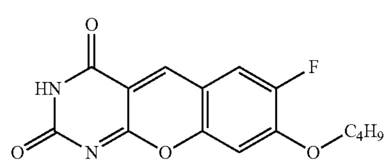 | 304 | 0.96 (t, J = 7.36 Hz, 3H), 1.43-1.49 (m, 2H), 1.76-1.83 (m, 2H), 4.28 (t, J = 6.44 Hz, 2H), 7.63 (d, J = 7.04 Hz, 1H), 7.98 (d, J = 10.85 Hz, 1H), 8.83 (s, 1H), 11.38 (s, 1H) |
| 30 | 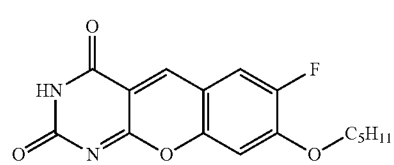 | 318 | 0.93 (t, J = 7.36 Hz, 3H), 1.34-1.44 (m, 4H), 1.77-1.84 (m, 2H), 4.28 (t, J = 6.44 Hz, 2H), 7.62 (d, J = 7.04 Hz, 1H), 7.98 (d, J = 10.85 Hz, 1H), 8.83 (s, 1H), 11.38 (s, 1H) |

-continued

| Cmpd. | Structure | MW | 1H NMR, 400 MHz, DMSO-d6 |
|---|---|---|---|
| 31 | 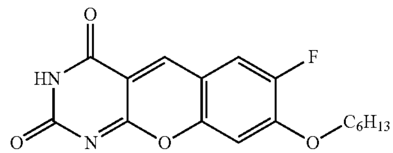 | 332 | 0.87 (t, J = 6.85 Hz, 3H), 1.30-1.35 (m, 4H), 1.39-1.48 (m, 2H), 1.76-1.82 (m, 2H), 4.28 (t, J = 6.50 Hz, 2H), 7.62 (d, J = 7.00 Hz, 1H), 7.98 (d, J = 10.85 Hz, 1H), 8.83 (s, 1H), 11.38 (s, 1H) |
| 32 | 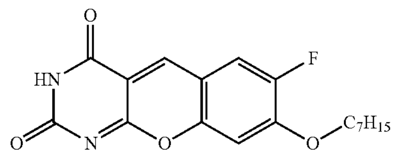 | 346 | 0.86 (t, J = 6.80 Hz, 3H), 1.28-1.30 (m, 4H), 1.32-1.37 (m, 2H), 1.42-1.46 (m, 2H), 1.76-1.83 (m, 2H), 4.27 (t, J = 6.40 Hz, 2H), 7.62 (d, J = 7.00 Hz, 1H), 7.98 (d, J = 10.80 Hz, 1H), 8.83 (s, 1H), 11.38 (s, 1H) |
| 33 | 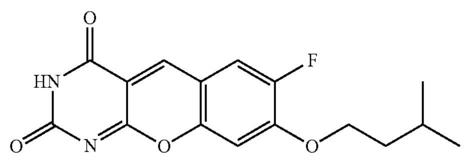 [SMILES: CC(C)CCOc1cc2oc3nc(=O)[nH]c(=O)c-3cc2cc1F] | 318 | 0.95 (s, 3H), 0.97 (s, 3H), 1.68-1.73 (m, 2H), 1.77-1.82 (m, 1H), 4.31 (t, J = 6.60 Hz, 2H), 7.66 (d, J = 7.04 Hz, 1H), 7.97 (d, J = 10.85 Hz, 1H), 8.83 (s, 1H), 11.38 (s, 1H) |
| 34 | 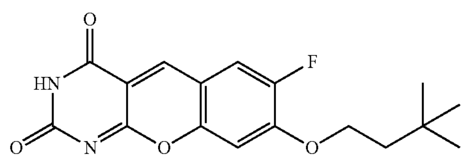 [SMILES: CC(C)(C)CCOc1cc2oc3nc(=O)[nH]c(=O)c-3cc2cc1F] | 332 | 0.99 (s, 9H), 1.75 (t, J = 7.16 2H), 4.33 (t, J = 7.16 Hz, 2H), 7.71 (d, J = 7.04 Hz, 1H), 7.98 (d, J = 10.85 Hz, 1H), 8.83 (s, 1H), 11.38 (s, 1H) |
| 35 | 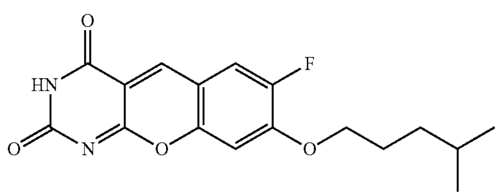 [SMILES: CC(C)CCCOc1cc2oc3nc(=O)[nH]c(=O)c-3cc2cc1F] | 332 | 0.88 (s, 3H), 0.90 (s, 3H), 1.29-1.35 (m, 2H), 1.57-1.64 (m, 1H), 1.76-1.84 (m, 2H), 4.27 (t, J = 6.60 Hz, 2H), 7.61 (d, J = 7.00 Hz, 1H), 7.97 (d, J = 10.85 Hz, 1H), 8.83 (s, 1H), 11.38 (s, 1H) |
| 36 | 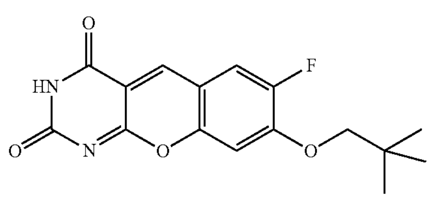 [SMILES: CC(C)(C)COc1cc2oc3nc(=O)[nH]c(=O)c-3cc2cc1F] | 318 | 1.04 (s, 9H), 3.97 (s, 2H), 7.63 (d, J = 7.40 Hz, 1H), 7.99 (d, J = 10.85 Hz, 1H), 8.84 (s, 1H), 11.38 (s, 1H) |
| 37 | 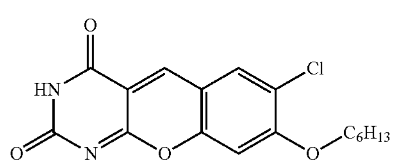 | 349 | 0.83 (t, J = 7.36 Hz, 3H), 1.22.-1.29 (m, 4H), 1.37-1.41 (m, 2H), 4.22 (t, J = 6.40 Hz, 2H), 7.50 (s, 1H), 8.15 (s, 1H), 8.75 (s, 1H), 11.32 (s, 1H) |
| 38 | 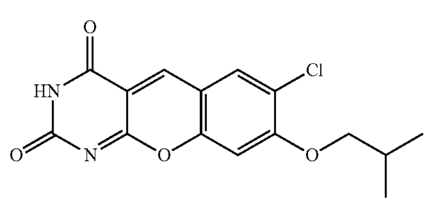 [SMILES: CC(C)COc1cc2oc3nc(=O)[nH]c(=O)c-3cc2cc1Cl] | 321 | 1.02 (s, 3H), 1.04 (s, 3H), 2.09-2.15 (m, 1H), 4.08 (d, J = 6.48 Hz, 2H), 7.56 (s, 1H), 8.23 (s, 1H), 8.83 (s, 1H), 11.40 (s, 1H) |

-continued

| Cmpd. | Structure | MW | 1H NMR, 400 MHz, DMSO-d6 |
|---|---|---|---|
| 39 | 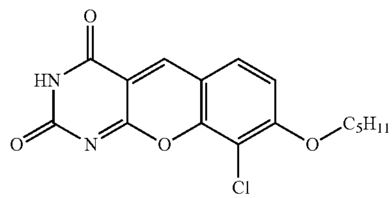 | 335 | 0.91 (t, J = 7.00 Hz, 3H), 1.36-1.47 (m, 4H), 1.77-1.85 (m, 2H), 4.30 (t, J = 6.50 Hz, 2H), 7.45 (d, J = 9.00 Hz, 1H), 8.06 (d, J = 9.00 Hz, 1H), 8.88 (s, 1H), 11.43 (s, 1H) |
| 40 | 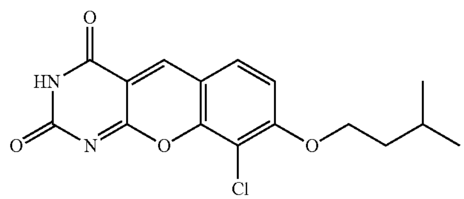 [SMILES: CC(C)CCOc1ccc2cc3c(=O)[nH]c(=O)nc-3oc2c1Cl] | 335 | 0.93 (s, 3H), 0.96 (s, 3H), 1.69-1.74 (m, 2H), 1.81-1.88 (m, 1H), 4.33 (t, J = 6.52 Hz, 2H), 7.48 (d, J = 8.96 Hz, 1H), 8.06 (d, J = 8.96 Hz, 1H), 8.89 (s, 1H), 11.43 (s, 1H) |
| 41 | 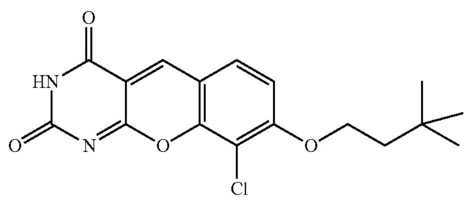 [SMILES: CC(C)(C)CCOc1ccc2cc3c(=O)[nH]c(=O)nc-3oc2c1Cl] | 349 | 1.06 (s, 9H), 1.82 (t, J = 6.90 Hz, 2H), 4.42 (t, J = 6.90 Hz, 2H), 7.59 (d, J = 9.00 Hz, 1H), 8.13 (d, J = 9.00 Hz, 1H), 8.94 (s, 1H), 11.49 (s, 1H) |
| 42 | 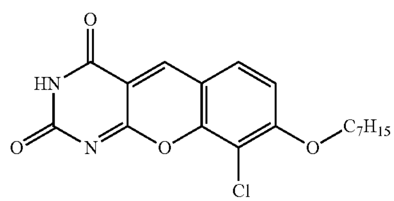 | 363 | 0.86 (t, J = 6.80 Hz, 3H), 1.27-1.30 (m, 4H), 1.32-1.37 (m, 2H), 1.42-1.46 (m, 2H), 1.78-1.83 (m, 2H), 4.30 (t, J = 6.40 Hz, 2H), 7.45 (d, J = 8.96 Hz, 1H), 8.05 (d, J = 8.96 Hz, 1H), 8.89 (s, 1H), 11.43 (s, 1H) |
| 43 | 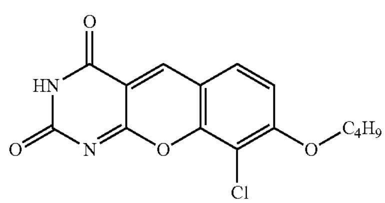 | 321 | 0.96 (t, J = 7.5 Hz, 3H), 1.47-1.52 (m, 2H), 1.76-1.83 (m, 2H), 4.32 (t, J = 6.40 Hz, 2H), 7.46 (d, J = 8.96 Hz, 1H), 8.06 (d, J = 8.96 Hz, 1H), 8.89 (s, 1H), 11.43 (s, 1H) |
| 44 | 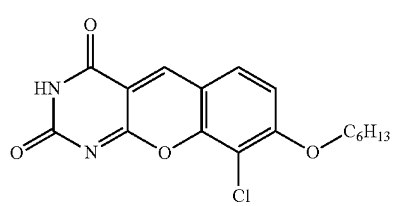 | 349 | 0.88 (t, J = 7.01 Hz, 3H), 1.29-1.36 (m, 4H), 1.45-1.49 (m, 2H), 1.77-1.83 (m, 2H), 4.30 (t, J = 6.40 Hz, 2H), 7.45 (d, J = 8.96 Hz, 1H), 8.05 (d, J = 8.96 Hz, 1H), 8.89 (s, 1H), 11.43 (s, 1H) |
| 45 | 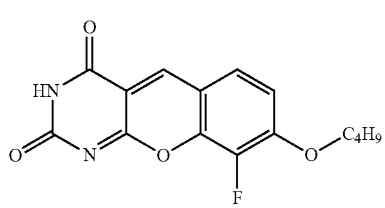 | 304 | 1.01 (t, J = 6.80 Hz, 3H), 1.47-1.57 (m, 2H), 1.83-1.88 (m, 2H), 4.35 (d, t = 6.50 Hz, 2H), 7.52 (dd, J = 7.2 Hz, 8.8 Hz, 1H), 7.96 (dd, J = 1.8 hz, 9.0 Hz), 8.96 (d, J = 1.40 Hz, 1H), 11.51 (s, 1H) |

| Cmpd. | Structure | MW | 1H NMR, 400 MHz, DMSO-d6 |
|---|---|---|---|
| 46 | (structure with OC6H13, F) | 332 | 0.87 (t, J = 6.80 Hz, 3H), 1.30-1.35 (m, 4H), 1.39-1.48 (m, 2H), 1.76-1.83 (m, 2H), 4.28 (t, J = 6.50 Hz, 2H), 7.46 (dd, J = 7.2 Hz, 8.8 Hz, 1H), 7.90 (dd, J = 1.8 hz, 9.0 Hz), 8.89 (d, J = 1.40 Hz, 1H), 11.45 (s, 1H) |
| 47 | (structure with isohexyloxy, F) | 332 | 0.88 (s, 3H), 0.90 (s, 3H), 1.30-1.36 (m, 2H), 1.56-1.63 (m, 1H), 1.76-1.84 (m, 2H), 4.28 (t, J = 6.60 Hz, 2H), 7.46 (dd, J = 7.2 Hz, 8.8 Hz, 1H), 7.90 (dd, J = 1.8 hz, 9.0 Hz), 8.89 (d, J = 1.40 Hz, 1H), 11.45 (s, 1H) |
| 48 | (structure with isobutoxy, F) | 304 | 1.01 (s, 3H), 1.03(s, 3H), 2.07-2.17 (m, 1H), 4.07(d, J = 6.60 Hz, 2H), 7.46 (dd, J = 7.2 Hz, 8.8 Hz, 1H), 7.90 (dd, J = 1.8 hz, 9.0 Hz), 8.90 (d, J = 1.54 Hz, 1H), 11.45 (s, 1H) |
| 49 | (structure with S, OEt) | 274 | 1.39 (t, J = 6.96 Hz, 3H), 4.25 (q, J = 6.97 Hz, 2H), 7.25 (dd, J = 8.84 Hz, 2.40 Hz, 1H), 7.63 (d, J = 2.40 Hz, 1H0, 8.24 (d, J = 8.84 Hz, 1H), 8.82 (s, 1H), 11. 33 (s, 1H) |
| 50 | (structure with OC4H9) | 286 | 0.91 (t, J = 7.42 Hz, 3H), 1.46-1.53 (m, 2H), 1.72-1.79 (m, 2H), 4.20 (t, J = 6.48 Hz, 2H), 7.16 (dd, J = 8.80 Hz, 2.20 Hz, 1H), 7.33 (d, J = 2.20 Hz, 1H), 7.99 (d, J = 8.84 Hz, 1H), 8.88 (s, 1H), 11.32 (s, 1H) |
| 51 | (structure with O-(CH2)4-OAc) | 344 | 1.73-1.77 (m, 2H), 1.78-1.85 (m, 2H), 2.01 (s, 3H), 4.06 (t, J = 6.40 Hz, 2H) 4.23 (t, J = 6.08 Hz, 2H), 7.17 (dd, J = 8.84 Hz, 2.20 Hz, 1H), 7.33 (d, J = 2.20 Hz, 1H), 8.00 (d, J = 8.84 Hz, 1H), 8.89 (s, 1H), 11.32 (s, 1H) |
| 52 | (structure with OC7H15, F) | 346.35 | 0.88 (t, J = 6.40 Hz, 3H), 1.26-1.38 (m, 6H), 1.40-1.47 (m, 2H), 1.77-1.84 (m, 2H), 4.29 (t, J = 6.30 Hz, 2H), 7.46 (dd, J = 7.2 Hz, 8.8 Hz, 1H), 7.89 (dd, J = 1.8 hz, 9.0 Hz), 8.90 (d, J = 1.40 Hz, 1H), 11.45 (s, 1H) |
| 53 | (structure with O-C5H10-COOH, Cl) | 378.76 | 1.46-1.51 (m, 2H), 1.56-1.63 (m, 2H), 1.79-1.91 (m, 2H), 2.22-2.27 (m, 2H), 4.31 (t, J = 6.28 Hz, 2H), 7.45 (d, J = 8.96 Hz, 1H), 8.05 (d, J = 8.96 Hz, 1H), 8.89 (s, 1H), 11.43 (s, 1H), 12.02 (bs, 1H) |

| Cmpd. | Structure | MW | 1H NMR, 400 MHz, DMSO-d6 |
|---|---|---|---|
| 54 | 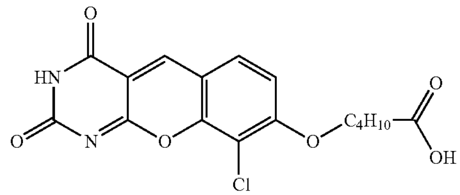 | 364.74 | 1.66-1.74 (m, 2H), 1.80-1.86 (m, 2H), 2.33(t, J = 7.40 Hz, 2H), 4.32 (t, J = 6.16 Hz, 2H), 7.45 (d, J = 8.96 Hz, 1H), 8.05 (d, J = 8.96 Hz, 1H), 8.89 (s, 1H), 11.43 (s, 1H), 12.07 (bs, 1H) |
| 55 | 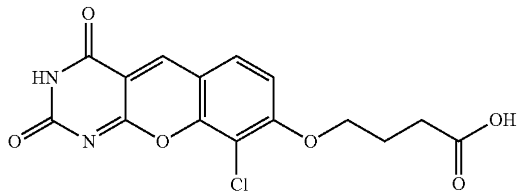 [SMILES: O=C(O)CCCOc1ccc2cc3c(=O)[nH]c(=O)nc-3oc2c1Cl] | 350.71 | 2.01-2.08 (m, 2H), 2.46(t, J = 7.26 Hz, 2H), 4.33 (t, J = 6.26 Hz, 2H), 7.45 (d, J = 8.91 Hz, 1H), 8.05 (d, J = 8.91 Hz, 1H), 8.89 (s, 1H), 11.44 (s, 1H), 12.22 (bs, 1H) |
| 56 | 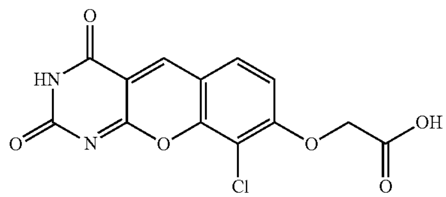 [SMILES: O=C(O)COc1ccc2cc3c(=O)[nH]c(=O)nc-3oc2c1Cl] | 322.66 | 5.10 (s, 2H), 7.36 (d, J = 9.00 Hz, 1H), 8.02 (d, J = 9.00 Hz, 1H), 8.87 (s, 1H), 11.45 (s, 1H), 12.02 (bs, 1H) |
| 57 | 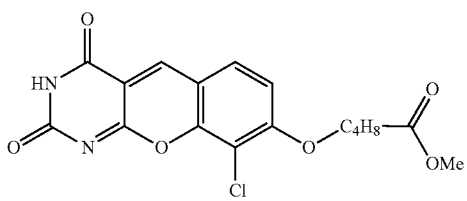 | 378.76 | 1.70-1.77 (m, 2H), 1.81-1.87 (m, 2H), 2.43 (t, J = 7.40 Hz, 2H), 3.60 (s, 3H), 4.32 (t, J = 6.10 Hz, 2H), 7.44 (d, J = 8.96 Hz, 1H), 8.05 (d, J = 8.96 Hz, 1H), 8.89 (s, 1H), 11.43 (s, 1H) |
| 58 | 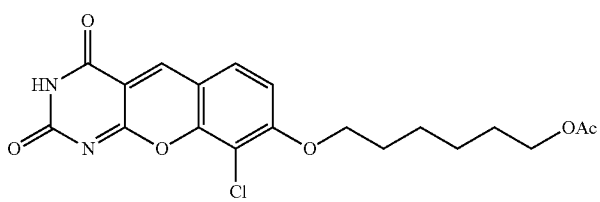 [SMILES: CC(=O)OCCCCCCOc1ccc2cc3c(=O)[nH]c(=O)nc-3oc2c1Cl] | 406.82 | 1.36-1.43 (m, 2H), 1.45-1.1.52 (m, 2H), 1.57-1.62 (m, 2H), 1.78-1.85 (m, 2H), 2.00 (s, 3H), 4.00 (t, J = 6.62 6.62 Hz, 2H), 4.31 (t, J = 6.30 Hz, 2H), 7.45 (d, J = 8.96 Hz, 1H), 8.05 (d, J = 8.96 Hz, 1H), 8.89 (s, 1H), 11.43 (s, 1H) |
| 59 | 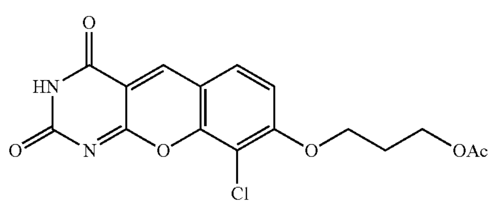 [SMILES: CC(=O)OCCCOc1ccc2cc3c(=O)[nH]c(=O)nc-3oc2c1Cl] | 364.74 | 2.02 (s, 3H), 2.11-2.18 (m, 2H), 4.21 (t, J = 6.38 Hz, 2H), 4.38 (t, J = 6.10 Hz, 2H), 7.46 (d, J = 8.96 Hz, 1H), 8.06 (d, J = 8.96 Hz, 1H), 8.89 (s, 1H), 11.44 (s, 1H) |
| 60 | 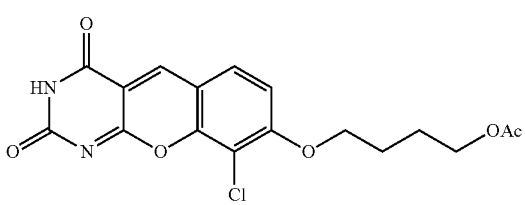 [SMILES: CC(=O)OCCCCOc1ccc2cc3c(=O)[nH]c(=O)nc-3oc2c1Cl] | 378.76 | 1.75-1.82 (m, 2H), 1.84-1.89 (m, 2H), 2.01 (s, 3H), 4.09 (t, J = 6.45 Hz, 2H), 4.31 (t, J = 6.04 Hz, 2H), 7.45 (d, J = 8.96 Hz, 1H), 8.06 (d, J = 8.96 Hz, 1H), 8.89 (s, 1H), 11.44 (s, 1H) |
| 61 | 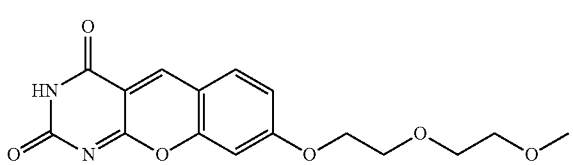 [SMILES: COCCOCCOc1ccc2cc3c(=O)[nH]c(=O)nc-3oc2c1] | 332.31 | 3.25 (s, 3H), 3.44-3.48 (m, 2H), 3.58-3.62 (m, 2H), 3.78-3.81 (m, 2H), 4.32-4.36 (m 2H), 7.18 (dd, J = 8.72, 2.52 Hz, 1H), 7.35 (d, J = 2.52 Hz, 1H), 8.00 (d, J = 8.84 Hz, 1H), 8.88 (s, 1H), 11.33 (s, 1H) |

| Cmpd. | Structure | MW | 1H NMR, 400 MHz, DMSO-d6 |
|---|---|---|---|
| 62 | 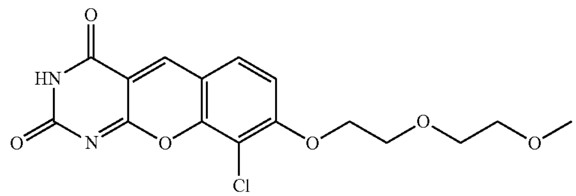 [SMILES: COCCOCCOc1ccc2cc3c(=O)[nH]c(=O)nc-3oc2c1Cl] | 366.75 | 3.25 (s, 3H), 3.47 (t, J = 4.72 Hz, 2H), 3.65 (t, J = 4.72 Hz, 2H), 3.85 (t, J = 4.33 Hz, 2H), 4.44 (t, J = 4.33 Hz, 2H), 7.46 (d, J = 8.82 Hz, 1H), 8.05 (d, J = 8.82 Hz, 1H), 8.89 (s, 1H), 11.44 (s, 1H) |
| 63 | 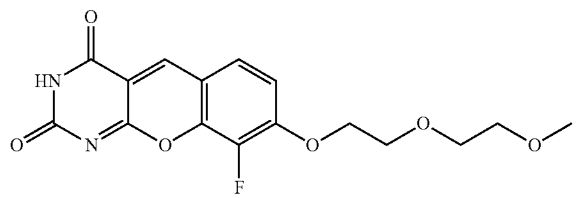 [SMILES: COCCOCCOc1ccc2cc3c(=O)[nH]c(=O)nc-3oc2c1F] | 350.3 | 3.24 (s, 3H), 3.47 (t, J = 4.72 Hz, 2H), 3.65 (t, J = 4.70 Hz, 2H), 3.86 (t, J = 4.36 Hz, 2H), 4.42 (t, J = 4.36 Hz, 2H), 7.46 (dd, J = 7.2 Hz, 8.90 Hz, 1H), 7.89 (dd, J = 1.8 hz, 9.0 Hz), 8.90 (d, J = 1.40 Hz, 1H), 11.45 (s, 1H) |
| 64 | 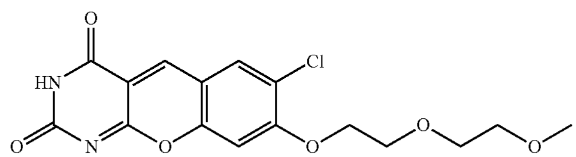 [SMILES: COCCOCCOc1cc2oc3nc(=O)[nH]c(=O)c-3cc2cc1Cl] | 366.75 | 3.25 (s, 3H), 3.49 (t, J = 4.72 Hz, 2H), 3.66 (t, J = 4.74 Hz, 2H), 3.86 (t, J = 4.40 Hz, 2H), 4.45 (t, J = 4.33 Hz, 2H), 7.53 (s, 1H), 8.17 (s, 1H), 8.88 (s, 1H), 11.43 (s, 1H) |
| 65 | 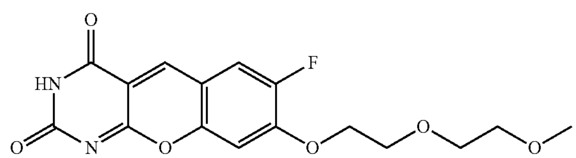 [SMILES: COCCOCCOc1cc2oc3nc(=O)[nH]c(=O)c-3cc2cc1F] | 350.3 | 3.24 (s, 3H), 3.46 (t, J = 4.72 Hz, 2H), 3.65 (t, J = 4.66 Hz, 2H), 3.86 (t, J = 4.36 Hz, 2H), 4.44 (t, J = 4.36 Hz, 2H), 7.62 (d, J = 7.00 Hz, 1H), 7.98 (d, J = 10.80 Hz, 1H), 8.90 (s, 1H), 11.40 (s, 1H) |
| 66 | 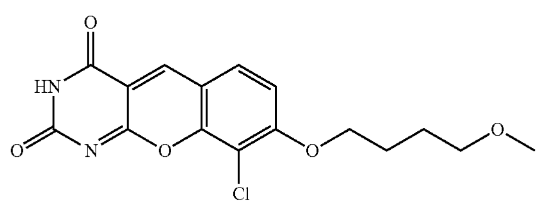 [SMILES: COCCCCOc1ccc2cc3c(=O)[nH]c(=O)nc-3oc2c1Cl] | 350.75 | 1.67-1.73 (m, 2H), 1.82-1.89 (m, 2H), 3.25 (s, 3H), 3.40 (t, J = 6.30 Hz, 2H), 4.33 (t, J = 6.30 Hz, 2H), 7.45 (d, J = 8.95 Hz, 1H), 8.08 (d, J = 8.95 Hz, 1H), 8.89 (s, 1H), 11.43 (s, 1H) |
| 67 | 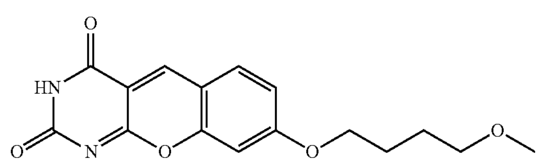 [SMILES: COCCCCOc1ccc2cc3c(=O)[nH]c(=O)nc-3oc2c1] | 316.31 | 1.65-1.70 (m, 2H), 1.77-1.83 (m, 2H), 3.25 (s, 3H), 3.38 (t, J = 6.37 Hz, 2H), 4.22 (t, J = 6.37 Hz, 2H), 7.16 (dd, J = 8.72 Hz, 2.26 Hz, 1H), 7.32 (d, J = 2.26 Hz, 1H), 8.00 (d, J = 8.72 Hz, 1H), 8.88 (s, 1H), 11.32 (s, 1H) |
| 68 | 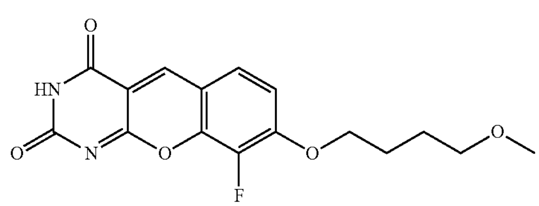 [SMILES: COCCCCOc1ccc2cc3c(=O)[nH]c(=O)nc-3oc2c1F] | 334.3 | 1.66-1.71 (m, 2H), 1.81-1.89 (m, 2H), 3.24 (s, 3H), 3.40 (t, J = 6.36 Hz, 2H), 4.34 (t, J = 6.36 Hz, 2H), 7.45 (dd, J = 7.2 Hz, 8.8 Hz, 1H), 7.89 (dd, J = 1.8 hz, 9.0 Hz), 8.89 (d, J = 1.40 Hz, 1H), 11.45 (s, 1H) |
| 69 | 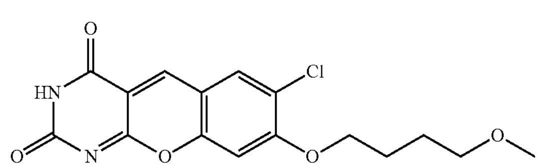 [SMILES: COCCCCOc1cc2oc3nc(=O)[nH]c(=O)c-3cc2cc1Cl] | 350.75 | 1.67-1.74 (m, 2H), 1.82-1.88 (m, 2H), 3.25 (s, 3H), 3.42 (t, J = 6.30 Hz, 2H), 4.32 (t, J = 6.30 Hz, 2H), 7.50 (s, 1H), 8.15 (s, 1H), 8.86 (s, 1H), 11.43 (s, 1H) |

| Cmpd. | Structure | MW | 1H NMR, 400 MHz, DMSO-d6 |
|---|---|---|---|
| 70 | 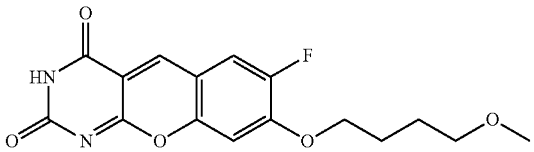 [SMILES: COCCCCOc1cc2oc3nc(=O)[nH]c(=O)c-3cc2cc1F] | 334.3 | 1.67-1.75 (m, 2H), 1.82-1.88 (m, 2H), 3.24 (s, 3H), 3.43 (t, J = 6.33 Hz, 2H), 4.32 (t, J = 6.30 Hz, 2H), 7.65 (d, J = 7.04 Hz, 1H), 7.98 (d, J = 10.86 Hz, 1H), 8.84 (s, 1H), 11.40 (s, 1H) |
| 71 | 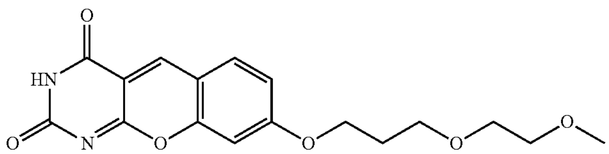 [SMILES: COCCOCCCOc1ccc2cc3c(=O)[nH]c(=O)nc-3oc2c1] | 346.33 | 2.02-2.08 (m, 2H), 3.23 (s, 3H), 3.43-3.45 (m, 2H), 3.50-3.56 (m, 2H), 3.60 (t, J = 6.20 Hz, 2H), 4.36 (t, J = 6.20 Hz, 2H), 7.17 (dd, J = 8.72, 2.24 Hz, 1H), 7.33 (d, J = 2.24 Hz, 1H), 8.00 (d, J = 8.72 Hz, 1H), 8.89 (s, 1H), 11.34 (s, 1H) |
| 72 | 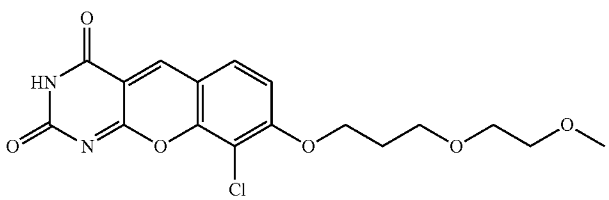 [SMILES: COCCOCCCOc1ccc2cc3c(=O)[nH]c(=O)nc-3oc2c1Cl] | 380.78 | 2.02-2.09 (m, 2H), 3.22 (s, 3H), 3.43-3.45 (m, 2H), 3.50-3.54 (m, 2H), 3.60 (t, J = 6.12 Hz, 2H), 4.36 (t, J = 6.12 Hz, 2H), 7.46 (d, J = 8.92 Hz, 1H), 8.05 (d, J = 8.82 Hz, 1H), 8.89 (s, 1H), 11.44 (s, 1H) |
| 73 | 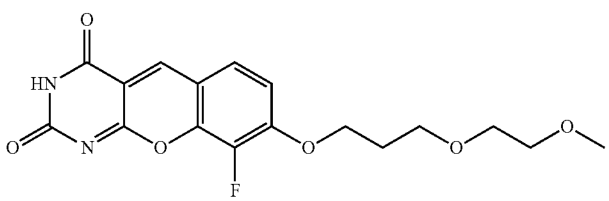 [SMILES: COCCOCCCOc1ccc2cc3c(=O)[nH]c(=O)nc-3oc2c1F] | 364.33 | 2.03-2.10 (m, 2H), 3.24 (s, 3H), 3.41-3.45 (m, 2H), 3.50-3.54 (m, 2H), 3.60 (t, J = 6.18 Hz, 2H), 4.38 (t, J = 6.18 Hz, 2H),7.45 (dd, J = 7.2 Hz, 8.8 Hz, 1H), 7.88 (dd, J = 1.8 hz, 9.0 Hz), 8.89 (d, J = 1.40 Hz, 1H), 11.42 (s, 1H) |
| 74 | 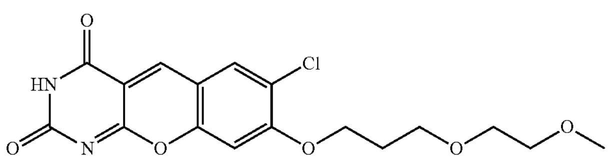 [SMILES: COCCOCCCOc1cc2oc3nc(=O)[nH]c(=O)c-3cc2cc1Cl] | 380.78 | 2.03-2.09 (m, 2H), 3.23 (s, 3H), 3.43-3.48 (m, 2H), 3.50-3.56 (m, 2H), 3.60 (t, J = 6.18 Hz, 2H), 4.34 (t, J = 6.18 Hz, 2H), 7.52 (s, 1H), 8.18(s, 1H), 8.86 (s, 1H), 11.35 (s, 1H) |
| 75 | 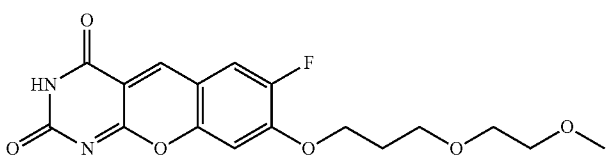 [SMILES: COCCOCCCOc1cc2oc3nc(=O)[nH]c(=O)c-3cc2cc1F] | 364.33 | 2.00-2.08 (m, 2H), 3.24 (s, 3H), 3.43-3.46 (m, 2H), 3.51-3.54 (m, 2H), 3.57 (t, J = 6.25 Hz, 2H), 4.34 (t, J = 6.12 Hz, 2H), 7.64 (d, J = 7.00 Hz, 1H), 7.98 (d, J = 10.71 Hz, 1H), 8.84 (s, 1H), 11.39 (s, 1H) |

Example 3

Materials and Methods

Fluorescence Polarization (FP) Assay

To identify direct NF-κB inhibitors, a fluorescence polarization (FP) screening assay was developed using c-Rel homodimer and CD28 response element (CD28RE) in the promoter region of the IL-2 gene. 5'-fluorescein-labeled duplex CD28RE oligonucleotide probe (10 nM) was mixed with Rel protein (128 nM) in reaction buffer (20 mM Tris (pH7.5), 100 mM NaCl, 0.5 ug/ml polydldC, 1% NP-40, 0.1% BSA). 20 µl of the mixture was added to each well of a 384-well plate, compound of interest was added (25 µM), and plates were incubated for 30 minutes at room temperature. The anisotropy value of each reaction well was measured using Fusion™ Universal Microplate Analyzer (Perkin Elmer, PE). A series of titration experiments were performed to optimize c-Rel protein and FITC-CD28RE probe concentrations to be used in the FP assay. The representative data for 10 nM and 0.33 nM are shown in FIG. 1A and FIG. 1D, respectively. FIG. 1B shows results from cold competition with specific and non-specific oligos. FIG. 1C shows the distribution of FP signals in a representative 384-well plate.

For the 10 nM and 0.33 nM FP assays shown in FIG. 1A and FIG. 1D, respectively, the maximal Signal to Background (S/B) ratio was in the range of 8-11, indicating a robust assay. The background value for DNA probe alone was ~20 mP and the signal for c-Rel-CD28RE reaction was 200 mP.

Electrophoretic Mobility Shift Assay (EMSA)

DNA binding reaction (20 µL) was carried out in 1×DNA Binding Buffer (10 mM Tris, 40 mM NaCl, 1 mM EDTA, 4% glycerol) with 10 nM c-Rel protein and 0.5 ng phosphor-labeled CD28RE oligonucleotide for 10 minutes at room temperature in 96-well plates. Test compounds, in serial dilutions, were added into each well, and further incubated for 15 minutes before loading onto native 5% polyacrylamide gel. Electrophoresis proceeded for 2.5 hours at 160V.

Figure 2:
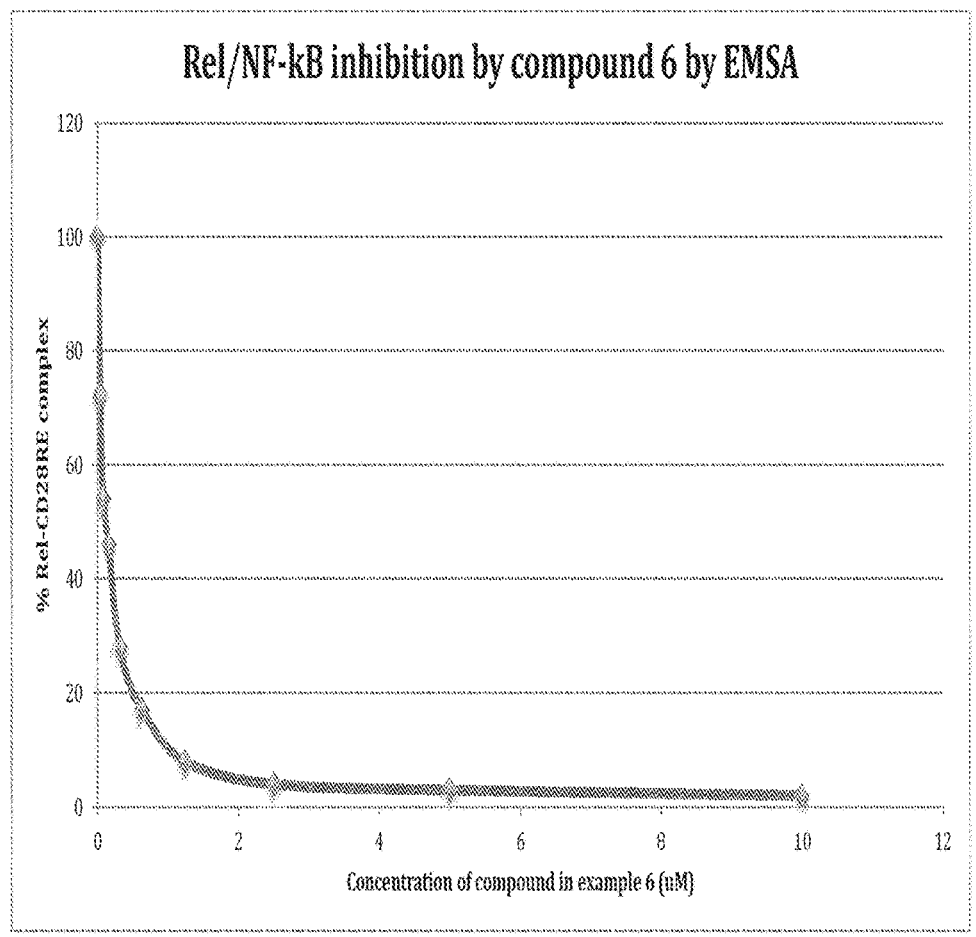
FIG. 2 is a line graph showing Rel/NF-κB inhibition by compound 6 by EMSA.
Figure 3B:
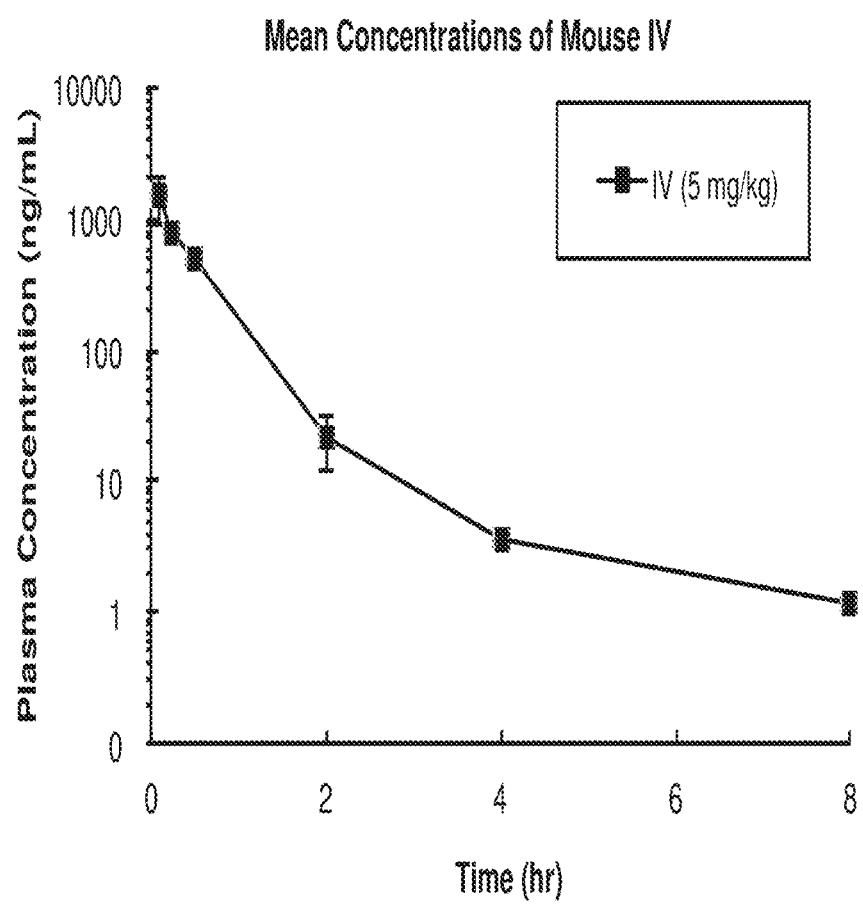
FIG. 3B is a line graph showing mean plasma concentration of intravenous compound 13 in mice over time.
Figure 4B:
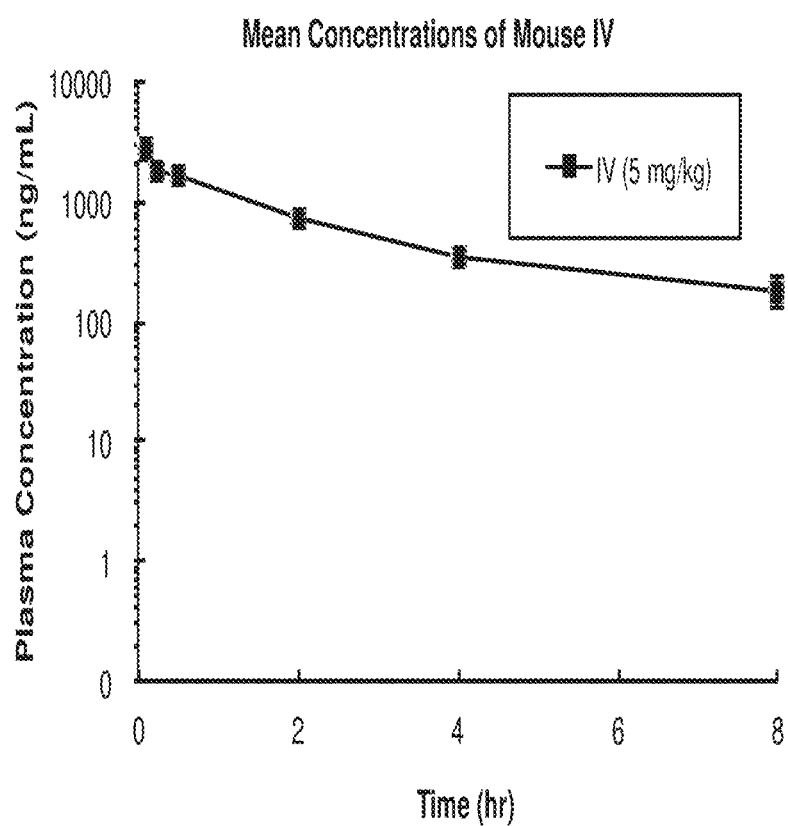
FIG. 4B is a line graph showing mean plasma concentration of intravenous compound 20 in mice over time.
Figure 5B:
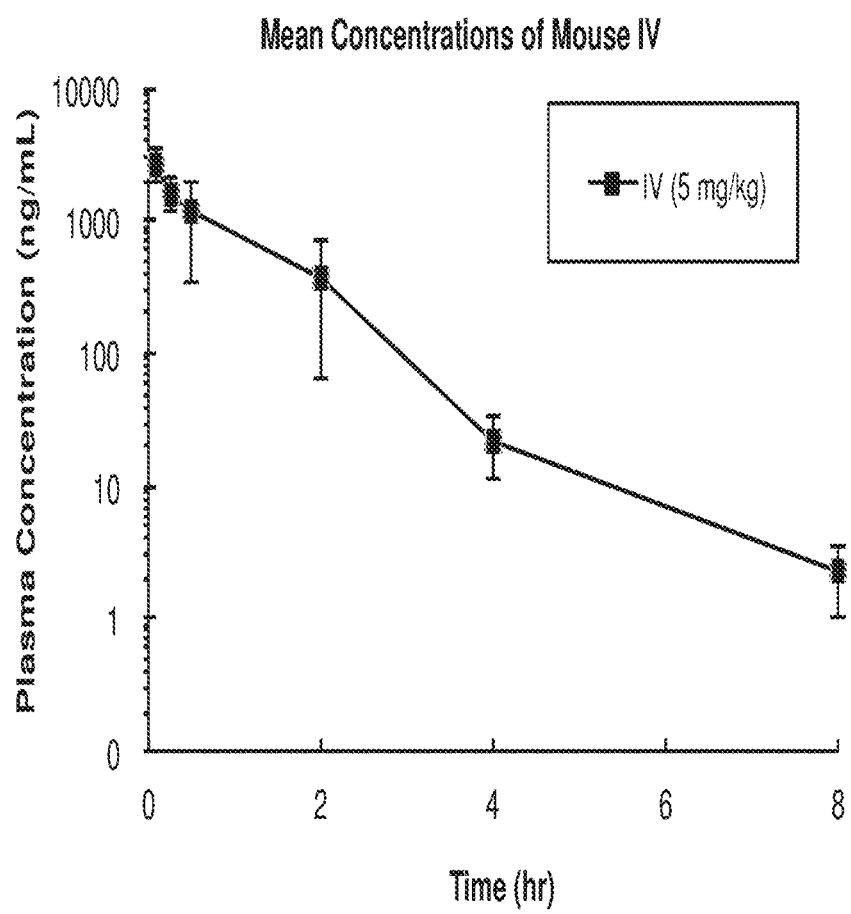
FIG. 5B is a line graph showing mean plasma concentration of intravenous compound 26 in mice over time.
Figure 6B:
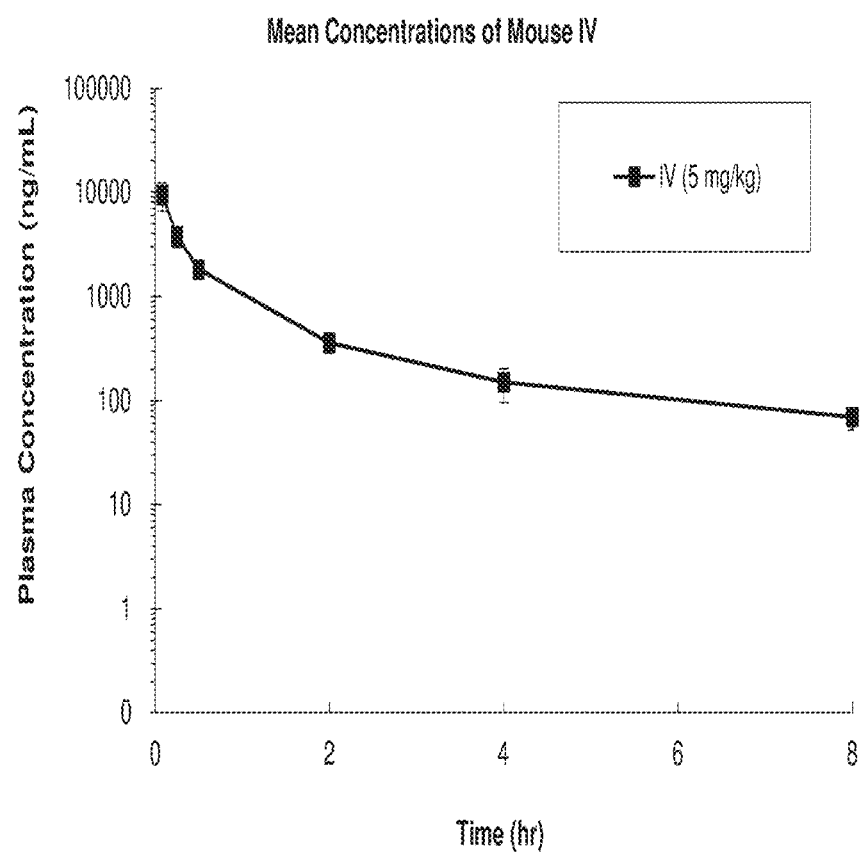
FIG. 6B is a line graph showing mean plasma concentration of intravenous compound 42 in mice over time.
Figure 7B:
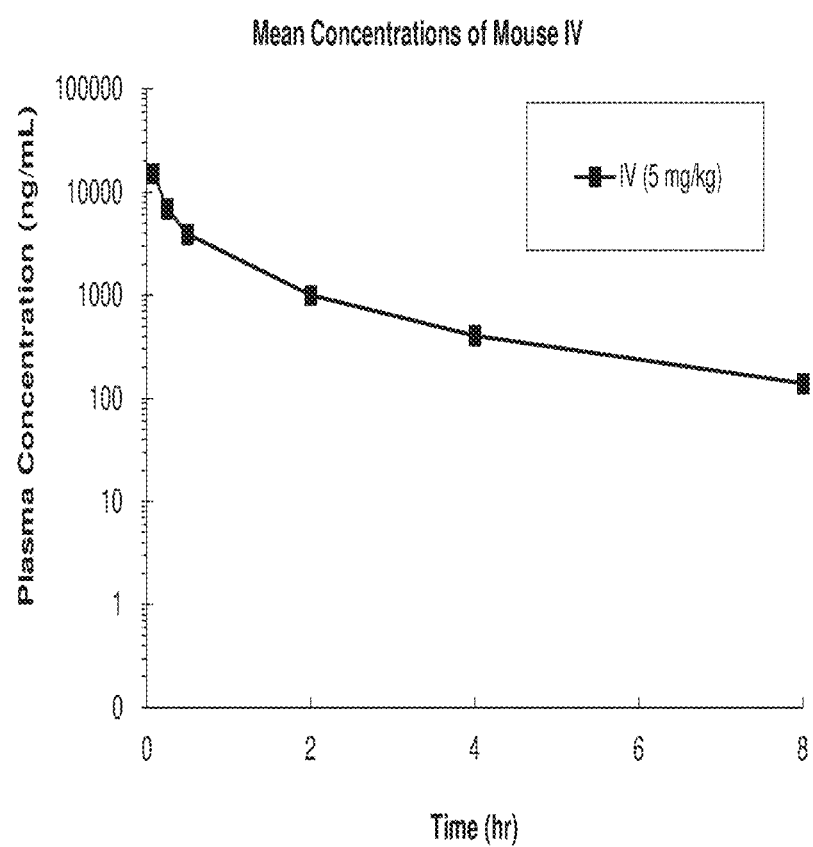
FIG. 7B is a line graph showing mean plasma concentration of intravenous compound 44 in mice over time.
Figure 8B:
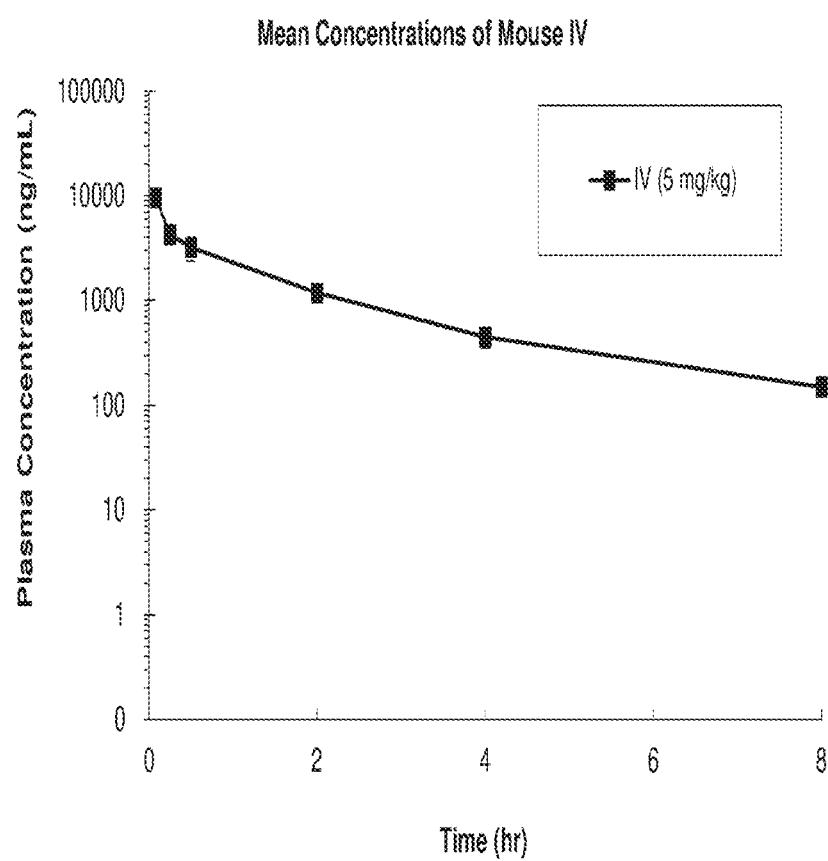
FIG. 8B is a line graph showing mean plasma concentration of intravenous compound 46 in mice over time.

Radioactive signals were quantified using Phospho-Imager. $IC_{50}$ of compounds of example 1 to 75 were determined by quantifying the intensity of Rel/NF-κB inhibition in EMSA using phospho-imager. An example of EMSA data of the present invention is shown for compound 6 in FIG. 2.

NF-κB GFP Assay

NFκB/Jurkat/GFP transcriptional reporter cell line was obtained from SBI System Biosciences. NF-κB/Jurkat/GFP™ Reporter cells ($5 \times 10^5$ cells) were plated at a concentration of 1 million cells/ml into each well of a 24-well plate. TNF-α (5 ng/ml) was added. Compounds were added via serial dilutions to corresponding wells. After 24 hours, 100 μl of the cells were transferred to a well of a Costar® UV plate (96 well, No lid, w/ UV Transparent Flat Bottom, Corning, N.Y., Cat#3635) and the intensity of GFP fluorescence was measured (Excitation 485+/−20, Emission 528+/−20) in a Synergy™ HT Multi-Detection Microplate Reader (BioTech, Winooski, Vt.). The intensities of GFP measured were plotted against the amount of TNF-α.

Pharmacokinetic Study of Compounds in CD-1 Mice

The study duration was two weeks, including acclimation and in-life portions. Three male mice were studied per compound. 5 mg/kg of the compound of interest was administered intravenously via the tail vein in a single dose. Body weight was determined before the first dose. The dosage vehicle was comprised of 100% PEG 400 and 2 meq NaOH. Blood samples were collected at 0.0833, 0.25, 0.5, 2, 4, and 8 hours post-dose. Plasma was generated from blood with $K_2EDTA$ as the anticoagulant.

Example 4

EMSA and NF-κB GFP Assay Results

| Compound | EMSA IC50 (μM) | NF-KB GFP IC50 (μM) |
| --- | --- | --- |
| 1 | <2 | <30 |
| 2 | <2 | <30 |
| 3 | <2 | <30 |
| 4 | <2 | <30 |
| 5 | <2 | <30 |
| 6 | <1 | <10 |
| 7 | <2 | <30 |
| 8 | <0.5 | <30 |
| 9 | <5 | <20 |
| 10 | <1 | <30 |
| 11 | <1 | <20 |
| 12 | <1 | 7 |
| 13 | <1 | 9 |
| 14 | <1 | 8.2 |
| 15 | <0.5 | <30 |
| 16 | <0.5 | <30 |
| 17 | <0.5 | <30 |
| 18 | <0.5 | 10 |
| 19 | <1 | <5 |
| 20 | <1 | <5 |
| 21 | <1 | <5 |
| 22 | <1 | <10 |
| 23 | <1 | <5 |
| 24 | <1 | <30 |
| 25 | <1 | <30 |
| 26 | <1 | <30 |
| 27 | <0.5 | <5 |
| 28 | <0.5 | <5 |
| 29 | <0.5 | <5 |
| 30 | <0.5 | <10 |
| 31 | <0.5 | <5 |
| 32 | <0.5 | <5 |
| 33 | <0.5 | <3 |
| 34 | <0.5 | 10 |
| 35 | <1 | <10 |
| 36 | <0.5 | <10 |
| 37 | <0.5 | <20 |
| 38 | <0.5 | <20 |
| 39 | <0.5 | <3 |
| 40 | <0.5 | 5 |
| 41 | <0.5 | <10 |
| 42 | <0.5 | <10 |
| 43 | <0.5 | <3 |
| 44 | <0.5 | <3 |
| 45 | <0.5 | <5 |
| 46 | <0.5 | <5 |
| 47 | <1 | <5 |
| 48 | <0.5 | <5 |
| 49 | <1 | <5 |
| 50 | <1 | <5 |
| 51 | <1 | <5 |
| 52 | <0.5 | <5 |
| 53 | <5 | <20 |
| 54 | <5 | <20 |
| 55 | <5 | <20 |
| 56 | <5 | <20 |
| 57 | <5 | <20 |
| 58 | <5 | <20 |
| 59 | <5 | <20 |
| 60 | <5 | <20 |
| 61 | <1 | <5 |
| 62 | <1 | <5 |
| 63 | <1 | <5 |
| 64 | <1 | <5 |
| 65 | <1 | <5 |
| 66 | <1 | <5 |
| 67 | <1 | <5 |
| 68 | <1 | <5 |
| 69 | <1 | <5 |
| 70 | <1 | <5 |
| 71 | <1 | <5 |
| 72 | <1 | <5 |
| 73 | <1 | <5 |
| 74 | <1 | <5 |
| 75 | <1 | <5 |

Example 5

Pharmacokinetic Analysis

Pharmacokinetic parameters for compounds 13, 20, 26, 42, 44, and 46 are shown in FIGS. 3-8, respectively.

DOCUMENTS

1. Aly, H. M. and Kamal, M. M. (2012). Efficient one-pot preparation of novel fused chromeno[2,3-d]pyrimidine and pryano[2,3-d]pyrimidine derivatives. *European Journal of Medicinal Chemistry* 47: 18-23.
2. Blythin, D. J., Domalski, M. S., Kim, Y. C., Kuo, J., and Liu, J.-H. (1981). Simple synthetic route to "Oxa-Deaza-Flavins" (2H-[1]-Benzopyrano [2,3-d] Pyrimidine-2,4 (3H)-Diones). *Heterocycles* 16(2): 203-207.
3. U.S. Pat. No. 4,272,535.
4. International Application No. PCT/US2007/074233.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A compound having the structure of formula (I):

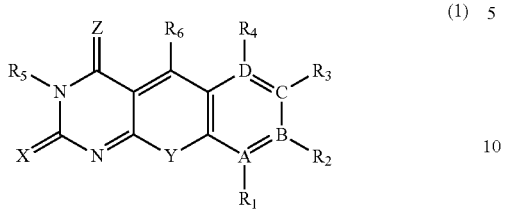

(1)

wherein:
A, B, C, and D are independently selected from the group consisting of carbon and nitrogen;
X, Y, and Z are independently selected from the group consisting of oxygen, sulfur, and $NR^a$;
$R_1$ is selected from the group consisting of no atom, hydrogen, halogen, $C_{1-9}$ alkyl, $C_{2-9}$ alkenyl, $C_{2-9}$ alkynyl, aryl, $C_{1-9}$ heterocyclic, —OH, —$OR^d$, —$OR^bOR^a$, —$OR^cOR^bOR^a$, —$OR^b(C=O)R^a$, —$O(C=O)R^d$, —$O(C=O)OR^a$, —$O(C=O)NR^bR^a$, cyano, nitro, —$CF_3$, —$CHF_2$, —$CH_2F$, —CHO, —COOH, —$COR^a$, —$COOR^a$, —$CONR^bR^a$, —$CONHCONR^bR^a$, —$NR^bR^a$, —$NHCOR^a$, —$NR^bCOR^a$, —CSOH, —$CSR^a$, —$CSOR^a$, —$CSNR^bR^a$, —$CSNHCSNR^bR^a$, —SH, —$SR^a$, —$S(C=O)R^a$, —$S(C=O)OR^a$, —$S(C=O)NR^bR^a$;
$R_2$ is selected from the group consisting of no atom, hydrogen, halogen, $C_{1-9}$ alkyl, $C_{2-9}$ alkenyl, $C_{2-9}$ alkynyl, aryl, $C_{1-9}$ heterocyclic, —OH, —$OR^d$, —$OR^bOR^a$, —$OR^cOR^bOR^a$, —$OR^b(C=O)R^a$, —$O(C=O)R^d$, —$O(C=O)OR^a$, —$O(C=O)NR^bR^a$, cyano, nitro, —$CF_3$, —$CHF_2$, —$CH_2F$, —CHO, —COOH, —$COR^a$, —$COOR^a$, —$CONR^bR^a$, —$CONHCONR^bR^a$, —$NR^bR^a$, —$NHCOR^a$, —$NR^bCOR^a$, —CSOH, —$CSR^a$, —$CSOR^a$, —$CSNR^bR^a$, —$CSNHCSNR^bR^a$, —SH, —$SR^a$, —$S(C=O)R^a$, —$S(C=O)OR^a$, —$S(C=O)NR^bR^a$;
$R_3$ and $R_4$ are independently selected from the group consisting of no atom, hydrogen, halogen, $C_{1-9}$ alkyl, $C_{2-9}$ alkenyl, $C_{2-9}$ alkynyl, aryl, $C_{1-9}$ heterocyclic, —OH, —$OR^d$, —$OR^bOR^a$, —$OR^cOR^bOR^a$, —$OR^b(C=O)R^a$, —$O(C=O)R^d$, —$O(C=O)OR^a$, —$O(C=O)NR^bR^a$, cyano, nitro, —$CF_3$, —$CHF_2$, —$CH_2F$, —CHO, —COOH, —$COR^a$, —$COOR^a$, —$CONR^bR^a$, —$CONHCONR^bR^a$, —$NR^bR^a$, —$NHCOR^a$, —$NR^bCOR^a$, —CSOH, —$CSR^a$, —$CSOR^a$, —$CSNR^bR^a$, —$CSNHCSNR^bR^a$, —SH, —$SR^a$, —$S(C=O)R^a$, —$S(C=O)OR^a$, —$S(C=O)NR^bR^a$;
$R_5$ is selected from the group consisting of hydrogen, $C_{5-9}$ alkyl, $C_{2-9}$ alkenyl, $C_{2-9}$ alkynyl, aryl, $C_{1-9}$ heterocyclic, —$R^aCO$, —$R^aNHCO$, and $R^aOCO$;
$R_6$ is selected from the group consisting of hydrogen, hydroxyl, amine, $C_{1-9}$ alkyl, $C_{2-9}$ alkenyl, $C_{2-9}$ alkynyl, aryl, and $C_{1-9}$ heterocyclic;
$R^a$ is selected from the group consisting of hydrogen, amine, $C_{1-9}$ alkyl, $C_{2-9}$ alkenyl, $C_{2-9}$ alkynyl, aryl, and $C_{1-9}$ heterocyclic;
$R^b$ and $R^c$ are independently selected from the group consisting of oxygen, amine, $C_{1-9}$ alkylene, $C_{2-9}$ alkenylene, $C_{2-9}$ alkynylene, arylene, and $C_{1-9}$ heterocyclic; and $R^d$ is selected from the group consisting of hydrogen, amine, $C_{2-9}$ alkyl, $C_{2-9}$ alkenyl, $C_{2-9}$ alkynyl, aryl, and $C_{1-9}$ heterocyclic;
wherein:
if X is sulfur,
$R_2$ is selected from the group consisting of no atom, hydrogen, halogen, $C_{1-9}$ alkyl, $C_{2-9}$ alkenyl, $C_{2-9}$ alkynyl, aryl, $C_{1-9}$ heterocyclic, —$OR^d$, —$OR^bOR^a$, —$OR^cOR^bOR^a$, —$OR^b(C=O)R^a$, —$O(C=O)R^d$, —$O(C=O)OR^a$, —$O(C=O)NR^bR^a$, cyano, nitro, —$CF_3$, —$CHF_2$, —$CH_2F$, —CHO, —COOH, —$COR^a$, —$COOR^a$, —$CONR^bR^a$, —$CONHCONR^bR^a$, —$NR^bR^a$, —$NHCOR^a$, —$NR^bCOR^a$, —CSOH, —$CSR^a$, —$CSOR^a$, —$CSNR^bR^a$, —$CSNHCSNR^bR^a$, —SH, —$S(C=O)R^a$, —$S(C=O)OR^a$, —$S(C=O)NR^bR^a$; and,
$R^d$ is selected from the group consisting of amine, $C_{2-9}$ alkyl, $C_{2-9}$ alkenyl, $C_{2-9}$ alkynyl, aryl, and $C_{1-9}$ heterocyclic;
or a hydrate or pharmaceutically acceptable salt thereof.

2. A compound according to claim 1,
wherein:
X, Y, and Z are independently selected from the group consisting of oxygen and sulfur;
$R_1$ is selected from the group consisting of —H, —F, —Cl, —Br, and —OEt;
$R_2$ is selected from the group consisting of —H, —$CH_3$, —OH, —OEt, -Me, -Et, -nPr, —O-nPr, -OEtnPr, —$OC_4H_9$, —$OC_5H_{11}$, —$OC_6H_{13}$, —$OC_7H_{15}$, —O-isobutyl, —O-isopentyl, —$OC_nH_{2n}OMe$, —$OC_nH_{2n}OC_mH_{2m}OMe$, —$OC_nH_{2n}OH$, —$OC_nH_{2n}OC_mH_{2m}OH$, —$OC_nH_{2n}OEt$, —$OC_nH_{2n}OC_mH_{2m}OEt$, —O—$C_nH_{2n}COOH$, —O—$C_nH_{2n}CONH2$, —O—$C_nH_{2n}CONHMe$,

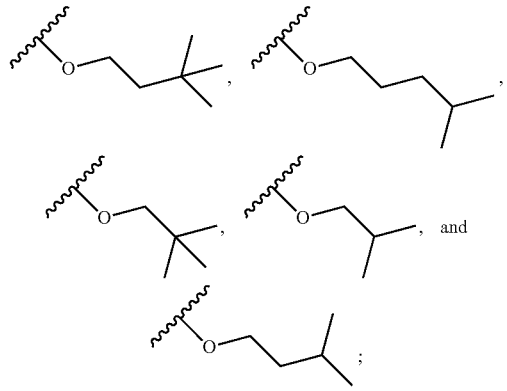

, and

;

$R_3$ is selected from the group consisting of —H, —Cl, —Br, and —F;
$R_4$ is —H;
$R_5$ is selected from the group consisting of —H and -Ph; and
$R_6$ is selected from the group consisting of —H and —$CH_3$,
m is 2, 3, 4 or 5;
n is 2, 3, 4, or 5;
wherein:
if X is sulfur,
$R_2$ is selected from the group consisting of —H, —$CH_3$, —OEt, -Me, -Et, -nPr, —O-nPr, —OEtnPr, —OC$_4$H$_9$, —OC$_5$H$_{11}$, —OC$_6$H$_{13}$, —OC$_7$H$_{15}$, —O-isobutyl, —O-isopentyl, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, —OC$_n$H$_{2n}$OEt, —OC$_n$H$_{2n}$OC$_m$H$_{2m}$OEt, —O—C$_n$H$_{2n}$COOH, —O—C$_n$H$_{2n}$CONH2, —O—C$_n$H$_{2n}$CONHMe,

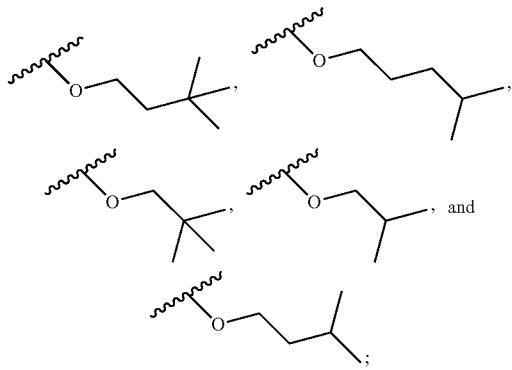

or a hydrate or pharmaceutically acceptable salt thereof.

3. A compound according to claim 1, wherein:

X, Y, and Z are independently selected from the group consisting of oxygen and sulfur; and R$_6$ is hydrogen, wherein:

if X is sulfur,

R$_2$ is selected from the group consisting of no atom, hydrogen, halogen, C$_{1-9}$ alkyl, C$_{2-9}$ alkenyl, C$_{2-9}$ alkynyl, aryl, C$_{1-9}$ heterocyclic, —OR$^d$, —OR$^b$OR$^a$, —OR$^c$OR$^b$OR$^a$, —OR$^b$(C=O)R$^a$, —O(C=O)R$^d$, —O(C=O)OR$^a$, —O(C=O)NR$^b$R$^a$, cyano, nitro, —CF$_3$, —CHF$_2$, —CH$_2$F, —CHO, —COOH, —COR$^a$, —COOR$^a$, —CONR$^b$R$^a$, —CONHCONR$^b$R$^a$, —NR$^b$R$^a$, —NHCOR$^a$, —NR$^b$COR$^a$, —CSOH, —CSR$^a$, —CSOR$^a$, —CSNR$^b$R$^a$, —CSNHCSNR$^b$R$^a$, —SH, —S(C=O)R$^a$, —S(C=O)OR$^a$, S(C=O)NR$^b$R$^a$; and, R$^d$ is selected from the group consisting of amine, C$_{2-9}$ alkyl, C$_{2-9}$ alkenyl, C$_{2-9}$ alkynyl, aryl, and C$_{1-9}$ heterocyclic;

or a hydrate or pharmaceutically acceptable salt thereof.

4. A compound according to claim 3, wherein:

Z is oxygen;

R$_1$ and R$_3$ are selected from the group consisting of hydrogen, halogen, —CN, and —CF$_3$;

R$_2$ is selected from the group consisting of C$_{2-9}$ alkoxy, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, —OC$_n$H$_{2n}$OEt, —OC$_n$H$_{2n}$OC$_m$H$_{2m}$OEt, —O—C$_n$H$_{2n}$COOH, —O—C$_n$H$_{2n}$CONH$_2$, —O—C$_n$H$_{2n}$CONHMe, and —OH;

m is 2, 3, 4 or 5;

n is 2, 3, 4, or 5; and

R$_4$ is selected from the group consisting of hydrogen, C$_{2-9}$ alkoxy and —OH, or a hydrate or pharmaceutically acceptable salt thereof.

5. A compound according to claim 4, wherein:

X and Y are oxygen; and

R$_4$ is hydrogen, or a hydrate or pharmaceutically acceptable salt thereof.

6. A compound according to claim 5, wherein the compound is selected from the group consisting of:

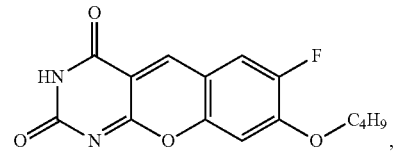

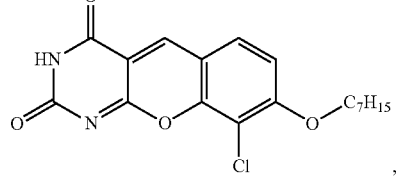

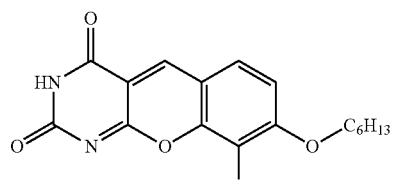

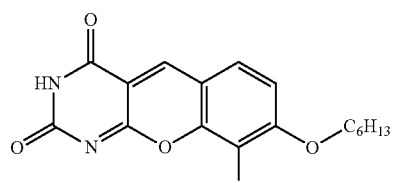

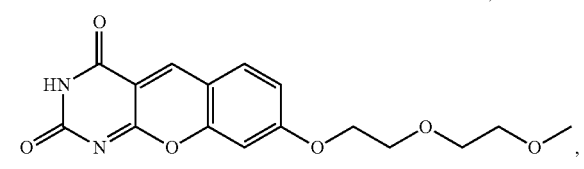

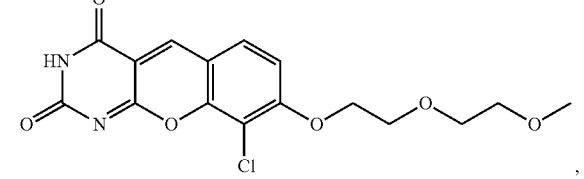

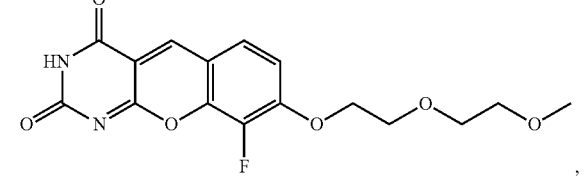

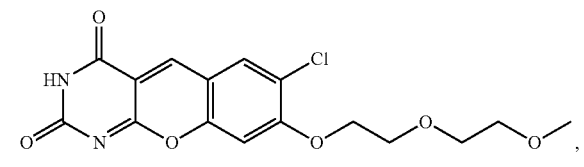

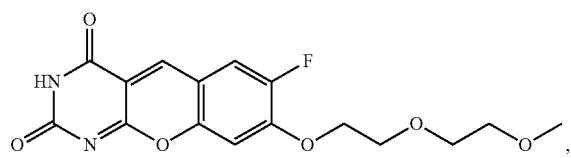,
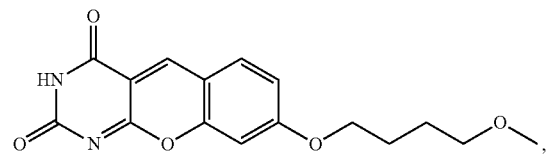,
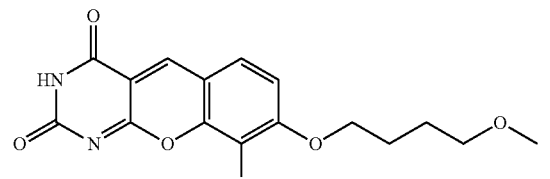,
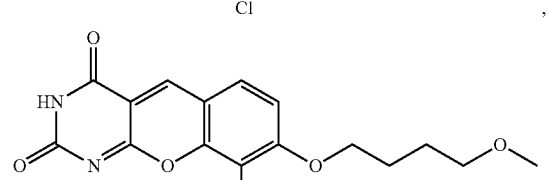,
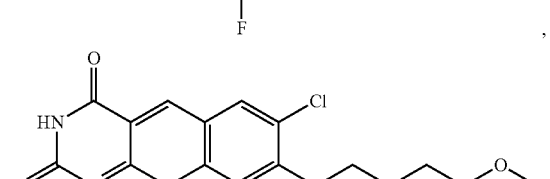,
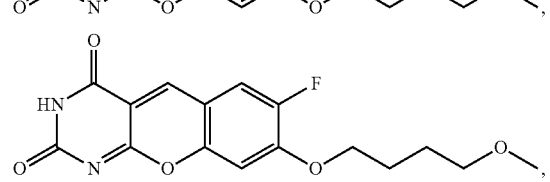,
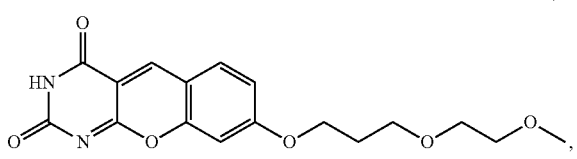,
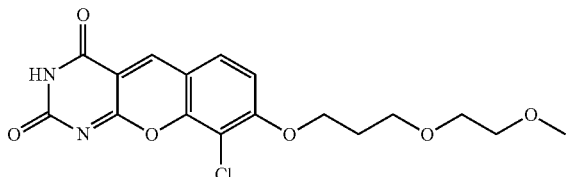,
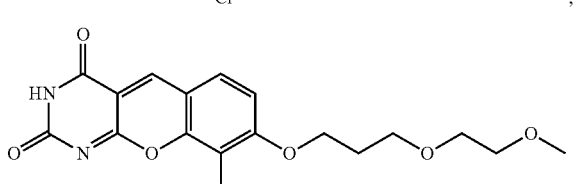,
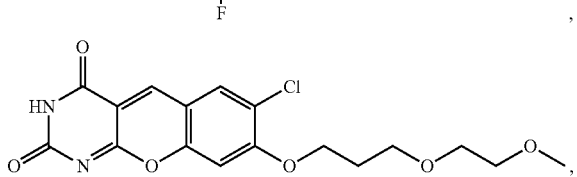,
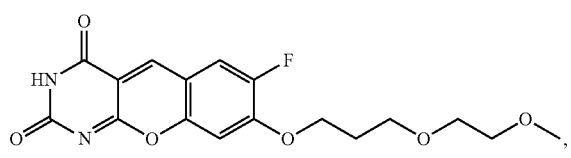,
and hydrates or pharmaceutically acceptable salts thereof.
7. A compound selected from the group consisting of:
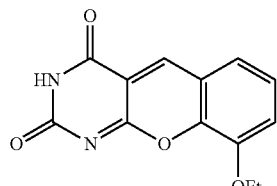,
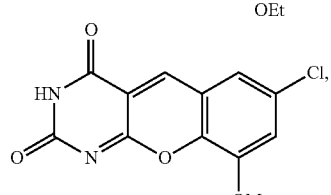,
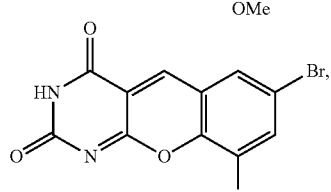,
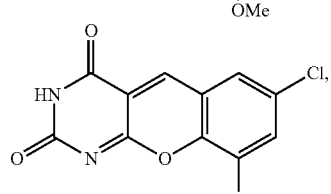,
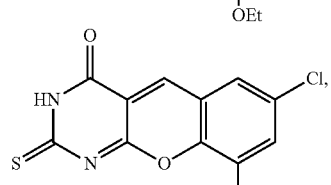,
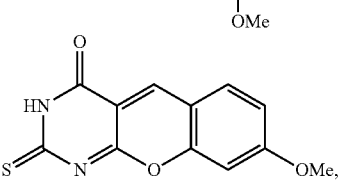,
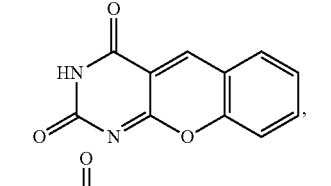,
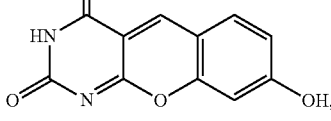,

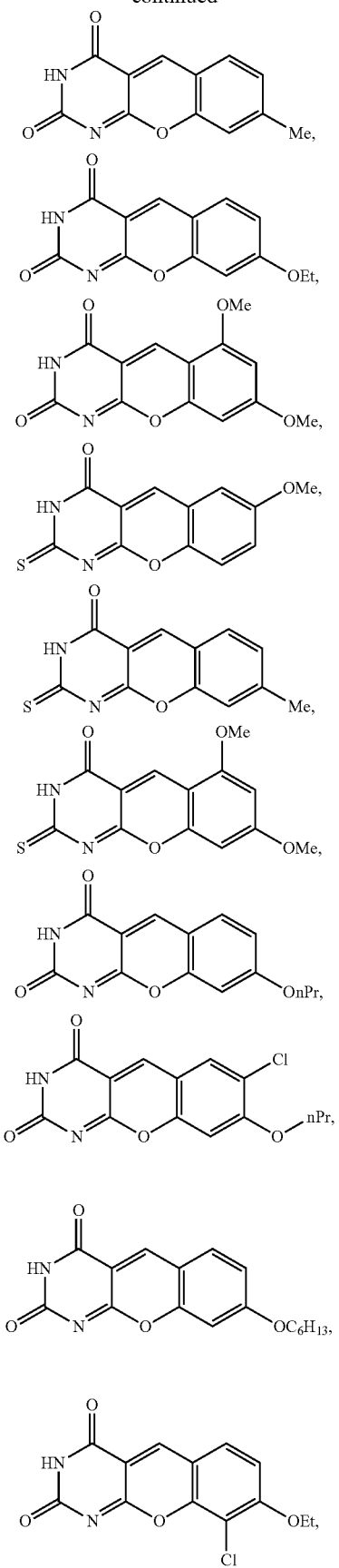
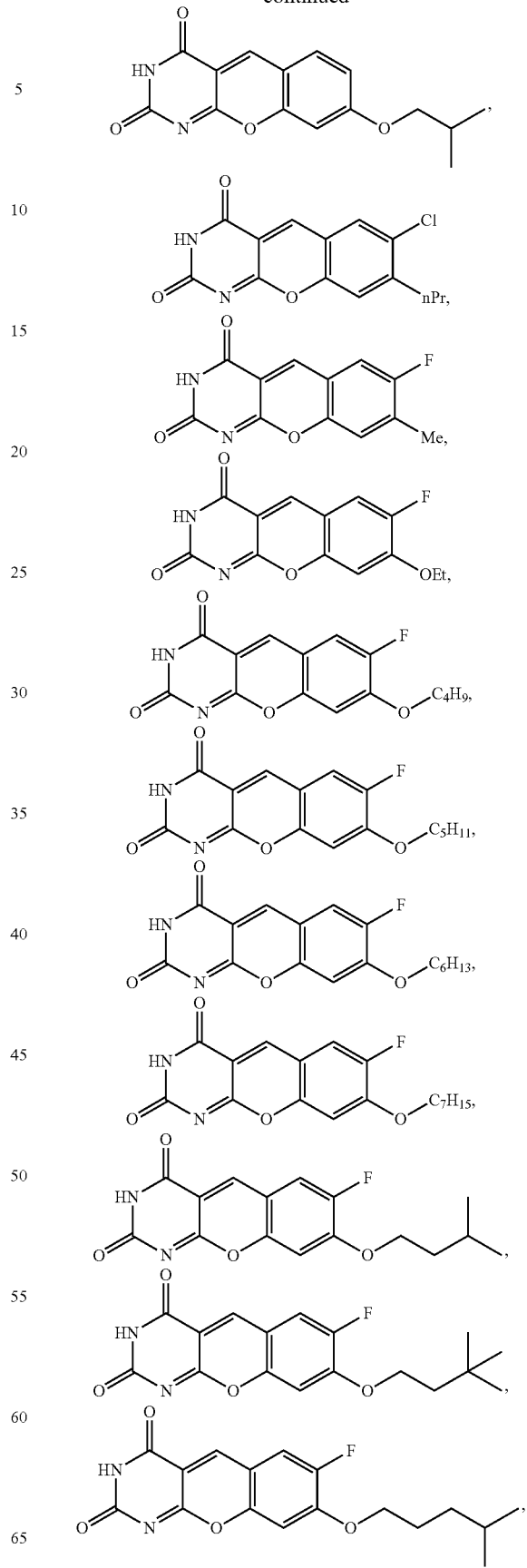

-continued
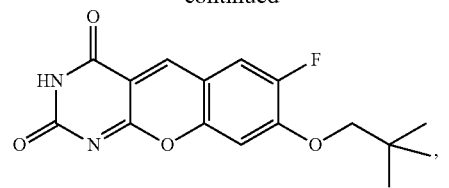
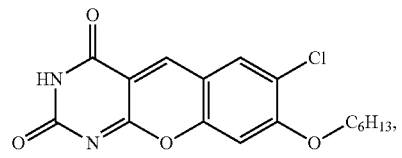
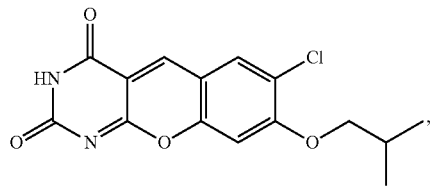
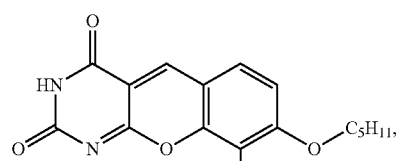
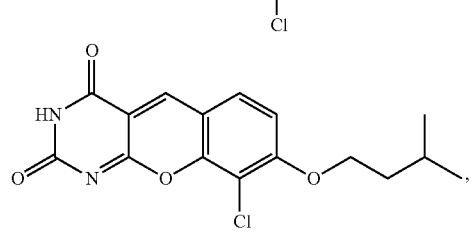
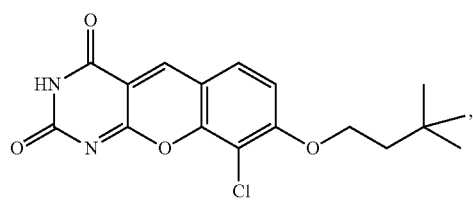
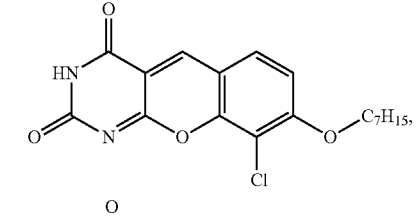
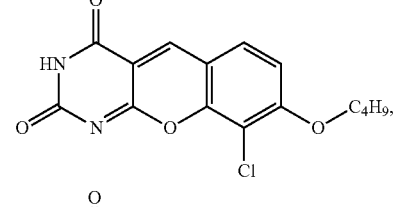
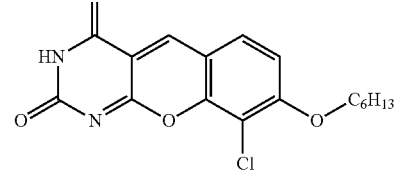
-continued
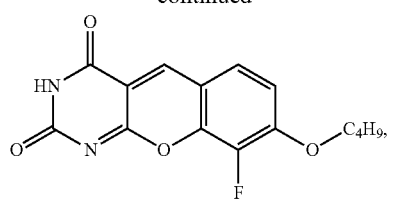
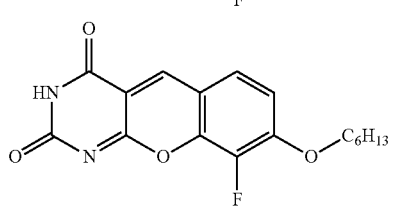
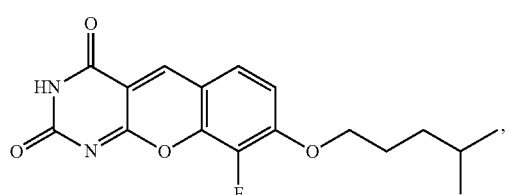
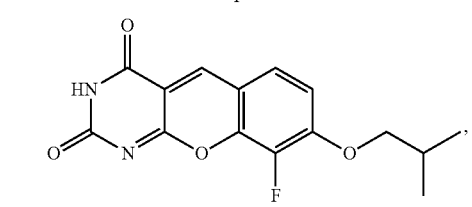
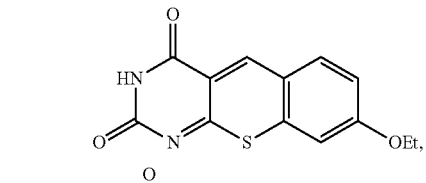
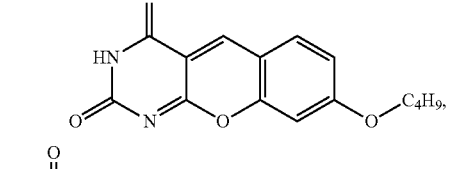
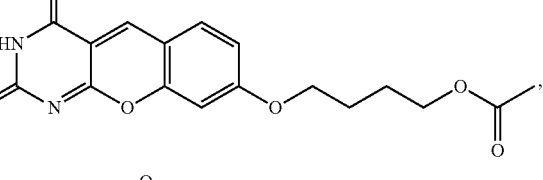
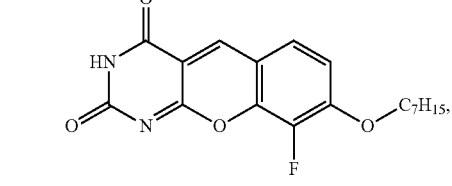
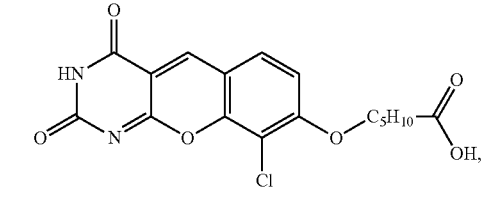

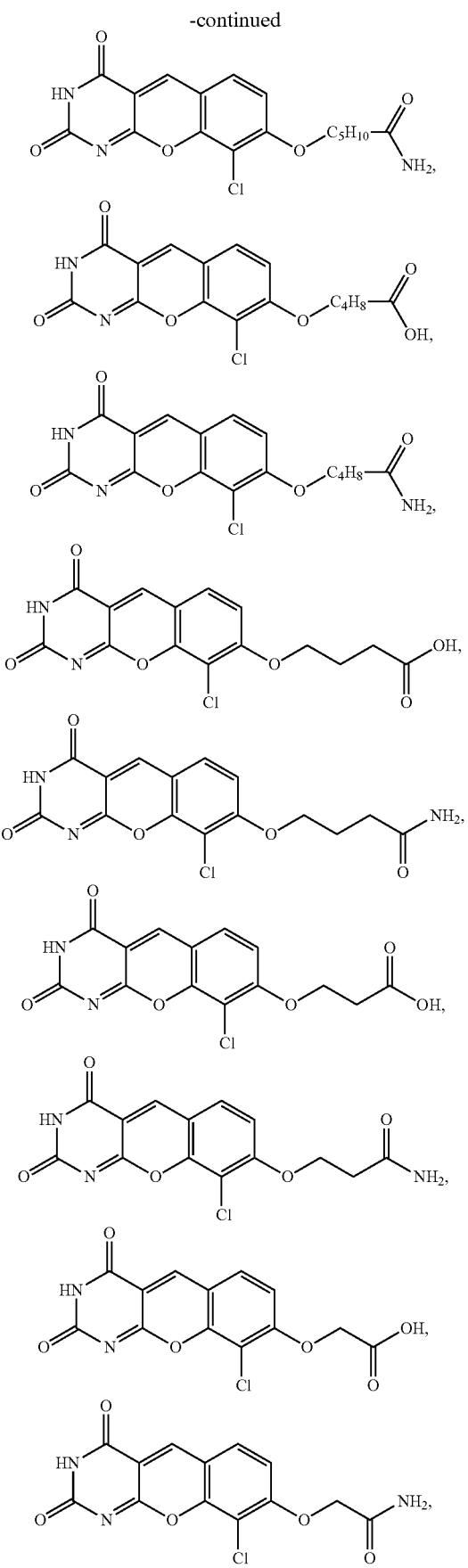
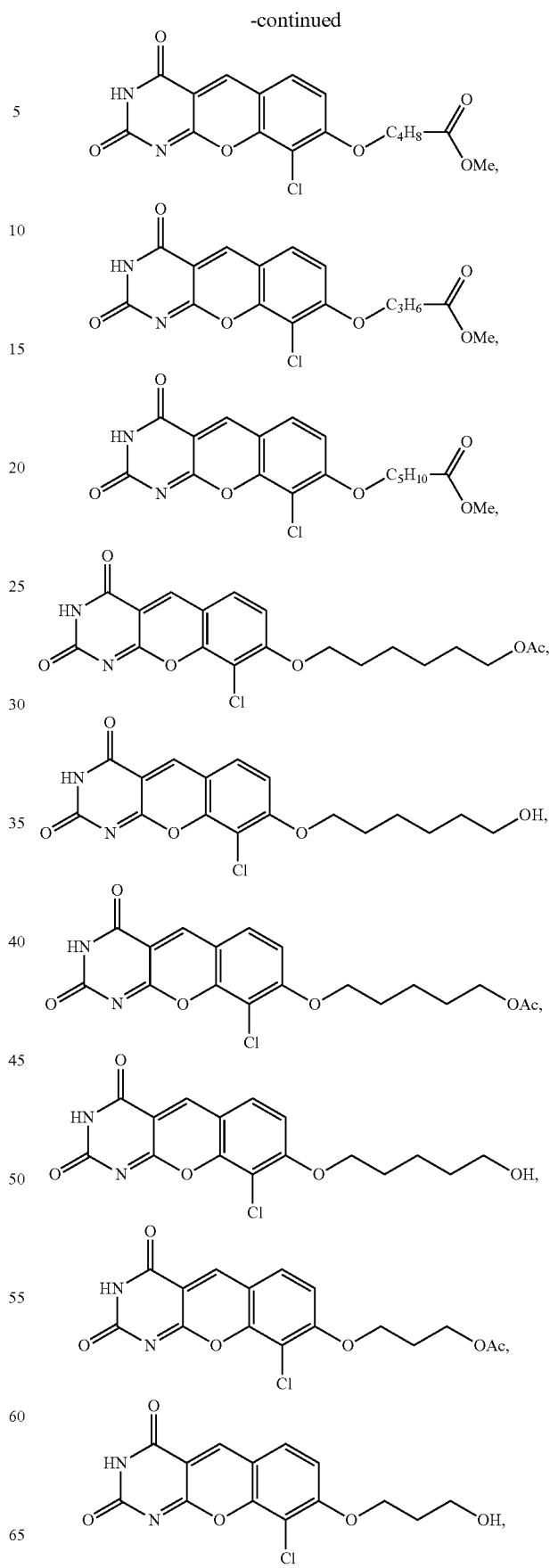

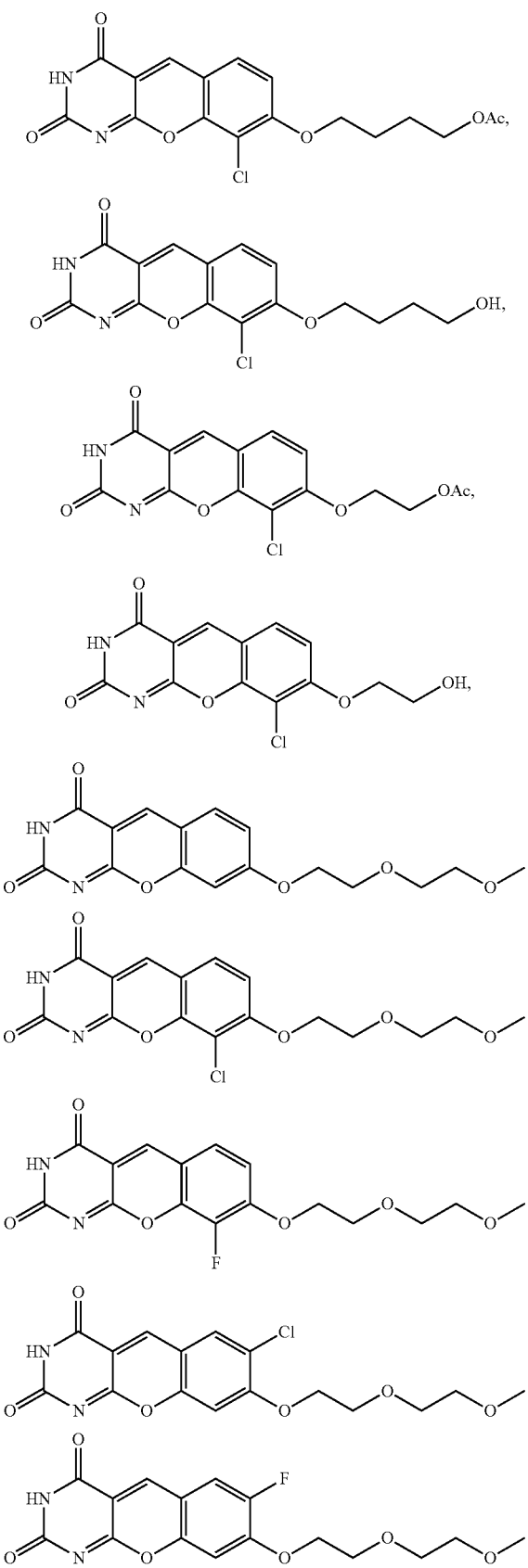
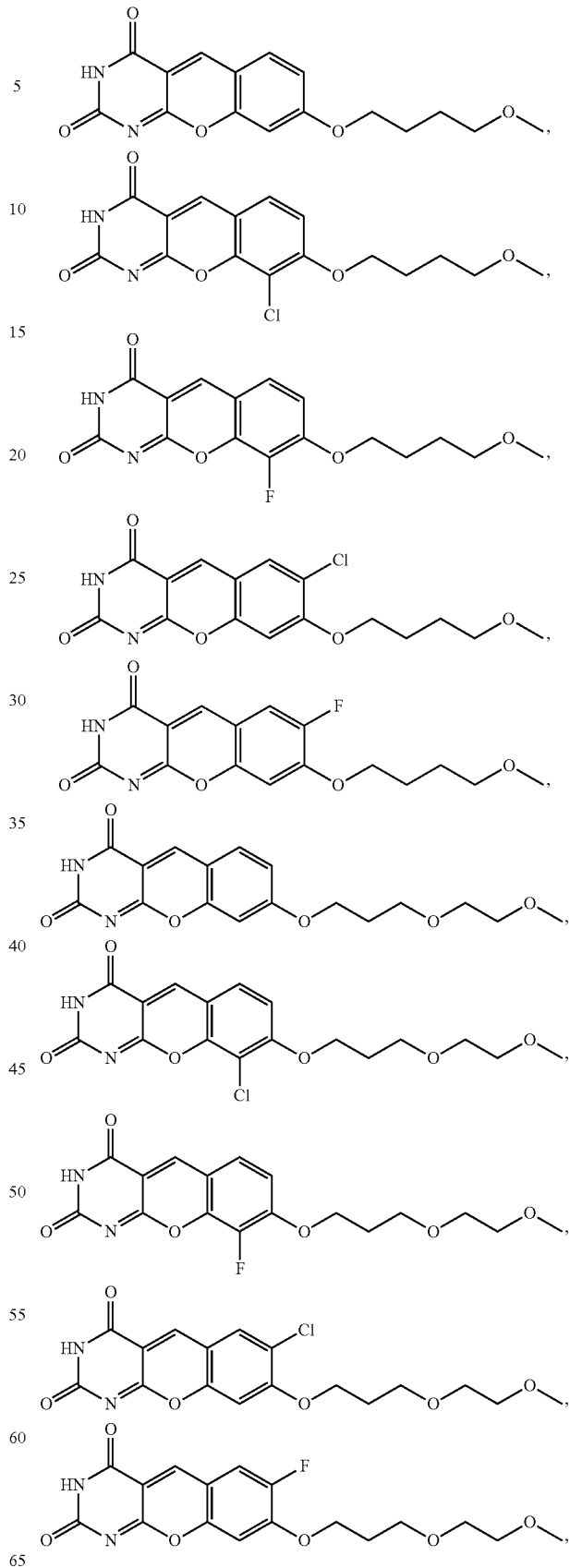
and hydrates or pharmaceutically acceptable salts thereof.

8. A compound selected from the group consisting of:

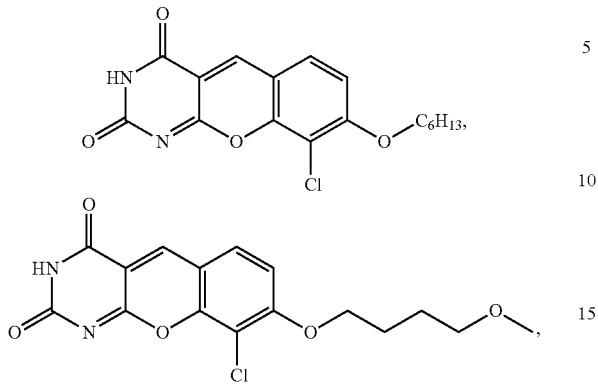

and hydrates or pharmaceutically acceptable salts thereof.

9. A compound capable of inhibiting NF-κB, having the structure of formula (I):

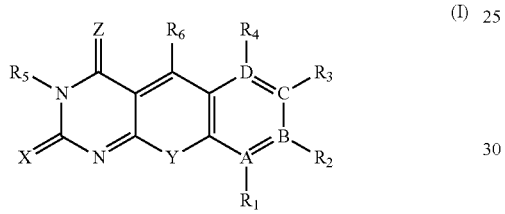

wherein:
A, B, C, and D are independently selected from the group consisting of carbon and nitrogen;
X, Y, and Z are independently selected from the group consisting of oxygen, sulfur, and $NR^a$;
$R_1$ is selected from the group consisting of no atom, hydrogen, halogen, $C_{1-9}$ alkyl, $C_{2-9}$ alkenyl, $C_{2-9}$ alkynyl, aryl, $C_{1-9}$ heterocyclic, —OH, —$OR^d$, —$OR^bOR^a$, —$OR^cOR^bOR^a$, —$OR^b(C=O)R^a$, —$O(C=O)R^d$, —$O(C=O)OR^a$, —$O(C=O)NR^bR^a$, cyano, nitro, —$CF_3$, —$CHF_2$, —$CH_2F$, —CHO, —COOH, —$COR^a$, —$COOR^a$, —$CONR^bR^a$, —$CONHCONR^bR^a$, —$NR^bR^a$, —$NHCOR^a$, —$NR^bCOR^a$, —CSOH, —$CSR^a$, —$CSOR^a$, —$CSNR^bR^a$, —$CSNHCSNR^bR^a$, —SH, —$SR^a$, —$S(C=O)R^a$, —$S(C=O)OR^a$, —$S(C=O)NR^bR^a$;
$R_2$ is selected from the group consisting of no atom, hydrogen, halogen, $C_{1-9}$ alkyl, $C_{2-9}$ alkenyl, $C_{2-9}$ alkynyl, aryl, $C_{1-9}$ heterocyclic, —OH, —$OR^d$, —$OR^bOR^a$, —$OR^cOR^bOR^a$, —$OR^b(C=O)R^a$, —$O(C=O)R^d$, —$O(C=O)OR^a$, —$O(C=O)NR^bR^a$, cyano, nitro, —$CF_3$, —$CHF_2$, —$CH_2F$, —CHO, —COOH, —$COR^a$, —$COOR^a$, —$CONR^bR^a$, —$CONHCONR^bR^a$, —$NR^bR^a$, —$NHCOR^a$, —$NR^bCOR^a$, —CSOH, —$CSR^a$, —$CSOR^a$, —$CSNR^bR^a$, —$CSNHCSNR^bR^a$, —SH, —$SR^a$, —$S(C=O)R^a$, —$S(C=O)OR^a$, —$S(C=O)NR^bR^a$;
$R_3$ and $R_4$ are independently selected from the group consisting of no atom, hydrogen, halogen, $C_{1-9}$ alkyl, $C_{2-9}$ alkenyl, $C_{2-9}$ alkynyl, aryl, $C_{1-9}$ heterocyclic, —OH, —$OR^d$, —$OR^bOR^a$, —$OR^cOR^bOR^a$, —$OR^b$ ($C=O)R^a$, —$O(C=O)R^d$, —$O(C=O)OR^a$, —$O(C=O)NR^bR^a$, cyano, nitro, —$CF_3$, —$CHF_2$, —$CH_2F$, —CHO, —COOH, —$COR^a$, —$COOR^a$, —$CONR^bR^a$, —$CONHCONR^bR^a$, —$NR^bR^a$, —$NHCOR^a$, —$NR^bCOR^a$, —CSOH, —$CSR^a$, —$CSOR^a$, —$CSNR^bR^a$, —$CSNHCSNR^bR^a$, —SH, —$SR^a$, —$S(C=O)R^a$, —$S(C=O)OR^a$, —$S(C=O)NR^bR^a$;
$R^5$ is selected from the group consisting of hydrogen, $C_{5-9}$ alkyl, $C_{2-9}$ alkenyl, $C_{2-9}$ alkynyl, aryl, $C_{1-9}$ heterocyclic, —$R^aCO$, —$R^aNHCO$, and —$R^aOCO$;
$R_6$ is selected from the group consisting of hydrogen, hydroxyl, amine, $C_{1-9}$ alkyl, $C_{2-9}$ alkenyl, $C_{2-9}$ alkynyl, aryl, and $C_{1-9}$ heterocyclic;
$R^a$ is selected from the group consisting of hydrogen, amine, $C_{1-9}$ alkyl, $C_{2-9}$ alkenyl, $C_{2-9}$ alkynyl, aryl, and $C_{1-9}$ heterocyclic;
$R^b$ and $R^c$ are independently selected from the group consisting of oxygen, amine, $C_{1-9}$ alkylene, $C_{2-9}$ alkenylene, $C_{2-9}$ alkynylene, arylene, and $C_{1-9}$ heterocyclic; and
$R^d$ is selected from the group consisting of hydrogen, amine, $C_{2-9}$ alkyl, $C_{2-9}$ alkenyl, $C_{2-9}$ alkynyl, aryl, and $C_{1-9}$ heterocyclic;
wherein:
if X is sulfur,
$R_2$ is selected from the group consisting of no atom, hydrogen, halogen, $C_{1-9}$ alkyl, $C_{2-9}$ alkenyl, $C_{2-9}$ alkynyl, aryl, $C_{1-9}$ heterocyclic, —$OR^d$, —$OR^bOR^a$, —$OR^cOR^bOR^a$, —$OR^b(C=O)R^a$, —$O(C=O)R^d$, —$O(C=O)OR^a$, —$O(C=O)NR^bR^a$, cyano, nitro, —$CF_3$, —$CHF_2$, —$CH_2F$, —CHO, —COOH, —$COR^a$, —$COOR^a$, —$CONR^bR^a$, —$CONHCONR^bR^a$, —$NR^bR^a$, —$NHCOR^a$, —$NR^bCOR^a$, —CSOH, —$CSR^a$, —$CSOR^a$, —$CSNR^bR^a$, —$CSNHCSNR^bR^a$, —SH, —$SR^a$, —$S(C=O)R^a$, —$S(C=O)OR^a$, —$S(C=O)NR^bR^a$; and,
$R^d$ is selected from the group consisting of amine, $C_{2-9}$ alkyl, $C_{2-9}$ alkenyl, $C_{2-9}$ alkynyl, aryl, and $C_{1-9}$ heterocyclic;
or a hydrate or pharmaceutically acceptable salt thereof, wherein the compound inhibits NF-κB DNA-binding activity.

10. A compound according to claim 9,
wherein:
X, Y, and Z are independently selected from the group consisting of oxygen and sulfur;
$R_1$ is selected from the group consisting of —H, —F, —Cl, —Br, and —OEt;
$R_2$ is selected from the group consisting of —H, —$CH_3$, —OH, —OEt, -Et, -nPr, —O-nPr, -OEtnPr, —$OC_4H_9$, —$OC_5H_{11}$, —$OC_6H_{13}$, —$OC_7H_{15}$, —O-isobutyl, —O-isopentyl, —$OC_nH_{2n}OMe$, —$OC_nH_{2n}OC_mH_{2m}OMe$, —$OC_nH_{2n}OH$, —$OC_nH_{2n}OC_mH_{2m}OH$, $OC_nH_{2n}OEt$, —$OC_nH_{2n}OC_mH_{2m}OEt$, —O—$C_nH_{2n}COOH$, —O—$C_nH_{2n}CONH2$, —O—$C_nH_{2n}CONHMe$,

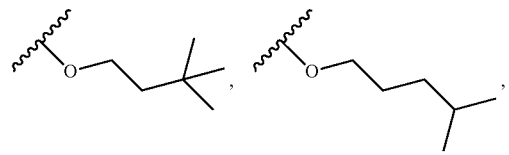

-continued

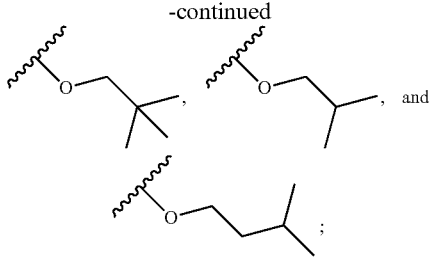

R$_3$ is selected from the group consisting of —H, —Cl, —Br, and —F;
R$_4$ is —H;
R$_5$ is —H; and
R$_6$ is selected from the group consisting of —H and —CH$_3$,
m is 2, 3, 4 or 5;
n is 2, 3, 4, or 5;
wherein:
if X is sulfur,
R$_2$ is selected from the group consisting of —H, —CH$_3$, —OEt, -Me, -Et, -nPr, —O-nPr, —OEt-nPr, —OC$_4$H$_9$, —OC$_5$H$_{11}$, —OC$_6$H$_{13}$, —OC$_7$H$_{15}$, —O-isobutyl, —O-isopentyl, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, —OC$_n$H$_{2n}$OEt, —OC$_n$H$_{2n}$OC$_m$H$_{2m}$OEt, —O—C$_n$H$_{2n}$COOH, —O—C$_n$H$_{2n}$CONH2, —O—C$_n$H$_{2n}$CONHMe,

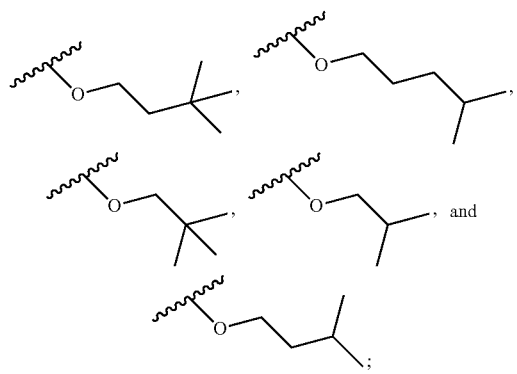

or a hydrate or pharmaceutically acceptable salt thereof.
11. A compound according to claim 9,
wherein:
X, Y, and Z are independently selected from the group consisting of oxygen and sulfur; and
R$_6$ is hydrogen,
wherein:
if X is sulfur,
R$_2$ is selected from the group consisting of no atom, hydrogen, halogen, C$_{1-9}$ alkyl, C$_{2-9}$ alkenyl, C$_{2-9}$ alkynyl, aryl, C$_{1-9}$ heterocyclic, —OR$^d$, —OR$^b$OR$^a$, —OR$^c$OR$^b$OR$^a$, —OR$^b$(C=O)R$^a$, —O(C=O)R$^d$, —O(C=O)OR$^a$, —O(C=O)NR$^b$R$^a$, cyano, nitro, —CF$_3$, —CHF$_2$, —CH$_2$F, —CHO, —COOH, —COR$^a$, —COOR$^a$, —CONR$^b$R$^a$, —CONHCONR$^b$R$^a$, —NR$^b$R$^a$, —NHCOR$^a$, —NR$^b$COR$^a$, —CSOH, —CSR$^a$, —CSOR$^a$, —CSNR$^b$R$^a$, —CSNHCSNR$^b$R$^a$, —SH, —SR$^a$, —S(C=O)R$^a$, —S(C=O)OR$^a$, —S(C=O)NR$^b$R$^a$; and, R$^d$ is selected from the group consisting of amine, C$_{2-9}$ alkyl, C$_{2-9}$ alkenyl, C$_{2-9}$ alkynyl, aryl, and C$_{1-9}$ heterocyclic;
or a hydrate or pharmaceutically acceptable salt thereof.
12. A compound according to claim 11,
wherein:
Z is oxygen;
R$_1$ and R$_3$ are selected from the group consisting of hydrogen, halogen, —CN, and —CF$_3$;
R$_2$ is selected from the group consisting of C$_{2-9}$ alkoxy, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, —OC$_n$H$_{2n}$OEt, —OC$_n$H$_{2n}$OC$_m$H$_{2m}$OEt, and —OH;
m is 2, 3, 4 or 5;
n is 2, 3, 4, or 5;
R$_4$ is selected from the group consisting of hydrogen, C$_{2-9}$ alkoxy and —OH,
or a hydrate or pharmaceutically acceptable salt thereof.
13. A compound according to claim 12,
wherein:
X and Y are oxygen; and
R$_4$ is hydrogen
or a hydrate or pharmaceutically acceptable salt thereof.
14. A compound according to claim 13, wherein the compound is selected from the group consisting of:

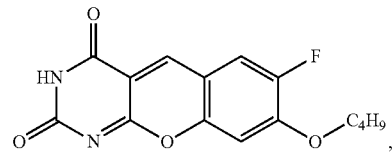

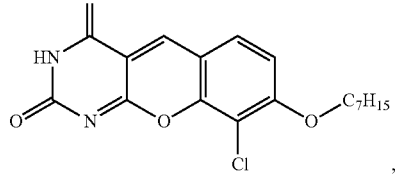

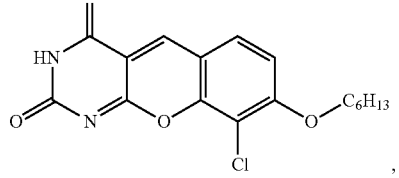

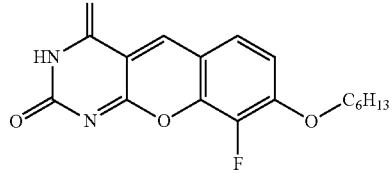

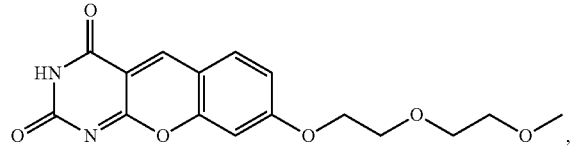

-continued
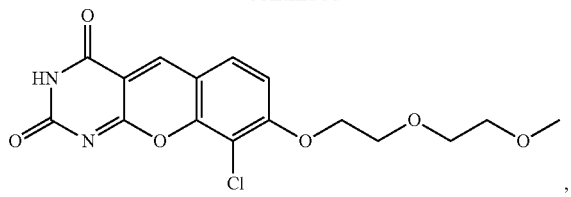
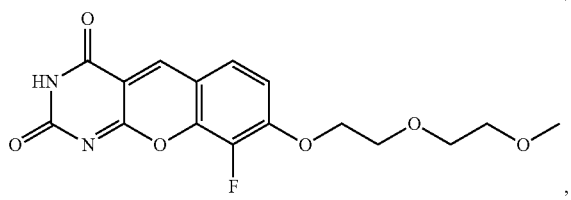
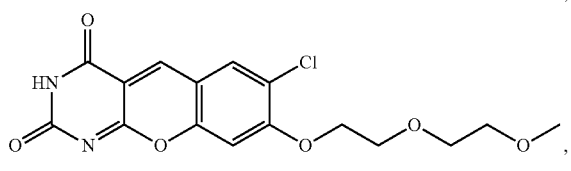
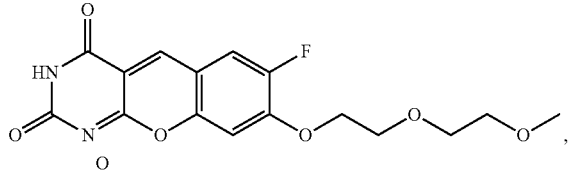
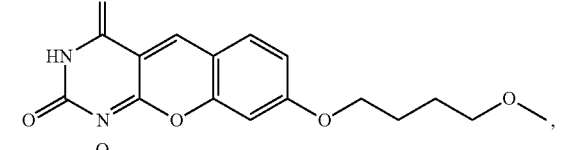
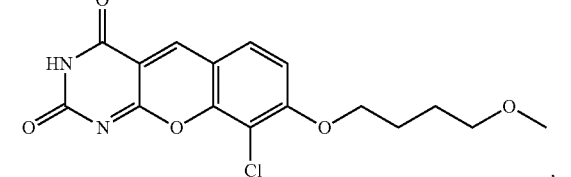
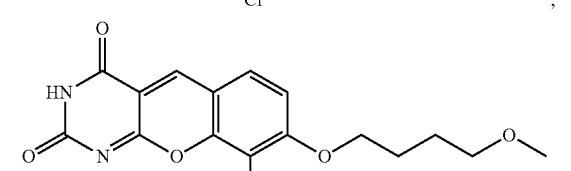
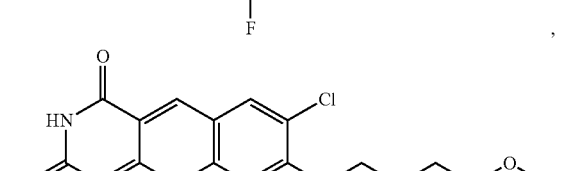
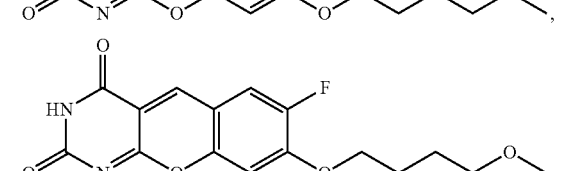
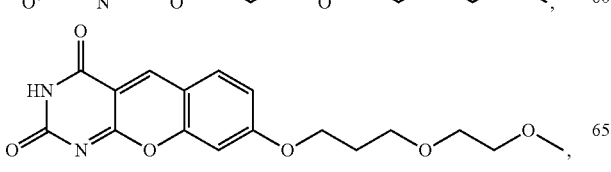
-continued
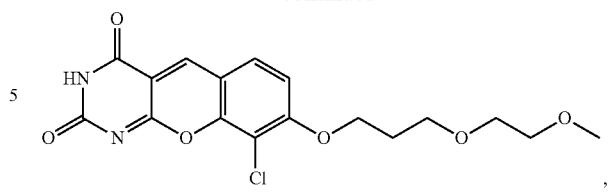
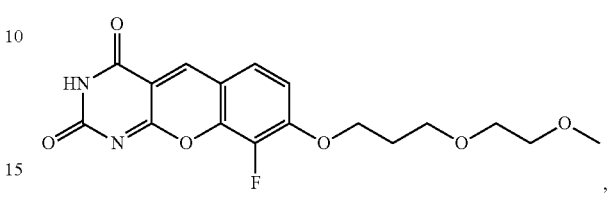
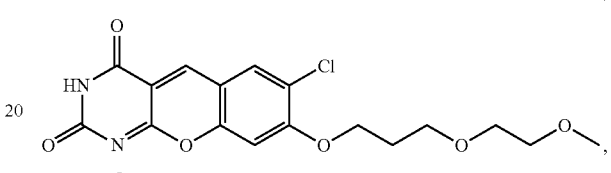
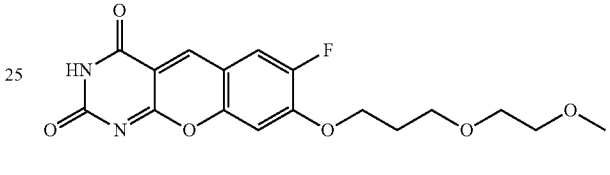
and hydrates or pharmaceutically acceptable salts thereof.
15. A compound capable of inhibiting NF-κB, selected from the group consisting of:
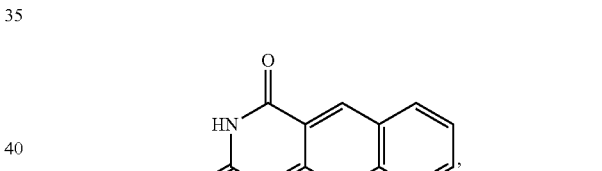
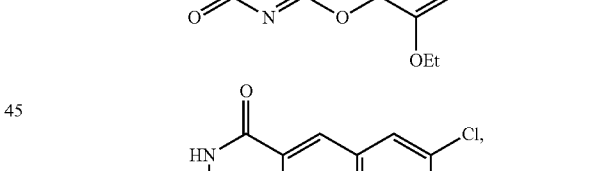
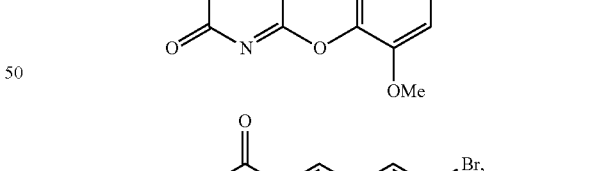
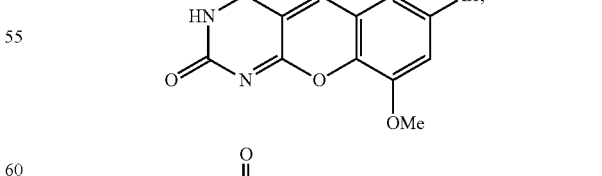

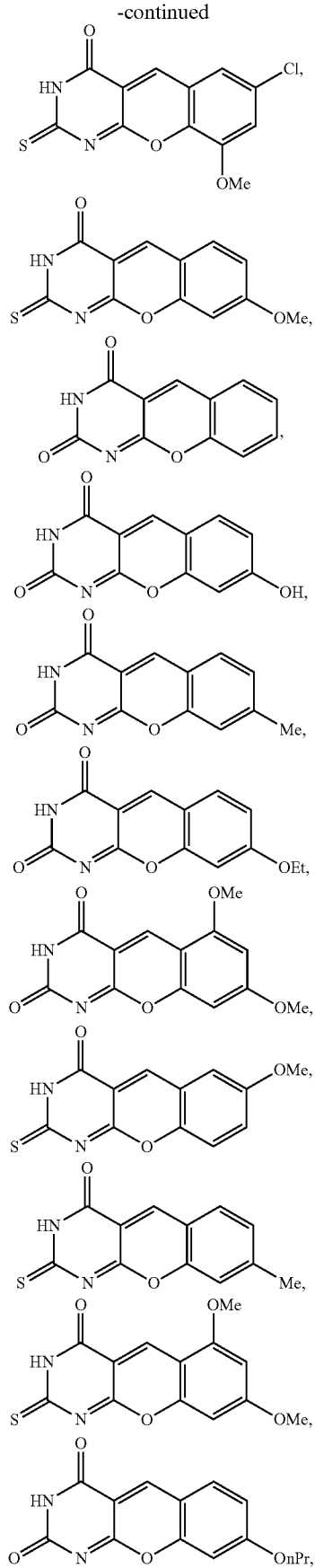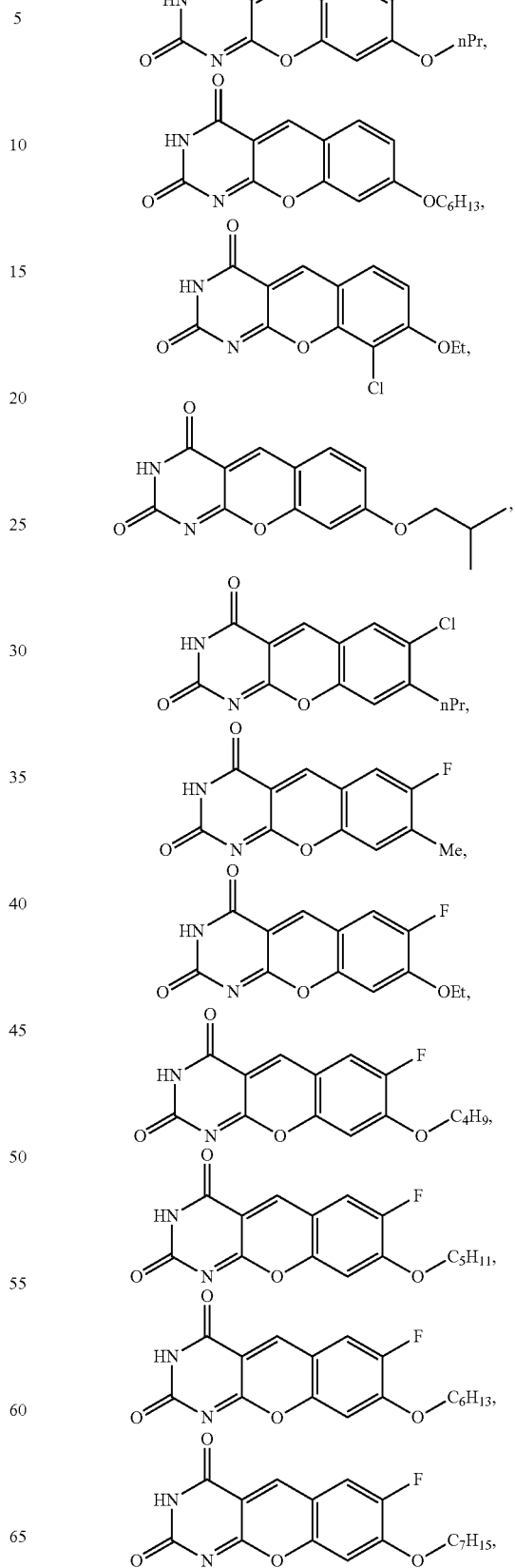

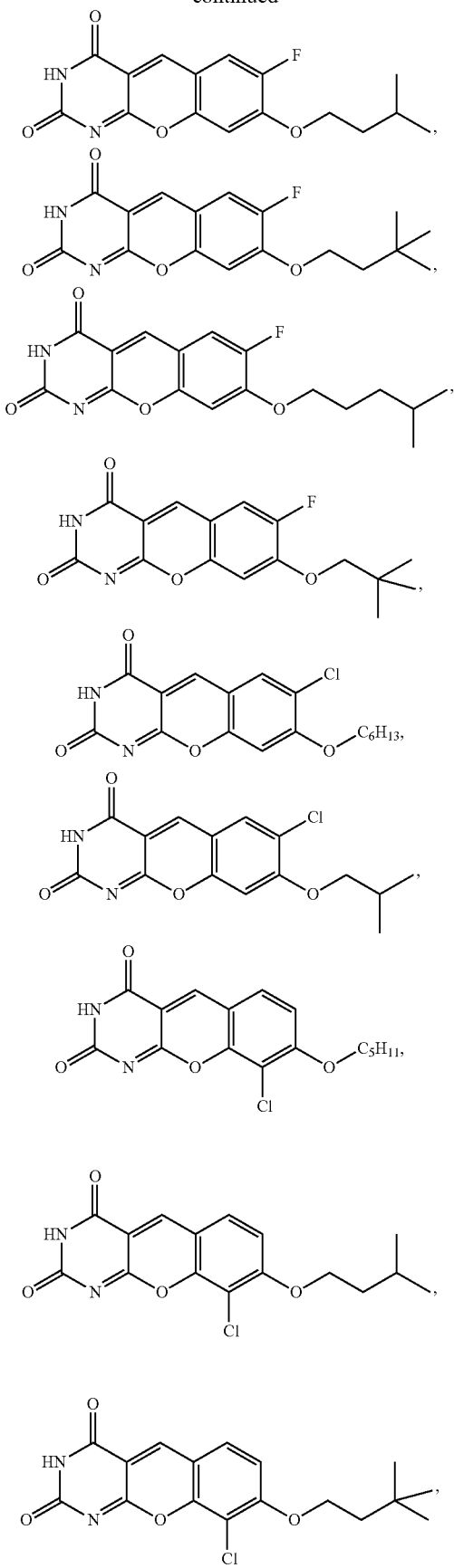
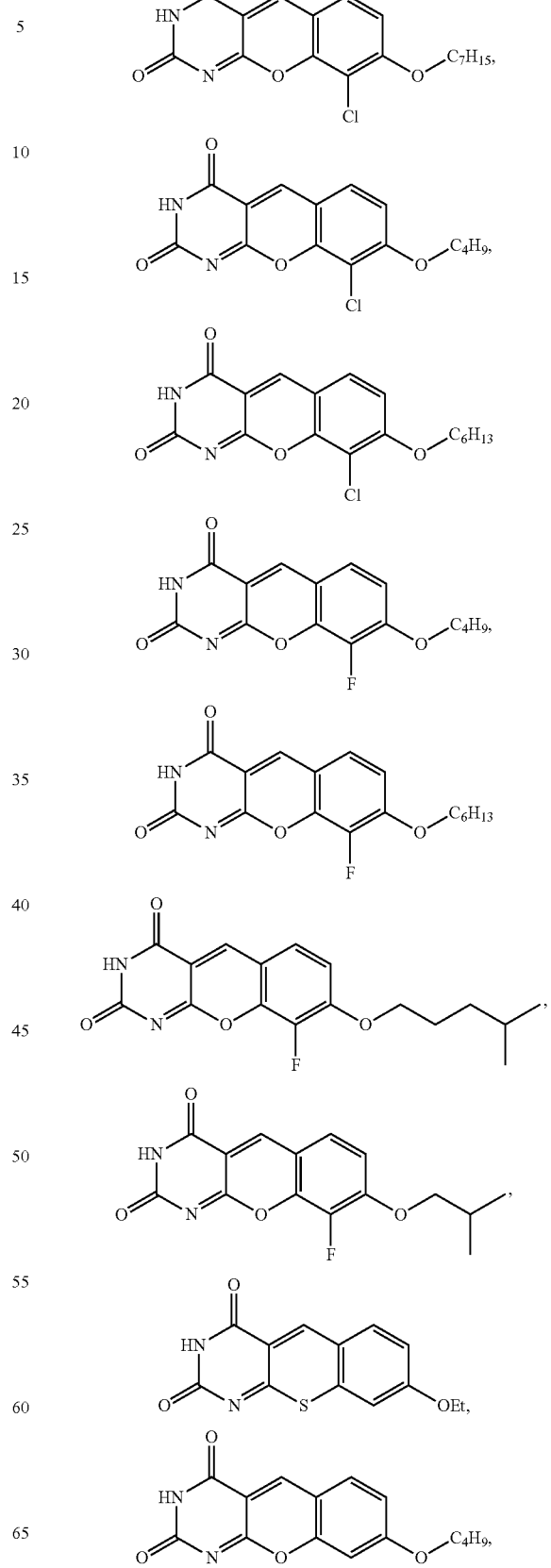

127
-continued

128
-continued

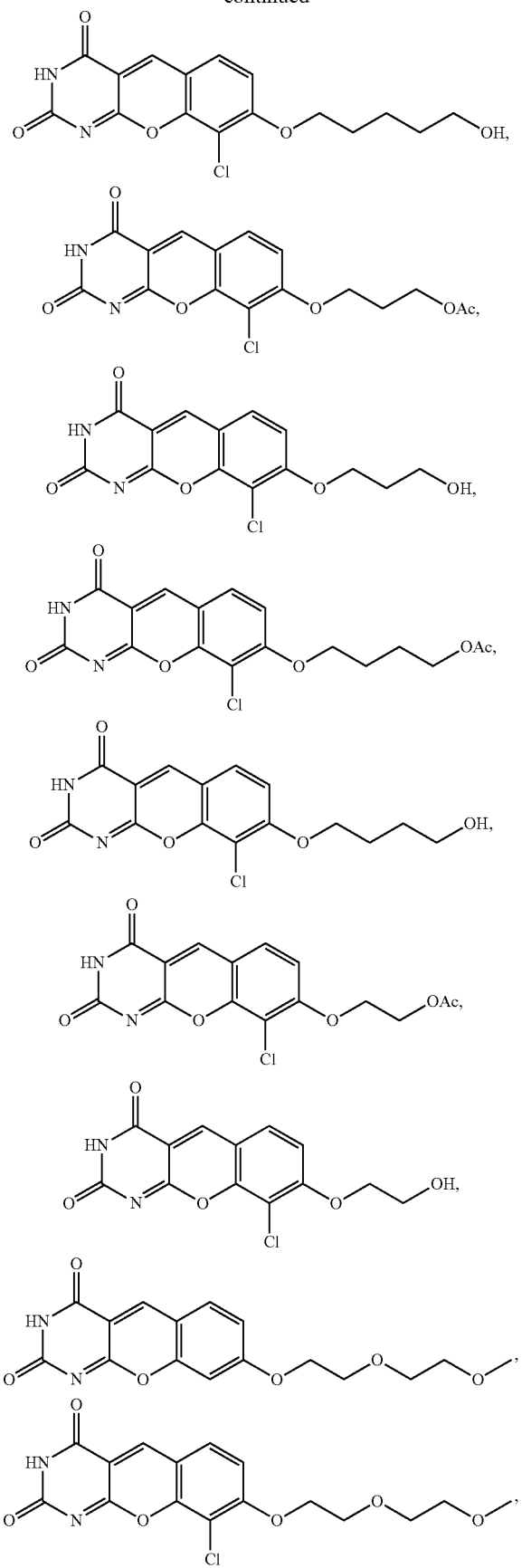
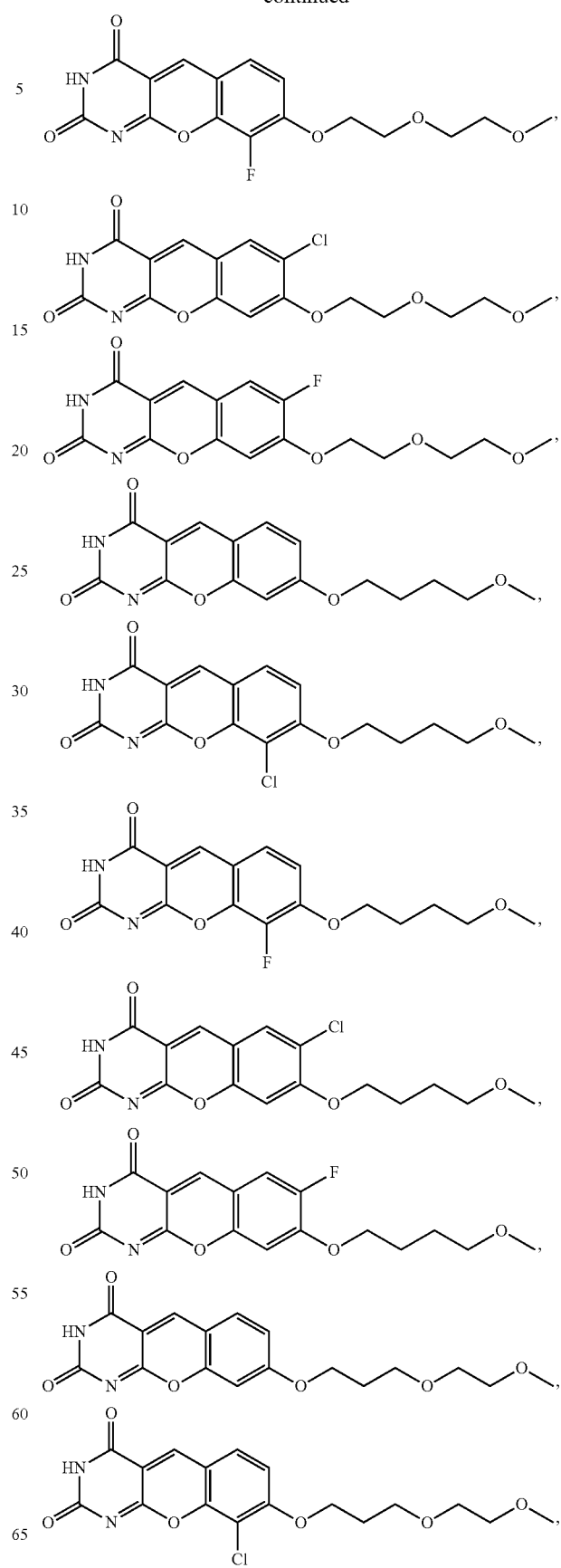

-continued

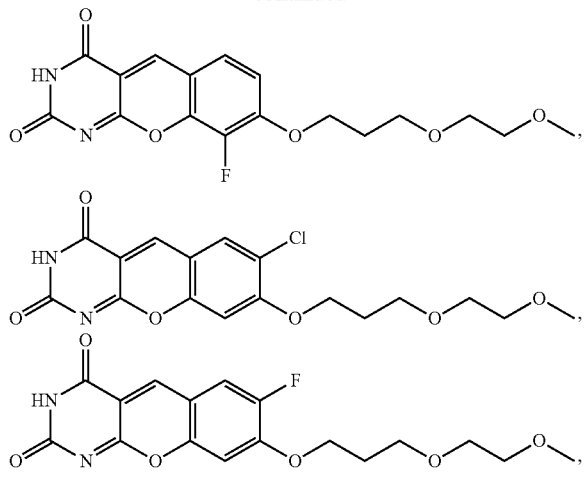

and hydrates or pharmaceutically acceptable salts thereof, wherein the compound inhibits NF-κB DNA-binding activity.

16. A compound capable of inhibiting NF-κB, selected from the group consisting of:

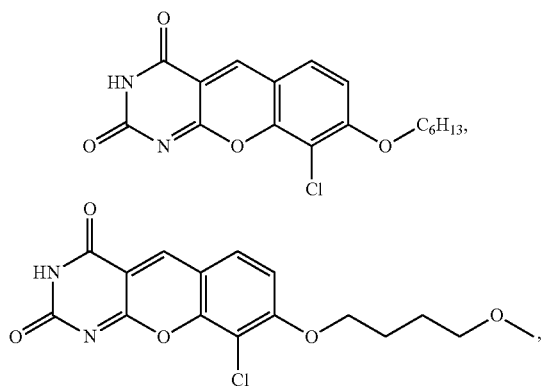

and hydrates or pharmaceutically acceptable salts thereof, wherein the compound inhibits NF-κB DNA-binding activity.

17. A pharmaceutical composition comprising a pharmaceutically acceptable carrier and a compound according to claim 1.

18. The pharmaceutical composition of claim 17, wherein the compound is selected from the group consisting of:

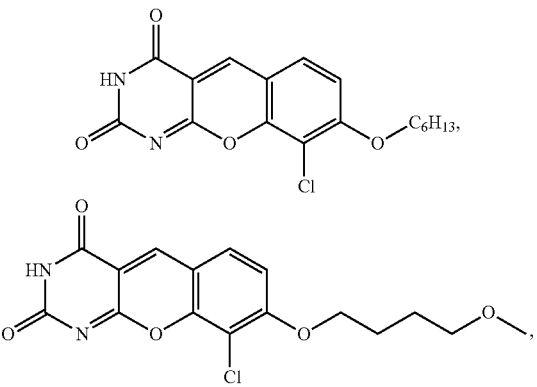

and hydrates or pharmaceutically acceptable salts thereof.

19. A method of inhibiting NF-κB in a cell, comprising: contacting the cell with a compound according to claim 1.

20. The method of claim 19, wherein the compound is selected from the group consisting of:

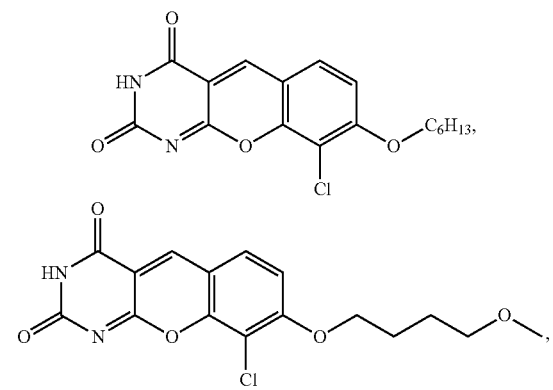

and hydrates or pharmaceutically acceptable salts thereof.

* * * * *

UNITED STATES PATENT AND TRADEMARK OFFICE
CERTIFICATE OF CORRECTION

PATENT NO. : 10,226,464 B2
APPLICATION NO. : 15/393507
DATED : March 12, 2019
INVENTOR(S) : Samedy Ouk et al.

It is certified that error appears in the above-identified patent and that said Letters Patent is hereby corrected as shown below:

In the Claims

In Claim 1, Under Column 104, Line 16:
It reads: -SH, -S(C=O)$R^a$, -S(C=O)O$R^a$, -
It should be: -- -SH, -S$R^a$, -S(C=O)$R^a$, -S(C=O)O$R^a$, --

In Claim 3, Column 105, Line 44:
It reads: -SH, -S(C=O)$R^a$, -S(C=O)O$R^a$, - S(C=O)
It should be: -- -SH, -S$R^a$, -S(C=O)$R^a$, -S(C=O)O$R^a$, - S(C=O) --

Signed and Sealed this
Fourteenth Day of May, 2019

Andrei Iancu
*Director of the United States Patent and Trademark Office*